(12) United States Patent
Kobayashi et al.

(10) Patent No.: US 7,517,661 B2
(45) Date of Patent: Apr. 14, 2009

(54) METHODS OF SCREENING FOR LIGANDS FOR FPRL2

(75) Inventors: Makoto Kobayashi, Osaka (JP); Yugo Habata, Tsukuba (JP); Ryo Fujii, Tsukuba (JP); Shuji Hinuma, Tsukuba (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 340 days.

(21) Appl. No.: 10/554,234

(22) PCT Filed: Apr. 22, 2004

(86) PCT No.: PCT/JP2004/005829

§ 371 (c)(1),
(2), (4) Date: Oct. 21, 2005

(87) PCT Pub. No.: WO2004/095023

PCT Pub. Date: Nov. 4, 2004

(65) Prior Publication Data

US 2007/0009513 A1    Jan. 11, 2007

(30) Foreign Application Priority Data

Apr. 23, 2003    (JP) .............................. 2003-118760

(51) Int. Cl.
*G01N 33/567*    (2006.01)
*C07K 14/705*    (2006.01)

(52) U.S. Cl. ..................... 435/7.21; 436/501; 530/350

(58) Field of Classification Search ....................... None
See application file for complete search history.

(56) References Cited

FOREIGN PATENT DOCUMENTS

| WO | WO 97/22004    | 6/1997  |
| WO | WO 00/09538    | 2/2000  |
| WO | WO 02/068600 A2 | 9/2002 |
| WO | WO03/080098    | 10/2003 |

OTHER PUBLICATIONS

T. Christophe, et al., "The Synthetic Peptide Trp-Lys-Tyr-Met-Val-Met-NH2 Specifically Activates Neutrophils through FPRL1/Liproxin...", The Journal of Biological Chemistry, (2001), vol. 276, No. 24, pp. 21585-21593.

S. Fukusumi, et al., "Characteristics and Distribution of Endogenous RFamide-related Peptide-1", Biochim Biophys Acta, (2001), vol. 1540, No. 3, pp. 221-232.

N. Minamino, et al., "Neuromedin C: A Rombesin-Like Peptide Identified in Porcine Spinal Cord", Biochemical and Biophysical Research Communications, (1984), vol. 119, No. 1, pp. 14-20.

P.M. Murphy, et al., "A Structural Homologue of the N-Formyl Peptide Receptor", The Journal of Biological Chemistry, (1992), vol. 267, No. 11, pp. 7637-7643.

L. Bao, et al., "Mapping of Genes for the Human C5a Receptor (C5AR), Human FMLP Receptor (FPR), and Two FMLP Receptor Homologue Orphan Receptors (FPRH1, FPRH2) to Chromosome 19", Genomics (1992), vol. 13, No. 2, pp. 437-440.

A.C. Mahon, et al., "The Small Cardioactive Peptides A and B of Aplysia are Derived from a Common Precursor Molecule", Proc. Natl. Acad. Sci. USA, (1985), vol. 82, No. 11, pp. 3925-3929.

P. M. Conn, et al., "A New Receptor for Growth Hormone-Release Peptide", Science, (1996), vol. 273, No. 5277, p. 923.

M. Durstin, et al., "Differential Expression of Members of the N-Formylpeptide Receptor Gene Cluster in Human Phagocytes", Biochemical and Biophysical Research Communications, (1994), 201(1): 174-179.

A. Betten, et al., "A Proinflammatory Peptide from Helicobacter Pylori Activates Monocytes to Induce Lymphocyte Dysfunction and Apoptosis", The Journal of Clinical Investigation, (2001), 108(8): 1221-1228.

M. Harada, et al., "N-Formylated Humanin Activates Both Formyl Peptide Receptor-Like 1 and 2", Biochemical and Biophysical Research Communications, (2004), 324: 255-261.

T. Christophe, et al., "The Synthetic Peptide Trp-Lys-Tyr-Met-Val-Met-NH2 Specifically Activates Neutrophils through FPRL1/Lipoxin A4 Receptors and Is an Agonist for the Orphan Monocyte-expressed Chemoattractant Receptor FPRL2", The Journal of Biological Chemistry, (2001), 276(24): 21585-21593.

*Primary Examiner*—John D Ulm
(74) *Attorney, Agent, or Firm*—Edwards Angell Palmer & Dodge LLP; David G. Conlin; Amy DeCloux

(57) ABSTRACT

The use of a G-protein coupled receptor protein comprising the same or substantially the same amino acid sequence as the amino acid sequence represented by SEQ ID NO: 1, or a salt thereof and a ligand peptide comprising the amino acid sequence represented by any of SEQ ID NO: 3 to 7, or a salt thereof, enables efficient screening of an agonist or antagonist for the above receptor protein or a salt thereof.

10 Claims, 4 Drawing Sheets

SEQUENCE LISTING

<160> NUMBER OF SEQ ID NOS: 7

<210> SEQ ID NO 1
<211> LENGTH: 353
<212> TYPE: PRT
<213> ORGANISM: Homo sapiens

<400> SEQUENCE: 1

```
Met Glu Thr Asn Phe Ser Ile Pro Leu Asn Glu Thr Glu Val Leu
                  5                  10                  15

Pro Glu Pro Ala Gly His Thr Val Leu Trp Ile Phe Ser Leu Val
                 20                  25                  30

His Gly Val Thr Phe Val Phe Gly Val Leu Gly Asn Gly Leu Val Ile
                 35                  40                  45

Trp Val Ala Gly Phe Arg Met Thr Arg Thr Val Asn Thr Ile Cys Tyr
 50                  55                                  60

Leu Asn Leu Ala Leu Ala Asp Phe Ser Phe Ser Ala Ile Leu Pro Phe
 65                  70                  75                  80

Arg Met Val Ser Val Ala Met Arg Glu Lys Trp Pro Phe Ala Ser Phe
                 85                  90                  95

Leu Cys Lys Leu Val His Val Met Ile Asp Ile Asn Leu Phe Val Ser
                100                 105                 110

Val Tyr Leu Ile Thr Ile Ile Ala Leu Asp Arg Cys Ile Cys Val Leu
                115                 120                 125

His Pro Ala Trp Ala Gln Asn His Arg Thr Met Ser Leu Ala Lys Arg
130                 135                 140

Val Met Thr Gly Leu Trp Ile Phe Thr Ile Val Leu Thr Leu Pro Asn
145                 150                 155                 160

Phe Ile Phe Trp Thr Thr Ile Ser Thr Thr Asn Gly Asp Thr Tyr Cys
                165                 170                 175

Ile Phe Asn Phe Ala Phe Trp Gly Asp Thr Ala Val Glu Arg Leu Asn
                180                 185                 190

Val Phe Ile Thr Met Ala Lys Val Phe Leu Ile Leu His Phe Ile Ile
                195                 200                 205

Gly Phe Thr Val Pro Met Ser Ile Ile Thr Val Cys Tyr Gly Ile Ile
                210                 215                 220

Ala Ala Lys Ile His Arg Asn His Met Ile Lys Ser Ser Arg Pro Leu
225                 230                 235                 240

Arg Val Phe Ala Ala Val Val Ala Ser Phe Phe Ile Cys Trp Phe Pro
                245                 250                 255

Tyr Glu Leu Ile Gly Ile Leu Met Ala Val Trp Leu Lys Glu Met Leu
                260                 265                 270

Leu Asn Gly Lys Tyr Lys Ile Ile Leu Val Leu Ile Asn Pro Thr Ser
                275                 280                 285

Ser Leu Ala Phe Phe Asn Ser Cys Leu Asn Pro Ile Leu Tyr Val Phe
                290                 295                 300

Met Gly Arg Asn Phe Gln Glu Arg Leu Ile Arg Ser Leu Pro Thr Ser
305                 310                 315                 320

Leu Glu Arg Ala Leu Thr Glu Val Pro Asp Ser Ala Gln Thr Ser Asn
                325                 330                 335

Thr His Thr Thr Ser Ala Ser Pro Pro Glu Glu Thr Glu Leu Gln Ala
                340                 345                 350

Met
```

<210> SEQ ID NO 2
<211> LENGTH: 1059
<212> TYPE: DNA
<213> ORGANISM: Homo sapiens

<400> SEQUENCE: 2

```
atggaaacca acttctccat tcctctgaat gaaactgagg aggtgctccc tgagcctgct        60
ggccacaccg ttctgtggat cttctcattg ctagtccacg gagtcacctt tgtcttcggg       120
gtcctgggca atgggcttgt gatctgggtg gctggattcc ggatgacacg cacagtcaac       180
accatctgtt acctgaacct ggccctagct gacttctctt tcagtgccat cctaccattc       240
cgaatggtct cagtcgccat gagagaaaaa tggcctttg cgtcattcct atgtaagtta       300
gttcatgtta tgatagacat caacctgttt gtcagtgtct acctgatcac catcattgct       360
ctggaccgct gtatttgtgt cctgcatcca gcctgggccc agaaccatcg caccatgagt       420
ctggccaaga gggtgatgac gggactctgg attttcacca tagtccttac cttaccaaat       480
ttcatcttct ggactacaat aagtactacg aatggggaca catactgtat tttcaacttt       540
gcattctggg gtgacactgc tgtagagagg ttgaacgtgt tcattaccat ggccaaggtc       600
tttctgatcc tccacttcat tattggcttc acggtgccta tgtccatcat acagtctgc        660
tatgggatca tcgctgccaa aattcacaga aaccacatga ttaaatccag ccgtccctta       720
cgtgtcttcg ctgctgtggt ggcttctttc ttcatctgtt ggttccctta tgaactaatt       780
ggcattctaa tggcagtctg gctcaaagag atgttgttaa atggcaaata caaaatcatt       840
cttgtcctga ttaacccaac aagctccttg gccttttta acagctgcct caacccaatt       900
ctctacgtct ttatgggtcg taacttccaa gaaagactga ttcgctcttt gcccactagt       960
ttggagaggg ccctgactga ggtccctgac tcagcccaga ccagcaacac acacaccact      1020
tctgcttcac ctcctgagga gacggagtta caagcaatg                             1059
```

<210> SEQ ID NO 3
<211> LENGTH: 6
<212> TYPE: PRT
<213> ORGANISM: Artificial Sequence
<220> FEATURE:
<223> OTHER INFORMATION: amino acid sequence of GHRP-6
<220> FEATURE:
<223> OTHER INFORMATION: Trp is a D-form

<400> SEQUENCE: 3

His Trp Ala Trp Phe Lys
 1               5

<210> SEQ ID NO 4
<211> LENGTH: 11
<212> TYPE: PRT
<213> ORGANISM: Aplysia sp.

<400> SEQUENCE: 4

Ala Arg Pro Gly Tyr Leu Ala Phe Pro Arg Met
 1               5                  10

<210> SEQ ID NO 5
<211> LENGTH: 12
<212> TYPE: PRT
<213> ORGANISM: Sus scrofa

<400> SEQUENCE: 5

-continued

```
Met Pro His Ser Phe Ala Asn Leu Pro Leu Arg Phe
1               5                   10

<210> SEQ ID NO 6
<211> LENGTH: 36
<212> TYPE: PRT
<213> ORGANISM: Homo sapiens

<400> SEQUENCE: 6

Tyr Pro Ser Lys Pro Asp Asn Pro Gly Glu Asp Ala Pro Ala Glu Asp
1               5                   10                  15

Leu Ala Arg Tyr Tyr Ser Ala Leu Arg His Tyr Ile Asn Leu Ile Thr
            20                  25                  30

Arg Gln Arg Tyr
            35

<210> SEQ ID NO 7
<211> LENGTH: 10
<212> TYPE: PRT
<213> ORGANISM: Homo sapiens

<400> SEQUENCE: 7

Gly Asn His Trp Ala Val Gly His Leu Met
1               5                   10
```

METHODS OF SCREENING FOR LIGANDS FOR FPRL2

This application is National Phase filing of International Patent Application No. PCT/JP2004/005829, filed Apr. 22, 2004.

FIELD OF THE INVENTION

The present invention relates to a novel use of G protein-coupled receptor protein (FPRL2).

BACKGROUND ART

FPRL2 is known as one of orphan G protein-coupled receptor proteins (Genomics, 13 (2), 437-440 (1992)).

As an agonist for FPRL2, Trp-Lys-Tyr-Met-Val-Met-NH$_2$ (SEQ ID NO:8) as a synthetic peptide is reported. It is also reported that FPRL2 is highly expressed in monocytes (J Biol. Chem., Jun. 15, 2001; 276 (24): 21585-93).

GHRP-6 is known as a synthetic GHS (growth hormone secretagogue) peptide (Science, Aug. 16, 1996; 273 (5277): 923).

SCPA is a neuropeptide derived from sea hare or Aplysia and reportedly associated with regulation of heart beats (Proc. Natl. Acad. Sci. USA, June 1985; 82(11): 3925-3929).

RFRPs such as RFRP-1-12, etc. have been reported to have a prolactin secretion stimulating action, etc. (Biochim. Biophys. Acta, Sep. 26, 2001; 1540(3): 221-32).

Neuropeptide Y (NPY) is known to be involved in regulation of eating behavior, regulation of biological rhythm, depression or anxiety, and other higher mental functions (ZU-KAI HORMONE-NO-SUBETE (Illustrated All About Hormones), 1998, Igakunosekaisha, Inc., Section entitled NPY (pages 152-164).

Neuromedin C has been reported to be a bombesin-like peptide (Biochem. Biophys. Res. Commun., Feb. 29, 1984; 119(1): 14-20).

The present invention intends to identify a novel ligand for FPRL2 and provide use of FPRL2 and its ligand. That is, the present invention intends to provide a method of screening a compound (antagonist or agonist) or a salt thereof that changes the binding property of a ligand peptide to FPRL2, a kit for said screening, a compound (antagonist or agonist) or a salt thereof that changes the binding property of a ligand peptide to FPRL2 obtained by the screening method or the screening kit, and a pharmaceutical comprising a compound (antagonist or agonist) or a salt thereof that changes the binding property of a ligand peptide to FPRL2, and the like.

DISCLOSURE OF INVENTION

The present inventors made extensive studies to solve the foregoing problems and as a result, found that GHRP-6 (SEQ ID NO: 3), SCPA (SEQ ID NO: 4), human RFRP-1-12 (SEQ ID NO: 5), pNPY (SEQ ID NO: 6) and human neuromedin C (SEQ ID NO: 7), which are C-terminal amide peptides, exhibit a ligand activity on FPRL2, and further that FPRL2 is highly expressed in the affected synovial membrane of the patient with RA (rheumatoid arthritis). Based on these findings, the inventors have continued further investigations and have come to attain the present invention.

That is, the present invention provides the following features:

[1] A method of screening a compound or a salt thereof that changes the binding property of a G protein-coupled receptor protein comprising the same or substantially the same amino acid sequence as the amino acid sequence represented by SEQ ID NO: 1, or a salt thereof, to a ligand peptide comprising the amino acid sequence represented by any one of SEQ ID NO: 3 through SEQ ID NO: 7, its amide, or a salt thereof, or signal transduction, which is characterized by using (1) said receptor protein, its partial peptide, or a salt thereof, and (2) said ligand peptide, its amide, or a salt thereof,

[2] A method of screening an agonist or antagonist to a G protein-coupled receptor protein comprising the same or substantially the same amino acid sequence as the amino acid sequence represented by SEQ ID NO: 1, or a salt thereof, which is characterized by using (1) said receptor protein, or its partial peptide, or a salt thereof, and (2) a compound or a salt thereof that changes the binding property of a ligand peptide comprising the amino acid sequence represented by any one of SEQ ID NO: 3 through SEQ ID NO: 7, its amide, or a salt thereof, to said receptor protein or a salt thereof, or signal transduction;

[3] A kit for screening a compound or a salt thereof that changes the binding property of a G protein-coupled receptor protein comprising the same or substantially the same amino acid sequence as the amino acid sequence represented by SEQ ID NO: 1, or a salt thereof, to a ligand peptide comprising the amino acid sequence represented by any one of SEQ ID NO: 3 through SEQ ID NO: 7, its amide, or a salt thereof, or signal transduction, which is characterized by comprising (1) said receptor protein, its partial peptide, or a salt thereof, and (2) said ligand peptide, its amide, or a salt thereof;

[4] A kit for screening an agonist or antagonist to a G protein-coupled receptor protein comprising the same or substantially the same amino acid sequence as the amino acid sequence represented by SEQ ID NO: 1, or a salt thereof, which is characterized by comprising (1) said receptor protein, or its partial peptide, or a salt thereof, and (2) a compound or a salt thereof that changes the binding property of a ligand peptide comprising the amino acid sequence represented by any one of SEQ ID NO: 3 through SEQ ID NO: 7, its amide, or a salt thereof, to said receptor protein or a salt thereof, or signal transduction;

[5] A compound or a salt thereof that changes the binding property of a ligand peptide comprising the amino acid sequence represented by any one of SEQ ID NO: 3 through SEQ ID NO: 7, its amide, or a salt thereof, to a G protein-coupled receptor protein comprising the same or substantially the same amino acid sequence as the amino acid sequence represented by SEQ ID NO: 1, or a salt thereof, or signal transduction, which is obtainable using the screening method according to [1] or the screening kit according to [3];

[6] The compound or a salt thereof according to [5], which is an agonist for a G protein-coupled receptor protein comprising the same or substantially the same amino acid sequence as the amino acid sequence represented by SEQ ID NO: 1, or a salt thereof;

[7] The compound or a salt thereof according to [5], which is an antagonist to a G protein-coupled receptor protein comprising the same or substantially the same amino acid sequence as the amino acid sequence represented by SEQ ID NO: 1, or a salt thereof;

[8] A pharmaceutical comprising a compound or a salt thereof that changes the binding property of a ligand peptide comprising the amino acid sequence represented by any one of SEQ ID NO: 3 through SEQ ID NO: 7, its amide, or a salt thereof, to a G protein-coupled receptor protein comprising the same or substantially the same amino acid sequence as the amino acid sequence represented by SEQ ID NO: 1, or a salt thereof, or signal transduction;

[9] The pharmaceutical according to [8], which is an agent for preventing/treating asthma, allergic disease, inflammation, inflammatory eye diseases, Addison's disease, autoimmune hemolytic anemia, systemic lupus erythematosus, psoriasis, rheumatism, cerebral hemorrhage, cerebral infarction, head injury, spinal cord injury, cerebral edema, multiple sclerosis, Alzheimer's disease, Parkinson's disease, amyotrophic lateral sclerosis (ALS), AIDS encephalopathy, meningitis, diabetes mellitus, chronic articular rheumatism, arthritis deformans, rheumatoid spondylitis, gouty arthritis, synovitis, toxemia, Crohn's disease, ulcerative colitis, chronic pneumonia, silicosis, pulmonary sarcoidosis, pulmonary tuberculosis, cachexia, arteriosclerosis, Creutzfeldt-Jakob disease, viral infections, angina pectoris, myocardial infarction, congestive heart failure, hepatitis, posttransplantational hyperimmunization, dialysis hypotension, disseminated intravascular coagulation syndrome, immunodeficiency, infections or cancer;

[10] An agent for preventing/treating immunodeficiency, comprising an agonist for a G protein-coupled receptor protein comprising the same or substantially the same amino acid sequence as the amino acid sequence represented by SEQ ID NO: 1, or a salt thereof;

[11] An agent for preventing/treating asthma, allergic disease, inflammation, inflammatory eye diseases, Addison's disease, autoimmune hemolytic anemia, systemic lupus erythematosus, psoriasis, rheumatism, cerebral hemorrhage, cerebral infarction, head injury, spinal cord injury, cerebral edema, multiple sclerosis, Alzheimer's disease, Parkinson's disease, amyotrophic lateral sclerosis (ALS), AIDS encephalopathy, meningitis, diabetes mellitus, chronic articular rheumatism, arthritis deformans, rheumatoid spondylitis, gouty arthritis, synovitis, toxemia, Crohn's disease, ulcerative colitis, chronic pneumonia, silicosis, pulmonary sarcoidosis, pulmonary tuberculosis, cachexia, arteriosclerosis, Creutzfeldt-Jakob disease, viral infections, angina pectoris, myocardial infarction, congestive heart failure, hepatitis, posttransplantational hyperimmunization, dialysis hypotension, disseminated intravascular coagulation syndrome, infections or cancer, which comprises an antagonist to a G protein-coupled receptor protein comprising the same or substantially the same amino acid sequence as the amino acid sequence represented by SEQ ID NO: 1, or a salt thereof;

[12] A method of screening an agonist for a G protein-coupled receptor protein comprising the same or substantially the same amino acid sequence as the amino acid sequence represented by SEQ ID NO: 1, or a salt thereof, which is characterized by assaying an intracellular cAMP production inhibition activity in the case where a test compound is brought in contact with a cell containing said receptor protein;

[13] An agent for preventing/treating asthma, allergic disease, inflammation, inflammatory eye diseases, Addison's disease, autoimmune hemolytic anemia, systemic lupus erythematosus, psoriasis, rheumatism, cerebral hemorrhage, cerebral infarction, head injury, spinal cord injury, cerebral edema, multiple sclerosis, Alzheimer's disease, Parkinson's disease, amyotrophic lateral sclerosis (ALS), AIDS encephalopathy, meningitis, diabetes mellitus, chronic articular rheumatism, arthritis deformans, rheumatoid spondylitis, gouty arthritis, synovitis, toxemia, Crohn's disease, ulcerative colitis, chronic pneumonia, silicosis, pulmonary sarcoidosis, pulmonary tuberculosis, cachexia, arteriosclerosis, Creutzfeldt-Jakob disease, viral infections, angina pectoris, myocardial infarction, congestive heart failure, hepatitis, posttransplantational hyperimmunization, dialysis hypotension, disseminated intravascular coagulation syndrome, immunodeficiency, infections or cancer, which comprises a G protein-coupled receptor protein comprising the same or substantially the same amino acid sequence as the amino acid sequence represented by SEQ ID NO: 1, or a salt thereof;

[14] An agent for preventing/treating asthma, allergic disease, inflammation, inflammatory eye diseases, Addison's disease, autoimmune hemolytic anemia, systemic lupus erythematosus, psoriasis, rheumatism, cerebral hemorrhage, cerebral infarction, head injury, spinal cord injury, cerebral edema, multiple sclerosis, Alzheimer's disease, Parkinson's disease, amyotrophic lateral sclerosis (ALS), AIDS encephalopathy, meningitis, diabetes mellitus, chronic articular rheumatism, arthritis deformans, rheumatoid spondylitis, gouty arthritis, synovitis, toxemia, Crohn's disease, ulcerative colitis, chronic pneumonia, silicosis, pulmonary sarcoidosis, pulmonary tuberculosis, cachexia, arteriosclerosis, Creutzfeldt-Jakob disease, viral infections, angina pectoris, myocardial infarction, congestive heart failure, hepatitis, posttransplantational hyperimmunization, dialysis hypotension, disseminated intravascular coagulation syndrome, immunodeficiency, infections or cancer, which comprises a polynucleotide comprising a polynucleotide encoding a G protein-coupled receptor protein comprising the same or substantially the same amino acid sequence as the amino acid sequence represented by SEQ ID NO: 1, or a partial peptide thereof;

[15] A diagnostic agent for asthma, allergic disease, inflammation, inflammatory eye diseases, Addison's disease, autoimmune hemolytic anemia, systemic lupus erythematosus, psoriasis, rheumatism, cerebral hemorrhage, cerebral infarction, head injury, spinal cord injury, cerebral edema, multiple sclerosis, Alzheimer's disease, Parkinson's disease, amyotrophic lateral sclerosis (ALS), AIDS encephalopathy, meningitis, diabetes mellitus, chronic articular rheumatism, arthritis deformans, rheumatoid spondylitis, gouty arthritis, synovitis, toxemia, Crohn's disease, ulcerative colitis, chronic pneumonia, silicosis, pulmonary sarcoidosis, pulmonary tuberculosis, cachexia, arteriosclerosis, Creutzfeldt-Jakob disease, viral infections, angina pectoris, myocardial infarction, congestive heart failure, hepatitis, posttransplantational hyperimmunization, dialysis hypotension, disseminated intravascular coagulation syndrome, immunodeficiency, infections or cancer, which comprises a polynucleotide comprising a polynucleotide encoding a G protein-coupled receptor protein comprising the same or substantially the same amino acid sequence as the amino acid sequence represented by SEQ ID NO: 1, or a partial peptide thereof;

[16] An agent for preventing/treating asthma, allergic disease, inflammation, inflammatory eye diseases, Addison's disease, autoimmune hemolytic anemia, systemic lupus erythematosus, psoriasis, rheumatism, cerebral hemorrhage, cerebral infarction, head injury, spinal cord injury, cerebral edema, multiple sclerosis, Alzheimer's disease, Parkinson's disease, amyotrophic lateral sclerosis (ALS), AIDS encephalopathy, meningitis, diabetes mellitus, chronic articular rheumatism, arthritis deformans, rheumatoid spondylitis, gouty arthritis, synovitis, toxemia, Crohn's disease, ulcerative colitis, chronic pneumonia, silicosis, pulmonary sarcoidosis, pulmonary tuberculosis, cachexia, arteriosclerosis, Creutzfeldt-Jakob disease, viral infections, angina pectoris, myocardial infarction, congestive heart failure, hepatitis, posttransplantational hyperimmunization, dialysis hypotension, disseminated intravascular coagulation syndrome, immunodeficiency, infections or cancer, which comprises an antibody to a G protein-coupled receptor protein comprising the same or substantially the same amino acid sequence as the amino acid sequence represented by SEQ ID NO: 1, its partial peptide, or a salt thereof;

[17] A diagnostic agent for asthma, allergic disease, inflammation, inflammatory eye diseases, Addison's disease, autoimmune hemolytic anemia, systemic lupus erythematosus, psoriasis, rheumatism, cerebral hemorrhage, cerebral infarction, head injury, spinal cord injury, cerebral edema, multiple sclerosis, Alzheimer's disease, Parkinson's disease, amyotrophic lateral sclerosis (ALS), AIDS encephalopathy, meningitis, diabetes mellitus, chronic articular rheumatism, arthritis deformans, rheumatoid spondylitis, gouty arthritis, synovitis, toxemia, Crohn's disease, ulcerative colitis, chronic pneumonia, silicosis, pulmonary sarcoidosis, pulmonary tuberculosis, cachexia, arteriosclerosis, Creutzfeldt-Jakob disease, viral infections, angina pectoris, myocardial infarction, congestive heart failure, hepatitis, posttransplantational hyperimmunization, dialysis hypotension, disseminated intravascular coagulation syndrome, immunodeficiency, infections or cancer, which comprises an antibody to a G protein-coupled receptor protein comprising the same or substantially the same amino acid sequence as the amino acid sequence represented by SEQ ID NO: 1, its partial peptide, or a salt thereof,

[18] An agent for preventing/treating asthma, allergic disease, inflammation, inflammatory eye diseases, Addison's disease, autoimmune hemolytic anemia, systemic lupus erythematosus, psoriasis, rheumatism, cerebral hemorrhage, cerebral infarction, head injury, spinal cord injury, cerebral edema, multiple sclerosis, Alzheimer's disease, Parkinson's disease, amyotrophic lateral sclerosis (ALS), AIDS encephalopathy, meningitis, diabetes mellitus, chronic articular rheumatism, arthritis deformans, rheumatoid spondylitis, gouty arthritis, synovitis, toxemia, Crohn's disease, ulcerative colitis, chronic pneumonia, silicosis, pulmonary sarcoidosis, pulmonary tuberculosis, cachexia, arteriosclerosis, Creutzfeldt-Jakob disease, viral infections, angina pectoris, myocardial infarction, congestive heart failure, hepatitis, posttransplantational hyperimmunization, dialysis hypotension, disseminated intravascular coagulation syndrome, immunodeficiency, infections or cancer, which comprises the entire or part of a base sequence complementary to a polynucleotide comprising a polynucleotide encoding a G protein-coupled receptor protein comprising the same or substantially the same amino acid sequence as the amino acid sequence represented by SEQ ID NO: 1, or a partial peptide thereof;

[19] A method for preventing/treating asthma, allergic disease, inflammation, inflammatory eye diseases, Addison's disease, autoimmune hemolytic anemia, systemic lupus erythematosus, psoriasis, rheumatism, cerebral hemorrhage, cerebral infarction, head injury, spinal cord injury, cerebral edema, multiple sclerosis, Alzheimer's disease, Parkinson's disease, amyotrophic lateral sclerosis (ALS), AIDS encephalopathy, meningitis, diabetes mellitus, chronic articular rheumatism, arthritis deformans, rheumatoid spondylitis, gouty arthritis, synovitis, toxemia, Crohn's disease, ulcerative colitis, chronic pneumonia, silicosis, pulmonary sarcoidosis, pulmonary tuberculosis, cachexia, arteriosclerosis, Creutzfeldt-Jakob disease, viral infections, angina pectoris, myocardial infarction, congestive heart failure, hepatitis, posttransplantational hyperimmunization, dialysis hypotension, disseminated intravascular coagulation syndrome, immunodeficiency, infections or cancer, which is characterized by administering to a mammal an effective amount of (i) a G protein-coupled receptor protein comprising the same or substantially the same amino acid sequence as the amino acid sequence represented by SEQ ID NO: 1, its partial peptide, or a salt thereof, (ii) a polynucleotide comprising a polynucleotide encoding a G protein-coupled receptor protein comprising the same or substantially the same amino acid sequence as the amino acid sequence represented by SEQ ID NO: 1, or a partial peptide thereof, or (iii) an agonist for a G protein-coupled receptor protein comprising the same or substantially the same amino acid sequence as the amino acid sequence represented by SEQ ID NO: 1, or a salt thereof;

[20] A method for preventing/treating asthma, allergic disease, inflammation, inflammatory eye diseases, Addison's disease, autoimmune hemolytic anemia, systemic lupus erythematosus, psoriasis, rheumatism, cerebral hemorrhage, cerebral infarction, head injury, spinal cord injury, cerebral edema, multiple sclerosis, Alzheimer's disease, Parkinson's disease, amyotrophic lateral sclerosis (ALS), AIDS encephalopathy, meningitis, diabetes mellitus, chronic articular rheumatism, arthritis deformans, rheumatoid spondylitis, gouty arthritis, synovitis, toxemia, Crohn's disease, ulcerative colitis, chronic pneumonia, silicosis, pulmonary sarcoidosis, pulmonary tuberculosis, cachexia, arteriosclerosis, Creutzfeldt-Jakob disease, viral infections, angina pectoris, myocardial infarction, congestive heart failure, hepatitis, posttransplantational hyperimmunization, dialysis hypotension, disseminated intravascular coagulation syndrome, immunodeficiency, infections or cancer, which is characterized by administering to a mammal an effective amount of (i) an antibody to a G protein-coupled receptor protein comprising the same or substantially the same amino acid sequence as the amino acid sequence represented by SEQ ID NO: 1, its partial peptide, or a salt thereof, (ii) a polynucleotide comprising the entire or part of a base sequence complementary to a polynucleotide comprising a polynucleotide encoding a G protein-coupled receptor protein comprising the same or substantially the same amino acid sequence as the amino acid sequence represented by SEQ ID NO: 1, or a partial peptide thereof, or (iii) an antagonist to a G protein-coupled receptor protein comprising the same or substantially the same amino acid sequence as the amino acid sequence represented by SEQ ID NO: 1, or a salt thereof,

[21] Use of (i) a G protein-coupled receptor protein comprising the same or substantially the same amino acid sequence as the amino acid sequence represented by SEQ ID NO: 1, its partial peptide, or a salt thereof, (ii) a polynucleotide comprising a polynucleotide encoding a G protein-coupled receptor protein comprising the same or substantially the same amino acid sequence as the amino acid sequence represented by SEQ ID NO: 1, or a partial peptide thereof, or (iii) an agonist for a G protein-coupled receptor protein comprising the same or substantially the same amino acid sequence as the amino acid sequence represented by SEQ ID NO: 1, or a salt thereof, to manufacture an agent for preventing/treating asthma, allergic disease, inflammation, inflammatory eye diseases, Addison's disease, autoimmune hemolytic anemia, systemic lupus erythematosus, psoriasis, rheumatism, cerebral hemorrhage, cerebral infarction, head injury, spinal cord injury, cerebral edema, multiple sclerosis, Alzheimer's disease, Parkinson's disease, amyotrophic lateral sclerosis (ALS), AIDS encephalopathy, meningitis, diabetes mellitus, chronic articular rheumatism, arthritis deformans, rheumatoid spondylitis, gouty arthritis, synovitis, toxemia, Crohn's disease, ulcerative colitis, chronic pneumonia, silicosis, pulmonary sarcoidosis, pulmonary tuberculosis, cachexia, arteriosclerosis, Creutzfeldt-Jakob disease, viral infections, angina pectoris, myocardial infarction, congestive heart failure, hepatitis, posttransplantational hyperimmunization, dialysis hypotension, disseminated intravascular coagulation syndrome, immunodeficiency, infections or cancer; and,

[22] Use of (i) an antibody to a G protein-coupled receptor protein comprising the same or substantially the same amino acid sequence as the amino acid sequence represented by SEQ ID NO: 1, its partial peptide, or a salt thereof, (ii) a polynucleotide comprising the entire or part of a base sequence complementary to a polynucleotide comprising a polynucleotide encoding a G protein-coupled receptor protein comprising the same or substantially the same amino acid sequence as the amino acid sequence represented by SEQ ID NO: 1, or a partial peptide thereof, or (iii) an antagonist to a G protein-coupled receptor protein comprising the same or substantially the same amino acid sequence as the amino acid sequence represented by SEQ ID NO: 1, or a salt thereof, to manufacture an agent for preventing/treating asthma, allergic disease, inflammation, inflammatory eye diseases, Addison's disease, autoimmune hemolytic anemia, systemic lupus erythematosus, psoriasis, rheumatism, cerebral hemorrhage, cerebral infarction, head injury, spinal cord injury, cerebral edema, multiple sclerosis, Alzheimer's disease, Parkinson's disease, amyotrophic lateral sclerosis (ALS), AIDS encephalopathy, meningitis, diabetes mellitus, chronic articular rheumatism, arthritis deformans, rheumatoid spondylitis, gouty arthritis, synovitis, toxemia, Crohn's disease, ulcerative colitis, chronic pneumonia, silicosis, pulmonary sarcoidosis, pulmonary tuberculosis, cachexia, arteriosclerosis, Creutzfeldt-Jakob disease, viral infections, angina pectoris, myocardial infarction, congestive heart failure, hepatitis, posttransplantational hyperimmunization, dialysis hypotension, disseminated intravascular coagulation syndrome, immunodeficiency, infections or cancer.

The present invention further provides the following features:

[23] The screening method according to [1] or [2], which is characterized by comparing (i) the case where a G protein-coupled receptor protein comprising the same or substantially the same amino acid sequence as the amino acid sequence represented by SEQ ID NO: 1 (hereinafter briefly referred to as FPRL2), its partial peptide, or a salt thereof, is brought in contact with (a) a ligand peptide comprising the amino acid sequence represented by any one of SEQ ID NO: 3 through SEQ ID NO: 7 (hereinafter briefly referred to as a ligand peptide), its amide, or a salt thereof, or (b) a compound or its salt that changes the binding property of the ligand peptide, its amide, or a salt thereof to the receptor protein or a salt thereof (hereinafter briefly referred to as a low molecular synthetic compound) or signal transduction, with (ii) the case where FPRL2, its partial peptide, or a salt thereof is brought in contact with the ligand peptide, its amide or a salt thereof, or the low molecular synthetic compound, and a test compound;

[24] The screening method according to [1] or [2], which is characterized by measuring the binding amount of a labeled form of the labeled ligand peptide, its amide, or a salt thereof, or the low molecular synthetic compound to FPRL2, its partial peptide, or a salt thereof, (i) in the case where the labeled ligand peptide, its amide, or a salt thereof, or low molecular synthetic compound is brought in contact with FPRL2, its partial peptide, or a salt thereof, and (ii) in the case where the labeled ligand peptide, its amide, or a salt thereof, or low molecular synthetic compound and a test compound are brought in contact with FPRL2, its partial peptide, or a salt thereof, and then comparing (i) and (ii);

[25] The screening method according to [1] or [2], which is characterized by measuring the binding amount of a labeled form of ligand peptide, its amide, or a salt thereof or the low molecular synthetic compound, to a cell containing FPRL2 (i) in the case where the labeled ligand peptide, its amide, or a salt thereof, or low molecular synthetic compound is brought in contact with a cell containing FPRL2 and (ii) in the case where the labeled ligand peptide, its amide, or a salt thereof, or low molecular synthetic compound and a test compound are brought in contact with a cell containing FPRL2, and then comparing (i) and (ii);

[26] The screening method according to [1] or [2], which is characterized by measuring the binding amount of a labeled form of ligand peptide, its amide, or a salt thereof or the low molecular synthetic compound, to a membrane fraction of a cell containing FPRL2 (i) in the case where the labeled ligand peptide, its amide, or a salt thereof, or low molecular synthetic compound is brought in contact with a membrane fraction of a cell containing FPRL2 and (ii) in the case where the labeled ligand peptide, its amide, or a salt thereof, or low molecular synthetic compound and a test compound are brought in contact with a membrane fraction of said cell, and then comparing (i) and (ii);

[27] The screening method according to [1] or [2], which is characterized by measuring the binding amount of a labeled form of ligand peptide, its amide, or a salt thereof or the low molecular synthetic compound, to FPRL2 (i) in the case where the labeled ligand peptide, its amide, or a salt thereof, or low molecular synthetic compound is brought in contact with FPRL2 on a cell membrane expressed by culturing a transformant transformed with a recombinant vector bearing a DNA comprising a DNA encoding FPRL2 and (ii) in the case where the labeled ligand peptide, its amide, or a salt thereof, or low molecular synthetic compound and a test compound are brought in contact with FPRL2 expressed on a cell membrane of said transformant, and then comparing (i) and (ii);

[28] The screening method according to [1] or [2], which is characterized by measuring the cell stimulating activity mediated by FPRL2 (i) in the case where a compound or its salt that activates FPRL2 is brought in contact with a cell containing FPRL2 and (ii) in the case where a compound or its salt that activates FPRL2 and a test compound are brought in contact with said cell, and then comparing (i) and (ii);

[29] The screening method according to [1] or [2], which is characterized by measuring the cell stimulating activity mediated by FPRL2, in the case where a compound or its salt that activates FPRL2 is brought in contact with FPRL2 expressed on a cell membrane by culturing a transformant transformed with a recombinant vector bearing a DNA comprising a DNA encoding FPRL2 and in the case where a compound or its salt that activates FPRL2 and a test compound are brought in contact with the cell membrane of said transform ant, and then comparing the activity between the cases;

[30] The screening method according to [28] or [29], wherein the compound that activates FPRL2 is a ligand peptide, its amide, or a salt thereof, or a low molecular synthetic compound;

[31] The screening kit according to [3] or [4], which is characterized by comprising a cell containing FPRL2 or a membrane fraction of the cell;

[32] The screening kit according to [3] or [4], which is characterized by comprising FPRL2 expressed on a cell membrane by culturing a transformant transformed with a recombinant vector bearing a DNA comprising a DNA encoding FPRL2;

[33] An agent for preventing/treating asthma, allergic disease, inflammation, inflammatory eye diseases, Addison's disease, autoimmune hemolytic anemia, systemic lupus erythematosus, psoriasis, rheumatism, cerebral hemorrhage, cerebral infarction, head injury, spinal cord injury, cerebral edema, multiple sclerosis, Alzheimer's disease, Parkinson's disease, amyotrophic lateral sclerosis (ALS), AIDS encephalopathy, meningitis, diabetes mellitus, chronic articular rheumatism, arthritis deformans, rheumatoid spondylitis, gouty arthritis, synovitis, toxemia, Crohn's disease, ulcerative colitis, chronic pneumonia, silicosis, pulmonary sarcoidosis, pulmonary tuberculosis, cachexia, arteriosclerosis, Creutzfeldt-Jakob disease, viral infections, angina pectoris, myocardial infarction, congestive heart failure, hepatitis, posttransplantational hyperimmunization, dialysis hypotension, disseminated intravascular coagulation syndrome, immunodeficiency, infections or cancer, which comprises a ligand peptide, its amide, or a salt thereof;

[34] An agent for preventing/treating asthma, allergic disease, inflammation, inflammatory eye diseases, Addison's disease, autoimmune hemolytic anemia, systemic lupus erythematosus, psoriasis, rheumatism, cerebral hemorrhage, cerebral infarction, head injury, spinal cord injury, cerebral edema, multiple sclerosis, Alzheimer's disease, Parkinson's disease, amyotrophic lateral sclerosis (ALS), AIDS encephalopathy, meningitis, diabetes mellitus, chronic articular rheumatism, arthritis deformans, rheumatoid spondylitis, gouty arthritis, synovitis, toxemia, Crohn's disease, ulcerative colitis, chronic pneumonia, silicosis, pulmonary sarcoidosis, pulmonary tuberculosis, cachexia, arteriosclerosis, Creutzfeldt-Jakob disease, viral infections, angina pectoris, myocardial infarction, congestive heart failure, hepatitis, posttransplantational hyperimmunization, dialysis hypotension, disseminated intravascular coagulation syndrome, immunodeficiency, infections or cancer, which comprises an antibody to a ligand peptide, its amide, or a salt thereof;

[35] A diagnostic agent for asthma, allergic disease, inflammation, inflammatory eye diseases, Addison's disease, autoimmune hemolytic anemia, systemic lupus erythematosus, psoriasis, rheumatism, cerebral hemorrhage, cerebral infarction, head injury, spinal cord injury, cerebral edema, multiple sclerosis, Alzheimer's disease, Parkinson's disease, amyotrophic lateral sclerosis (ALS), AIDS encephalopathy, meningitis, diabetes mellitus, chronic articular rheumatism, arthritis deformans, rheumatoid spondylitis, gouty arthritis, synovitis, toxemia, Crohn's disease, ulcerative colitis, chronic pneumonia, silicosis, pulmonary sarcoidosis, pulmonary tuberculosis, cachexia, arteriosclerosis, Creutzfeldt-Jakob disease, viral infections, angina pectoris, myocardial infarction, congestive heart failure, hepatitis, posttransplantational hyperimmunization, dialysis hypotension, disseminated intravascular coagulation syndrome, immunodeficiency, infections or cancer, which comprises an antibody to a ligand peptide, its amide, or a salt thereof,

[36] An agent for preventing/treating asthma, allergic disease, inflammation, inflammatory eye diseases, Addison's disease, autoimmune hemolytic anemia, systemic lupus erythematosus, psoriasis, rheumatism, cerebral hemorrhage, cerebral infarction, head injury, spinal cord injury, cerebral edema, multiple sclerosis, Alzheimer's disease, Parkinson's disease, amyotrophic lateral sclerosis (ALS), AIDS encephalopathy, meningitis, diabetes mellitus, chronic articular rheumatism, arthritis deformans, rheumatoid spondylitis, gouty arthritis, synovitis, toxemia, Crohn's disease, ulcerative colitis, chronic pneumonia, silicosis, pulmonary sarcoidosis, pulmonary tuberculosis, cachexia, arteriosclerosis, Creutzfeldt-Jakob disease, viral infections, angina pectoris, myocardial infarction, congestive heart failure, hepatitis, posttransplantational hyperimmunization, dialysis hypotension, disseminated intravascular coagulation syndrome, immunodeficiency, infections or cancer, which comprises a compound or its salt that increases the expression level of FPRL2 or a partial peptide thereof;

[37] An agent for preventing/treating asthma, allergic disease, inflammation, inflammatory eye diseases, Addison's disease, autoimmune hemolytic anemia, systemic lupus erythematosus, psoriasis, rheumatism, cerebral hemorrhage, cerebral infarction, head injury, spinal cord injury, cerebral edema, multiple sclerosis, Alzheimer's disease, Parkinson's disease, amyotrophic lateral sclerosis (ALS), AIDS encephalopathy, meningitis, diabetes mellitus, chronic articular rheumatism, arthritis deformans, rheumatoid spondylitis, gouty arthritis, synovitis, toxemia, Crohn's disease, ulcerative colitis, chronic pneumonia, silicosis, pulmonary sarcoidosis, pulmonary tuberculosis, cachexia, arteriosclerosis, Creutzfeldt-Jakob disease, viral infections, angina pectoris, myocardial infarction, congestive heart failure, hepatitis, posttransplantational hyperimmunization, dialysis hypotension, disseminated intravascular coagulation syndrome, immunodeficiency, infections or cancer, which comprises a compound or its salt that decreases the expression level of FPRL2 or a partial peptide thereof;

[38] A method for preventing/treating asthma, allergic disease, inflammation, inflammatory eye diseases, Addison's disease, autoimmune hemolytic anemia, systemic lupus erythematosus, psoriasis, rheumatism, cerebral hemorrhage, cerebral infarction, head injury, spinal cord injury, cerebral edema, multiple sclerosis, Alzheimer's disease, Parkinson's disease, amyotrophic lateral sclerosis (ALS), AIDS encephalopathy, meningitis, diabetes mellitus, chronic articular rheumatism, arthritis deformans, rheumatoid spondylitis, gouty arthritis, synovitis, toxemia, Crohn's disease, ulcerative colitis, chronic pneumonia, silicosis, pulmonary sarcoidosis, pulmonary tuberculosis, cachexia, arteriosclerosis, Creutzfeldt-Jakob disease, viral infections, angina pectoris, myocardial infarction, congestive heart failure, hepatitis, posttransplantational hyperimmunization, dialysis hypotension, disseminated intravascular coagulation syndrome, immunodeficiency, infections or cancer, which is characterized by administering to a mammal an effective amount of (i) a ligand peptide, its amide, or a salt thereof, or (ii) a compound or its salt that increases the expression level of FPRL2 or a partial peptide thereof;

[39] A method for preventing/treating asthma, allergic disease, inflammation, inflammatory eye diseases, Addison's disease, autoimmune hemolytic anemia, systemic lupus erythematosus, psoriasis, rheumatism, cerebral hemorrhage, cerebral infarction, head injury, spinal cord injury, cerebral edema, multiple sclerosis, Alzheimer's disease, Parkinson's disease, amyotrophic lateral sclerosis (ALS), AIDS encephalopathy, meningitis, diabetes mellitus, chronic articular rheumatism, arthritis deformans, rheumatoid spondylitis, gouty arthritis, synovitis, toxemia, Crohn's disease, ulcerative colitis, chronic pneumonia, silicosis, pulmonary sarcoidosis, pulmonary tuberculosis, cachexia, arteriosclerosis, Creutzfeldt-Jakob disease, viral infections, angina pectoris, myocardial infarction, congestive heart failure, hepatitis, posttransplantational hyperimmunization, dialysis hypotension, disseminated intravascular coagulation syndrome, immunodeficiency, infections or cancer, which is characterized by administering to a mammal an effective amount of (i) an antibody to a ligand peptide, its amide, or a salt thereof, or (ii) a compound or its salt that decreases the expression level of FPRL2 or a partial peptide thereof;

[40] Use of (i) a ligand peptide, its amide, or a salt thereof, or (ii) a compound or its salt that increases the expression level of FPRL2 or a partial peptide thereof, to manufacture an agent for preventing/treating asthma, allergic disease, inflammation, inflammatory eye diseases, Addison's disease, autoimmune hemolytic anemia, systemic lupus erythematosus, psoriasis, rheumatism, cerebral hemorrhage, cerebral infarction, head injury, spinal cord injury, cerebral edema, multiple sclerosis, Alzheimer's disease, Parkinson's disease, amyotrophic lateral sclerosis (ALS), AIDS encephalopathy, meningitis, diabetes mellitus, chronic articular rheumatism, arthritis deformans, rheumatoid spondylitis, gouty arthritis, synovitis, toxemia, Crohn's disease, ulcerative colitis, chronic pneumonia, silicosis, pulmonary sarcoidosis, pulmonary tuberculosis, cachexia, arteriosclerosis, Creutzfeldt-Jakob disease, viral infections, angina pectoris, myocardial infarction, congestive heart failure, hepatitis, posttransplantational hyperimmunization, dialysis hypotension, disseminated intravascular coagulation syndrome, immunodeficiency, infections or cancer;

[41] Use of (i) an antibody to a ligand peptide, its amide, or a salt thereof, or (ii) a compound or its salt that decreases the expression level of FPRL2 or a partial peptide thereof, to manufacture an agent for preventing/treating asthma, allergic disease, inflammation, inflammatory eye diseases, Addison's disease, autoimmune hemolytic anemia, systemic lupus erythematosus, psoriasis, rheumatism, cerebral hemorrhage, cerebral infarction, head injury, spinal cord injury, cerebral edema, multiple sclerosis, Alzheimer's disease, Parkinson's disease, amyotrophic lateral sclerosis (ALS), AIDS encephalopathy, meningitis, diabetes mellitus, chronic articular rheumatism, arthritis deformans, rheumatoid spondylitis, gouty arthritis, synovitis, toxemia, Crohn's disease, ulcerative colitis, chronic pneumonia, silicosis, pulmonary sarcoidosis, pulmonary tuberculosis, cachexia, arteriosclerosis, Creutzfeldt-Jakob disease, viral infections, angina pectoris, myocardial infarction, congestive heart failure, hepatitis, posttransplantational hyperimmunization, dialysis hypotension, disseminated intravascular coagulation syndrome, immunodeficiency, infections or cancer;

[42] A method of confirming that a drug for preventing/treating asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as, cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endotoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, immunodeficiency, infections or cancer, binds to said receptor protein or a salt thereof, which comprises using FPRL2;

[43] A method of confirming that an agent for preventing/treating immunodeficiency is an agonist for said receptor protein or a salt thereof, which is characterized by using FPRL2;

[44] A method of confirming that a drug for preventing/treating asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as, cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endotoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, infections or cancer, is an antagonist to said receptor protein or a salt thereof, which is characterized by using FPRL2; and

[45] The screening method according to [42] through [44], which is characterized by measuring the binding amount of each agent to FPRL2, when each drug is brought in contact with FPRL2.

BEST MODE FOR CARRYING OUT THE INVENTION

Figure 1:
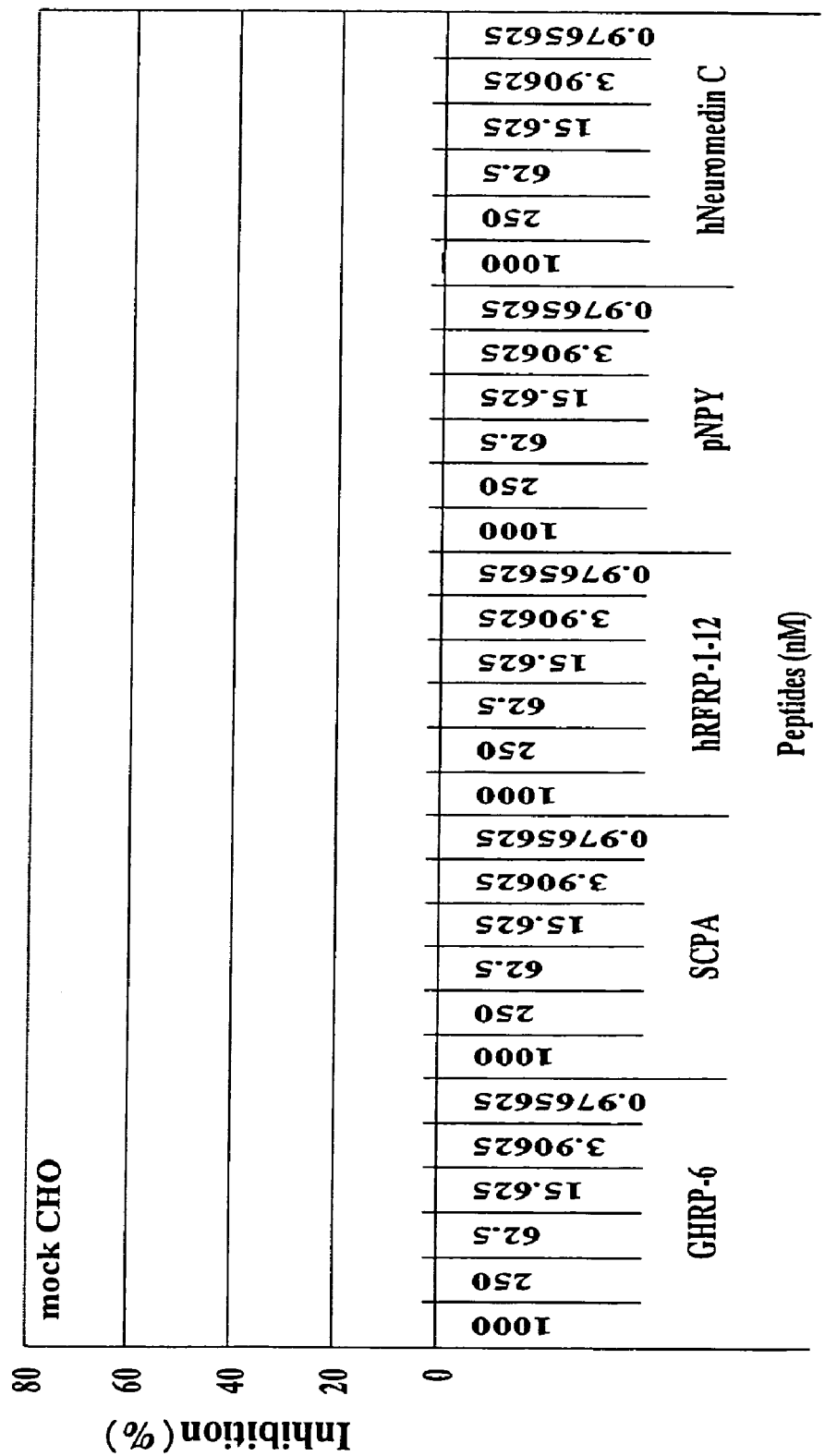
FIG. 1 shows the results obtained by assaying the activity of inhibiting intracellular cAMP production level when various ligand peptides were added to CHO cells in which human FPRL2 was not expressed (mock CHO). "Peptides (nM)" on the abscissa indicates the amounts of various ligand peptides added. "Inhibition (%)" on the ordinate indicates the activity of inhibiting intracellular cAMP production when various ligand peptides were added.

The FPRL2 used in the present invention is a receptor protein comprising the same or substantially the same amino acid sequence as the amino acid sequence represented by SEQ ID NO: 1.

The FPRL2 may be any protein derived from any cells (such as splenocytes, nerve cells, glial cells, β cells of pancreas, bone marrow cells, mesangial cells, Langerhans' cells, epidermic cells, epithelial cells, endothelial cell, fibroblast, fibrocyte, myocyte, fat cell, immune cell (e.g., macrophage, T cell, B cell, natural killer cell, mast cell, neutrophil, basophil, eosinophil, monocyte), megakaryocyte, synovial cell, chondrocyte, bone cell, osteoblast, osteoclast, mammary gland cell, hepatocyte, interstitial cell, etc., or the corresponding precursor cells, stem cells, cancer cells, etc.) or hematocytes; or any tissues where such cells are present, such as brain or any of brain regions (e.g., olfactory bulb, amygdaloid nucleus, basal ganglia, hippocampus, thalamus, subthalamus, subthalamic nucleus, cerebral cortex, medulla oblongata, cerebellum, occipital lobes, frontal lobe, lateral lobe, putamen, caudate nucleus, corpus callosum, substantia nigra), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), intestinal tract, blood vessel, heart, thymus, spleen, submandibular gland, peripheral blood, peripheral blood cells, prostate, testicle, testis, ovary, placenta, uterus, bone, joint, skeletal muscle, etc. of human and mammal (e.g., guinea pig, rat, mouse, rabbit, swine, sheep, bovine, monkey, etc.); especially, a protein derived from immunocompetent organs and immunocompetent cells such as spleen, bone marrow, intestinal tract, monocyte and macrophage, or it may also be a synthetic protein.

Substantially the same amino acid sequence as that represented by SEQ ID NO: 1 includes an amino acid sequence having at least about 85% homology, preferably at least about 90% homology, more preferably at least about 95% homology, to the amino acid sequence represented by SEQ ID NO: 1.

As the protein of the present invention comprising substantially the same amino acid sequence as the amino acid sequence represented by SEQ ID NO: 1, preferred is the protein having substantially the same amino acid sequence as the amino acid sequence represented by SEQ ID NO: 1 and having the activity substantially equivalent to that of the FPRL2 consisting of the amino acid sequence represented by SEQ ID NO: 1, etc.

Homology of the amino acid sequences can be calculated under the following conditions (Expect Value=10; gaps are allowed; matrix=BLOSUM62; filtering=OFF) using a homology scoring algorithm NCBI BLAST (National Center for Biotechnology Information Basic Local Alignment Search Tool).

The substantially equivalent activity includes, for example, a ligand binding activity, a signal transduction activity, and the like. The "substantially equivalent" is used to mean that these activities are equivalent in terms of quality. Thus, the activities such as a ligand binding activity, a signal transduction activity, etc. are preferably equivalent (e.g., about 0.01 to 100 times, preferably about 0.5 to 20 times, more preferably 0.5 to 2 times), but differences in degree such as a level of these activities, quantitative factors such as a molecular weight of the protein may be present and allowable.

The activities such as a ligand binding activity, a signal transduction activity, etc. can be determined according to publicly known methods with some modifications thereof, for example, by the screening methods that will be later described.

Also, proteins comprising the following amino acid sequences are used as FPRL2: a) the amino acid sequence represented by SEQ ID NO: 1, SEQ ID NO: 4 or SEQ ID NO: 6, of which at least 1 or 2 (preferably approximately 1 to 30, more preferably approximately 1 to 10, most preferably several (1 to 5)) amino acids are deleted; b) the amino acid sequence represented by SEQ ID NO: 1, SEQ ID NO: 4 or SEQ ID NO: 6, to which at least 1 or 2 (preferably approximately 1 to 30, more preferably approximately 1 to 10, most preferably several (1 to 5)) amino acids are added; c) the amino acid sequence represented by SEQ ID NO: 1, SEQ ID NO: 4 or SEQ ID NO: 6, in which at least 1 or 2 (preferably approximately 1 to 30, more preferably approximately 1 to 10, most preferably several (1 to 5)) amino acids are substituted with other amino acids; or d) a combination of these amino acid sequences described above; and the like.

Throughout the present specification, the FPRL2 is represented in accordance with a conventional way of describing proteins, that is, the N-terminus (amino terminus) at the left hand and the C-terminus (carboxyl terminus) at the right hand. In the FPRL2 including FPRL2 comprising the amino acid sequence represented by SEQ ID NO: 1, the C-terminus may be in any form of a carboxyl group (—COOH), a carboxylate (—COO$^-$), an amide (—CONH$_2$) and an ester (—COOR).

Herein, examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl group such as a phenyl-$C_{1-2}$ alkyl group, e.g., benzyl, phenethyl, etc., or an α-naphthyl-$C_{1-2}$-alkyl group such as α-naphthylmethyl, etc.; and the like. In addition, pivaloyloxymethyl or the like, which is used widely as an ester for oral administration, may also be used.

Where the FPRL2 contains a carboxyl group (or a carboxylate) at a position other than the C-terminus, it may be amidated or esterified and such an amide or ester is also included within the FPRL2 of the present invention. The ester group may be the same group as that described with respect to the C-terminus described above.

Furthermore, examples of the FPRL2 include variants of the above proteins, wherein the amino group at the N-terminal methionine residue of the protein supra is protected with a protecting group (for example, a $C_{1-6}$ acyl group such as a $C_{2-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{2-6}$ alkanoyl group, e.g., formyl group, acetyl group, etc.), or conjugated proteins such as glycoproteins bound to sugar chains.

As a specific example of the FPRL2 of the present invention, for example, human-derived FPRL2 consisting of the amino acid sequence represented by SEQ ID NO: 1 (Genomics 13 (2), 437-440 (1992)) is used.

The partial peptides of the FPRL2 (hereinafter sometimes briefly referred to as the "partial peptide") may be any partial peptides of FPRL2; in the protein molecules of FPRL2, there may be employed, e.g., those having the site exposed outside cell membranes and having a substantially equivalent receptor binding activity, and the like.

Specific examples of the partial peptide of the FPRL2 having the amino acid sequence represented by SEQ ID NO: 1 include peptides containing the part analyzed to be an extracellular domain (hydrophilic domain) in the hydrophobic plotting analysis. A peptide containing a hydrophobic domain in part can be used as well. In addition, a peptide containing each domain separately as well as a peptide containing plural domains together may also be employed.

In the partial peptides of the present invention, the number of amino acids is at least 20, preferably at least 50 and more preferably at least 100, in the amino acid sequence, which constitutes the receptor protein of the present invention described above; such peptides, etc. are preferred.

The term substantially the same amino acid sequence is used to mean an amino acid sequence having at least about 85% homology, preferably at least about 90% homology, more preferably at least about 95% homology, to these amino acid sequences.

Homology in the amino acid sequences can be calculated under the same conditions using the same homology scoring algorithm NCBI BLAST as described above.

Herein, the term "substantially equivalent receptor activity" is intended to mean the same significance as defined above. The "substantially equivalent receptor activity" can be assayed in a similar manner to the aforementioned.

In addition, the partial peptide of the present invention may contain amino acid sequences, of which at least 1 or 2 amino acids (preferably approximately 1 to 10 amino acids, more preferably several (1 to 5) amino acids) are deleted; to which at least 1 or 2 amino acids (preferably approximately 1 to 20 amino acids, more preferably approximately 1 to 10 amino acids, and most preferably several (1 to 5) amino acids) are added; or, in which at least 1 or 2 amino acids (preferably approximately 1 to 10 amino acids, more preferably several and most preferably approximately 1 to 5 amino acids) are substituted with other amino acids.

Further, in the partial peptide of the present invention, the C-terminal may be a carboxyl group (—COOH), a carboxylate (—COO$^-$), an amide (—CONH$_2$) or an ester (—COOR). When the partial peptide of the present invention contains a carboxyl group (or a carboxylate) at the site other than the C-terminus, the carboxyl group may be amidated or esterified and those amides or esters are also included in the partial peptide of the present invention. As the esters in this case, for example, the C-terminal esters described above may be employed.

Furthermore, as in the FPRL2 described above, the partial peptide of the present invention includes those in which the amino group of the N-terminal methionine residue is protected by a protecting group, those in which the N-terminal residue is cleaved in vivo and the produced Gln is pyroglutamated, those in which substituents on the side chains of amino acids in the molecule are protected by appropriate protecting groups, conjugated peptides such as those, to which sugar chains are coupled, i.e., so-called glycopeptides, and the like.

For salts of the FPRL2 of the present invention or its partial peptide, there are employed physiologically acceptable salts with acids or bases, particularly preferred are physiologically acceptable acid addition salts. Examples of such salts are salts with inorganic acids (e.g., hydrochloric acid, phosphoric acid, hydrobromic acid or sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid or benzenesulfonic acid), and the like.

The FPRL2 of the present invention or its salts may be manufactured by publicly known methods used to purify receptor proteins from the human or non-human mammal cells or tissues described above, or may also be manufactured by culturing transformants bearing DNAs encoding the FPRL2 of the present invention later described. Alternatively, the FPRL2 of the present invention or its salts may also be manufactured by the protein synthesis methods later described or by its modification.

Where the FPRL2 is manufactured from human or non-human mammal tissues or cells, the human or non-human mammal tissues or cells are homogenized and then extracted with an acid, etc. The FPRL2 is isolated and purified from the obtained extract by a combination of chromatography techniques such as reversed phase chromatography, ion exchange chromatography, and the like.

To synthesize the FPRL2 of the present invention or its partial peptide, or salts or amides thereof, commercially available resins that are normally used for the protein synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2',4'-dimethoxyphenyl-hydroxymethyl)phenoxy resin, 4-(2',4'-dimethoxyphenyl-Fmoc-aminoethyl)phenoxy resin, etc. Using these resins, amino acids in which α-amino groups and functional groups on the side chains are appropriately protected are condensed on the resin in the order of the sequence of the objective protein according to various condensation methods publicly known. At the end of the reaction, the protein is excised from the resin and at the same time, the protecting groups are removed. Then, intramolecular disulfide bond-forming reaction is performed in a highly diluted solution to obtain the objective protein or amides thereof.

For condensation of the protected amino acids described above, a variety of activation reagents available for the protein synthesis may be used, and carbodiimides are particularly preferably employed. Examples of such carbodiimides include DCC, N,N'-diisopropylcarbodiimide, N-ethyl-N'-(3-dimethylaminopropyl)carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents used to activate the protected amino acids or condense with the resin may be chosen from solvents that are known to be usable for protein condensation reactions. For example, there may be employed acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxan, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to protein binding forming reactions and is usually selected in the range of approximately −20° C. to 50° C. The activated amino acid derivatives are used generally in an excess of 1.5 to 4 times. The condensation is examined using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole.

Examples of the protecting groups used to protect the starting amino groups include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower alkanoyl group, such as acetyl group, an aroyl group such as benzoyl group, and a group derived from carbonic acid such as benzyloxycarbonyl group and ethoxycarbonyl group. Examples of a group appropriately used for the etherification include benzyl group, tetrahydropyranyl group, t-butyl group, etc.

Examples of groups for protecting the phenolic hydroxyl group of tyrosine include Bzl, Cl$_2$-Bzl, 2-nitrobenzyl, Br-Z, tertiary butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting materials include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)].

As the activated amino acids in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethanesulfonic acid or trifluoroacetic acid, or a mixture solution of these acids; a treatment with a base such as diisopropylethylamine, triethylamine, piperidine or piperazine; and reduction with sodium in liquid ammonia. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol or 1,2-ethanedithiol. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol or 1,4-butanedithiol, as well as by a treatment with an alkali such as a dilute sodium hydroxide solution and dilute ammonia, etc.

Protection of functional groups that should not be involved in the reaction of the starting materials, protecting groups, elimination of the protecting groups and activation of functional groups involved in the reaction may be appropriately selected from publicly known groups and publicly known means.

In another method for obtaining the amides of the protein, for example, the α-carboxyl group of the carboxy terminal amino acid is first protected by amidation; the peptide (protein) chain is then extended to amino group for a desired length. Thereafter, a protein in which only the protecting group of the N-terminal α-amino group has been eliminated from the peptide chain and a protein in which only the protecting group of the C-terminal carboxyl group has been eliminated are manufactured. The two proteins are condensed in a mixture of the solvents described above. The details of the condensation reaction are the same as described above. After the protected protein obtained by the condensation is purified, all the protecting groups are eliminated by the method described above to give the desired crude protein. This crude protein is purified by various known purification means. Lyophilization of the major fraction gives the amide of the desired protein.

To prepare the esterified protein, for example, the α-carboxyl group of the carboxy terminal amino acid is condensed with a desired alcohol to prepare the amino acid ester, which is followed by procedure similar to the preparation of the amidated protein above to give the desired esterified protein.

The partial peptide of the FPRL2 of the present invention or its salt can be manufactured by publicly known methods for peptide synthesis or by cleaving the FPRL2 of the present invention with an appropriate peptidase. For methods of peptide synthesis, for example, either solid phase synthesis or liquid phase synthesis may be used. That is, the partial peptide or amino acids which can constitute the FPRL2 of the present invention can be condensed with the remaining part. Where the product contains protecting groups, these protecting groups are removed to give the desired peptide. Publicly known methods for condensation and elimination of the protecting groups are described in a) to e) below.

a) M. Bodanszky & M. A. Ondetti: Peptide Synthesis, Interscience Publishers, New York (1966)

b) Schroeder & Luebke: The Peptide, Academic Press, New York (1965)

c) Nobuo Izumiya, et al.: *Peptide Gosei-no-Kiso to Jikken* (Basics and experiments of peptide synthesis), published by Maruzen Co. (1975)

d) Haruaki Yajima & Shunpei Sakakibara: *Seikagaku Jikken Koza* (Biochemical Experiment) 1, *Tanpakushitsu no Kagaku* (Chemistry of Proteins) IV, 205 (1977)

e) Haruaki Yajima ed.: *Zoku Iyakuhin no Kaihatsu* (A sequel to Development of Pharmaceuticals), Vol. 14, Peptide Synthesis, published by Hirokawa Shoten After completion of the reaction, the partial peptide of the present invention can be purified and isolated by a combination of conventional purification methods such as solvent extraction, distillation, column chromatography, liquid chromatography and recrystallization. When the partial peptide obtained by the above methods is in a free form, partial peptide can be converted into an appropriate salt by a publicly known method; when partial peptide is obtained in a salt form, it can be converted into a free form by a publicly known method.

The polynucleotide encoding the FPRL2 of the present invention may be any polynucleotide so long as it contains the base sequence (DNA or RNA, preferably DNA) encoding the FPRL2 of the present invention described above. Such a polynucleotide may also be any one of DNAs encoding the FPRL2 of the present invention, RNAs such as mRNA, etc., and may be double-stranded or single-stranded. Where the polynucleotide is double-stranded, it may be double-stranded DNA, double-stranded RNA or DNA:RNA hybrid. Where the polynucleotide is single-stranded, it may be a sense strand (i.e., a coding strand) or an antisense strand (i.e., a non-coding strand).

Using the polynucleotide encoding the FPRL2 of the present invention, mRNA of the FPRL2 of the present invention can be quantified by, for example, the publicly known method published in separate volume of *Jikken Igaku* 15 (7) "New PCR and its application" (1997), or by its modifications.

The DNA encoding the FPRL2 of the present invention may be any one of genomic DNA, genomic DNA library, cDNA derived from the cells and tissues described above, cDNA library derived from the cells and tissues described above and synthetic DNA. The vector to be used for the library may be any of bacteriophage, plasmid, cosmid and phagemid. The DNA may also be directly amplified by reverse transcriptase polymerase chain reaction (hereinafter abbreviated as RT-PCR) using the total RNA or mRNA fraction prepared from the cells and tissues described above.

Specifically, the DNA encoding human FPRL2 of the present invention may be any DNA, so long as it is, for example, a DNA containing the base sequence represented by SEQ ID NO: 2, or any DNA having a base sequence hybridizable to the base sequence represented by SEQ ID NO: 2 under high stringent conditions and encoding a receptor protein which has the activities substantially equivalent to those of human FPRL2 consisting of the amino acid sequence represented by SEQ ID NO: 1 (e.g., a ligand-binding activity, a signal transduction activity, etc.).

Examples of the DNA that is hybridizable to the base sequence represented by SEQ ID NO: 2 include a DNA comprising the base sequence having at least about 85% homology, preferably at least about 90% homology and more preferably at least about 95% homology, to the base sequence represented by SEQ ID NO: 2.

Homology of the base sequences can be measured under the following conditions (Expectation value=10; gaps are allowed; filtering=ON; match score=1; mismatch score=−3) using a homology scoring algorithm NCBI BLAST (National Center for Biotechnology Information Basic Local Alignment Search Tool).

Hybridization can be carried out by publicly known methods or by a modification thereof, for example, according to the method described in Molecular Cloning, 2nd. (J. Sambrook et al., Cold Spring Harbor Lab. Press, 1989), etc. When a commercially available library is used, hybridization may be carried out according to the instructions of the attached manufacturer's protocol. The hybridization can be carried out preferably under high stringent conditions.

The high stringent conditions used herein are, for example, those in a sodium concentration at about 19 to 40 mM, preferably about 19 to 20 mM at a temperature of about 50 to 70° C., preferably about 60 to 65° C. In particular, hybridization conditions in a sodium concentration at about 19 mM at a temperature of about 65° C. are most preferred.

More specifically, the DNA encoding human FPRL2 consisting of the amino acid sequence represented by SEQ ID NO: 1 includes a DNA consisting of the base sequence represented by SEQ ID NO: 2, etc.

The term polynucleotide comprising a part of the base sequence of the DNA encoding the FPRL2 of the present invention or a part of the base sequence complementary to the DNA is used to mean that the polynucleotide embraces not only the DNA encoding the partial peptide of the present invention described below but also RNA.

According to the present invention, antisense polynucleotides (nucleic acids) that can inhibit replication or expression of the FPRL2 gene can be designed and synthesized, on the basis of base sequence information of a DNA encoding the cloned or sequenced FPRL2. Such polynucleotides (nucleic acids) can hybridize to RNA of the FPRL2 gene and inhibit the synthesis or function of the RNA, or can regulate/control the expression of the FPRL2 gene via interaction with RNAs associated with the FPRL2. Polynucleotides complementary to the specified sequences of RNAs associated with the FPRL2 and polynucleotides that can specifically hybridize to RNAs associated with the FPRL2 are useful for regulating/controlling expression of the FPRL2 gene in vivo and in vitro, and are also useful for the treatment or diagnosis of diseases. The term "correspond" is used to mean homologous or complementary to a specific sequence of nucleotides including genes, base sequences or nucleic acids. As between nucleotides, base sequences or nucleic acids and peptides (proteins), the term "corresponding" usually refers to amino acids of a peptide (proteins) that is instructed to be derived from the sequence of nucleotides (nucleic acids) or its complements. The 5' end hairpin loop, 5' end 6-base-pair repeats, 5' end untranslated region, polypeptide translation initiation codon, protein coding region, ORF translation initiation codon, 3' untranslated region, 3' end palindrome region, and 3' end hairpin loop of the FPRL2 gene may be selected as preferred target regions, though any region may be a target within genes for the FPRL2.

The relationship between the targeted nucleic acids and the polynucleotides complementary to at least a portion of the target region, specifically the relationship between the target and the polynucleotides hybridizable to the target, is denoted to be in "antisense". The antisense polynucleotides may be polydeoxynucleotides containing 2-deoxy-D-ribose, polydeoxynucleotides containing D-ribose, any other type of polynucleotides which are N-glycosides of a purine or pyrimidine base, other polymers containing non-nucleotide backbones (e.g., protein nucleic acids and synthetic sequence-specific nucleic acid polymers that are commercially available), other polymers containing nonstandard linkages (provided that the polymers contain nucleotides with such a configuration that allows base pairing or base stacking, as is found in DNAs or RNAs), etc. The antisense polynucleotides may be a double-stranded DNA, a single-stranded DNA, a double-stranded RNA, a single-stranded RNA and also a DNA:RNA hybrid, and further includes unmodified polynucleotides (or unmodified oligonucleotides), those with publicly known types of modifications, for example, those with labels known in the art, those with caps, methylated polynucleotides, those with substitution of one or more naturally occurring nucleotides with their analogue, those with intramolecular modifications of nucleotides such as those with uncharged linkages (e.g., methyl phosphonates, phosphotriesters, phosphoramidates, carbamates, etc.) and those with charged linkages or sulfur-containing linkages (e.g., phosphorothioates, phosphorodithioates, etc.), those having side chain groups such as proteins (including nucleases, nuclease inhibitors, toxins, antibodies, signal peptides, poly-L-lysine, etc.), saccharides (e.g., monosaccharides, etc.), etc., those with intercalators (e.g., acridine, psoralen, etc.), those containing chelators (e.g., metals, radioactive metals, boron, oxidative metals, etc.), those containing alkylating agents, those with modified linkages (e.g., α anomeric nucleic acids, etc.). Herein, the terms "nucleoside", "nucleotide" and "nucleic acid" are used to refer to moieties that contain not only the purine and pyrimidine bases, but also other heterocyclic bases, which have been modified. Such modifications include methylated purines and pyrimidines, acylated purines and pyrimidines and other heterocyclic rings. Modified nucleotides and modified nucleotides also include modifications on the sugar moiety, for example, wherein one or more hydroxyl groups may optionally be replaced with a halogen, aliphatic groups, or may be converted into the corresponding functional groups such as ethers, amines, or the like.

The antisense polynucleotide (nucleic acid) of the present invention is RNA, DNA or a modified nucleic acid (RNA, DNA). Specific examples of the modified nucleic acid are, but not limited to, sulfurized and thiophosphate derivatives of nucleic acids and those resistant to degradation of polynucleoside amides or oligonucleoside amides The antisense nucleic acids of the present invention can be modified preferably based on the following design, that is, by increasing the intracellular stability of the antisense nucleic acid, increasing the cellular permeability of the antisense nucleic acid, increasing the affinity of the nucleic acid to the target sense strand to a higher level, or minimizing the toxicity, if any, of the antisense nucleic acid.

Many such modifications are known in the art, as disclosed in J. Kawakami, et al., Pharm. Tech. Japan, Vol. 8, pp. 247, 1992; Vol. 8, pp. 395, 1992; S. T. Crooke et al. ed., Antisense Research and Applications, CRC Press, 1993; etc.

The antisense nucleic acid of the present invention may contain altered or modified sugars, bases or linkages. The antisense nucleic acid may also be provided in a specialized form such as liposomes, microspheres or may be applied to gene therapy or may be provided in combination with attached moieties. Such attached moieties include polycations such as polylysine that act as charge neutralizers of the phosphate backbone, or hydrophobic moieties such as lipids (e.g., phospholipids, cholesterols, etc.) that potentiate the interaction with cell membranes or increase uptake of the nucleic acid. Preferred examples of the lipids to be attached are cholesterols or derivatives thereof (e.g., cholesteryl chloroformate, cholic acid, etc.). These moieties may be attached at the 3' or 5' ends of the nucleic acid and may be also attached through a base, sugar, or intramolecular nucleoside linkage Other moieties may be capping groups specifically placed at the 3' or 5' ends of the nucleic acid to prevent degradation by nuclease such as exonuclease, RNase, etc. Such capping groups include, but are not limited to, hydroxyl protecting groups known in the art, including glycols such as polyethylene glycol, tetraethylene glycol, and the like.

The inhibitory activity of the antisense nucleic acid can be examined using the transformant of the present invention, the gene expression system of the present invention in vitro or in vivo, or the translation system of G-protein coupled receptor proteins in vivo and in vitro. The nucleic acid can be applied to cells by a variety of publicly known methods.

The DNA encoding the partial peptide of the present invention may be any DNA, so long as it contains the base sequence encoding the partial peptide of the present invention described above. The DNA may also be any of genomic DNA, genomic DNA library, cDNA derived from the cells and tissues described above, cDNA library derived from the cells and tissues described above and synthetic DNA. The vector to be used for the library may be any of bacteriophage, plasmid, cosmid, phagemid and the like. In addition, the DNA can be directly amplified by reverse transcriptase polymerase chain reaction (hereinafter abbreviated as RT-PCR) with the mRNA fraction prepared from the cells or tissues described above.

Specifically, the DNA encoding the partial peptide of the present invention includes, for example, (1) a DNA that has a part of the base sequence of DNA having the base sequence represented by SEQ ID NO: 2, or (2) a DNA having a base sequence hybridizable to the base sequence represented by SEQ ID NO: 2, under high stringent conditions and having a part of the base sequence of DNA encoding a receptor protein having substantially the same activity (e.g., a ligand binding activity, a signal transduction activity, etc.) as FPRL2 consisting of the amino acid sequence represented by SEQ ID NO: 1.

Examples of the DNA that is hybridizable to the base sequence represented by SEQ ID NO: 2 include a DNA sequence comprising the base sequence having at least about 85% homology, preferably at least about 90% homology, and more preferably at least about 95% homology, to the base sequence represented by SEQ ID NO: 2.

Homology in the base sequence can be measured under the same conditions using the same homology scoring algorithm NCBI BLAST described above.

The method and conditions for the hybridization are the same as in the described above.

For cloning of the DNA that completely encodes the FPRL2 of the present invention or its partial peptide (hereinafter, sometimes briefly referred to as the FPRL2 of the present invention), the DNA may be either amplified by PCR using synthetic DNA primers containing a part of the base sequence of the FPRL2 of the present invention, or the DNA inserted into an appropriate vector can be selected by hybridization with a labeled DNA fragment or synthetic DNA that encodes a part or the entire region of the FPRL2 of the present invention. The hybridization can be carried out, for example, according to the method described in Molecular Cloning, 2nd. (J. Sambrook et al., Cold Spring Harbor Lab. Press, 1989). Where commercially available library is used, the hybridization may also be performed in accordance with the protocol described in the attached instructions.

Conversion of the DNA base sequence can be effected by PCR or publicly known methods such as the ODA-LA PCR method, the Gapped duplex method or the Kunkel method, or modifications thereof, by using publicly known kits available as Mutan™-super Express Km (TaKaRa Shuzo Co., Ltd.) or Mutan™-K (TaKaRa Shuzo Co., Ltd.), etc.

The cloned DNA encoding the FPRL2 can be used as it is, depending upon purpose or, if desired, after digestion with a restriction enzyme or after addition of a linker thereto. The DNA may contain ATG as a translation initiation codon at the 5' end thereof and TAA, TGA or TAG as a translation termination codon at the 3' end thereof. These translation initiation and termination codons may also be added by using an appropriate synthetic DNA adapter.

The expression vector for the FPRL2 of the present invention can be manufactured, for example, by (a) excising the desired DNA fragment from the DNA encoding the FPRL2 of the present invention, (b) and then ligating the DNA fragment with an appropriate expression vector downstream a promoter in the vector.

Examples of the vector include plasmids derived form *E. coli* (e.g., pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CMV, pRc/RSV, pcDNAI/Neo, etc.

The promoter used in the present invention may be any promoter if it matches well with a host to be used for gene expression. In the case of using animal cells as the host, examples of the promoter include SRα promoter, SV40 promoter, HIV-LTR promoter, CMV promoter, HSV-TK promoter, etc.

Among them, CMV promoter, SRα promoter or the like is preferably used. Where the host is bacteria of the genus *Escherichia*, preferred examples of the promoter include trp promoter, lac promoter, recA promoter, $\lambda P_L$ promoter, lpp promoter, etc. In the case of using bacteria of the genus *Bacillus* as the host, preferred example of the promoter are SPO1 promoter, SPO2 promoter, penP promoter, etc. When yeast is used as the host, preferred examples of the promoter are PHO5 promoter, PGK promoter, GAP promoter, ADH promoter, etc. When insect cells are used as the host, preferred examples of the promoter include polyhedrin promoter, P10 promoter, etc.

In addition to the foregoing examples, the expression vector may further optionally contain an enhancer, a splicing signal, a poly A addition signal, a selection marker, SV40 replication origin (hereinafter sometimes abbreviated as SV40ori), etc. Examples of the selection marker include dihydrofolate reductase (hereinafter sometimes abbreviated as dhfr) gene [methotrexate (MTX) resistance], ampicillin resistant gene (hereinafter sometimes abbreviated as Amp$^r$), neomycin resistant gene (hereinafter sometimes abbreviated as Neo$^r$, G418 resistance), etc. In particular, when dhfr gene is used as the selection marker together with CHO (dhfr$^-$) cell, the objective gene may be selected also on thymidine free media.

If necessary, a signal sequence that matches with a host is added to the N-terminal side of the protein of the present invention. Examples of the signal sequence that can be used are Pho A signal sequence, OmpA signal sequence, etc. in the case of using bacteria of the genus *Escherichia* as the host; α-amylase signal sequence, subtilisin signal sequence, etc. in the case of using bacteria of the genus *Bacillus* as the host; MFα signal sequence, SUC2 signal sequence, etc. in the case of using yeast as the host; and insulin signal sequence, α-interferon signal sequence, antibody molecule signal sequence, etc. in the case of using animal cells as the host, respectively.

Using the vector bearing the DNA encoding the FPRL2 of the present invention thus constructed, transformants can be manufactured.

Examples of the host, which may be employed, are bacteria belonging to the genus *Escherichia*, bacteria belonging to the genus *Bacillus*, yeast, insect cells, insects, animal cells, and the like.

Specific examples of the bacteria belonging to the genus *Escherichia* include *Escherichia coli* K12 DH1 [Proc. Natl. Acad. Sci. U.S.A., 60, 160 (1968)], JM103 [Nucleic Acids Research, 9, 309 (1981)], JA221 [Journal of Molecular Biology, 120, 517 (1978)], HB101 [Journal of Molecular Biology, 41, 459 (1969)], C600 [Genetics, 39, 440 (1954)], etc.

Examples of the bacteria belonging to the genus *Bacillus* include *Bacillus subtilis* MI114 [Gene, 24, 255 (1983)], 207-21 [Journal of Biochemistry, 95, 87 (1984)], etc.

Examples of yeast include *Saccharomyces cereviseae* AH22, AH22R$^-$, NA87-11 A, DKD-5D, 20B-12, *Schizosaccharomyces pombe* NCYC 1913, NCYC2036, *Pichia pastoris*, etc.

Examples of insect cells include, for the virus AcNPV, *Spodoptera frugiperda* cell (Sf cell), MG1 cell derived from mid-intestine of *Trichoplusia ni*, High Five™ cell derived from egg of *Trichoplusia ni*, cells derived from *Mamestra brassicae*, cells derived from *Estigmena acrea*, etc.; and for the virus BmNPV, *Bombyx mori* N cell (BmN cell), etc. is used. Examples of the Sf cell which can be used are Sf9 cell (ATCC CRL1711) and Sf21 cell (both cells are described in Vaughn, J. L. et al., In vivo, 13, 213-217 (1977).

As the insect, for example, a larva of *Bombyx mori* can be used (Maeda et al., Nature, 315, 592 (1985)).

Examples of animal cells include monkey cell COS-7, Vero, Chinese hamster cell CHO (hereinafter referred to as CHO cell), dhfr gene deficient Chinese hamster cell CHO (hereinafter simply referred to as CHO(dhfr$^-$) cell), mouse L cell, mouse AtT-20, mouse myeloma cell, rat GH 3, human FL cell, etc.

Bacteria belonging to the genus *Escherichia* can be transformed, for example, by the method described in Proc. Natl. Acad. Sci. U.S.A., 69, 2110 (1972), Gene, 17, 107 (1982), etc.

Bacteria belonging to the genus *Bacillus* can be transformed, for example, by the method described in Molecular & General Genetics, 168, 111 (1979), etc.

Yeast can be transformed, for example, by the method described in Methods in Enzymology, 194, 182-187 (1991), Proc. Natl. Acad. Sci. U.S.A., 75, 1929 (1978), etc.

Insect cells or insects can be transformed, for example, according to the method described in Bio/Technology, 6, 47-55(1988), etc.

Animal cells can be transformed, for example, according to the method described in *Saibo Kogaku* (Cell Engineering), extra issue 8, *Shin Saibo Kogaku Jikken Protocol* (New Cell Engineering Experimental Protocol), 263-267 (1995), published by Shujunsha, or Virology, 52, 456 (1973).

Thus, the transformant transformed with the expression vector containing the DNA encoding the FPRL2 can be obtained.

Where the host is bacteria belonging to the genus *Escherichia* or the genus *Bacillus*, the transformant can be appropriately cultured in a liquid medium which contains materials required for growth of the transformant such as carbon sources, nitrogen sources, inorganic materials, etc. Examples of the carbon sources include glucose, dextrin, soluble starch, sucrose, etc. Examples of the nitrogen sources include inorganic or organic materials such as ammonium salts, nitrate salts, corn steep liquor, peptone, casein, meat extract, soybean cake, potato extract, etc. Examples of the inorganic materials are calcium chloride, sodium dihydrogenphosphate, magnesium chloride, etc. In addition, yeast extracts, vitamins, growth promoting factors etc. may also be added to the medium. Preferably, pH of the medium is adjusted to about 5 to about 8.

A preferred example of the medium for culturing the bacteria belonging to the genus *Escherichia* is M9 medium supplemented with glucose and Casamino acids [Miller, Journal of Experiments in Molecular Genetics, 431-433, Cold Spring Harbor Laboratory, New York, 1972]. If necessary, a chemical such as 3β-indolylacrylic acid can be added to the medium thereby to activate the promoter efficiently.

Where the bacteria belonging to the genus *Escherichia* are used as the host, the transformant is usually cultivated at approximately 15 to 43° C. for about 3 hours to about 24 hours. If necessary, the culture may further be aerated or agitated.

Where the bacteria belonging to the genus *Bacillus* are used as the host, the transformant is cultivated generally at approximately 30 to 40° C. for about 6 hours to about 24 hours. If necessary, the culture can be aerated or agitated.

Where yeast is used as the host, the transformant is cultivated, for example, in Burkholder's minimal medium [Bostian, K. L. et al., Proc. Natl. Acad. Sci. U.S.A., 77, 4505 (1980)] or in SD medium supplemented with 0.5% Casamino acids [Bitter, G. A. et al., Proc. Natl. Acad. Sci. U.S.A., 81, 5330 (1984)]. Preferably, pH of the medium is adjusted to about 5 to about 8. In general, the transformant is cultivated at about 20° C. to about 35° C. for about 24 hours to about 72 hours. If necessary, the culture can be aerated or agitated.

Where insect cells or insects are used as the host, the transformant is cultivated in, for example, Grace's Insect Medium (Grace, T. C. C., Nature, 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary, the culture may be aerated or agitated.

Where animal cells are employed as the host, the transformant is cultivated in, for example, MEM medium containing about 5% to about 20% fetal bovine serum [Science, 122, 501 (1952)], DMEM medium [Virology, 8, 396 (1959)], RPMI 1640 medium [The Journal of the American Medical Association, 199, 519 (1967)], 199 medium [Proceeding of the Society for the Biological Medicine, 73, 1 (1950)], etc. Preferably, pH of the medium is adjusted to about 6 to about 8. The transformant is usually cultivated at about 30° C. to about 40° C. for about 15 hours to about 60 hours and, if necessary, the culture may be aerated or agitated.

As described above, the FPRL2 of the present invention can be produced in the cell or cell membrane, or outside the cell, of the transformant.

The FPRL2 of the present invention can be separated and purified from the culture described above, e.g., by the following procedures.

When the FPRL2 of the present invention is extracted from the culture or cells, after cultivation, the transformants or cells are collected by a publicly known method and suspended in an appropriate buffer. The transformants or cells are then disrupted by publicly known methods such as ultrasonication, a treatment with lysozyme and/or freeze-thaw cycling, followed by centrifugation, filtration, etc. Thus, the crude extract of the FPRL2 can be obtained. The buffer used for the procedures may contain a protein denaturant such as urea or guanidine hydrochloride, or a surfactant such as Triton X-100™, etc. When the FPRL2 is secreted in the culture broth, after completion of the cultivation, the supernatant can be separated from the transformants or cells and collected by publicly known methods.

The FPRL2 contained in the supernatant or the extract thus obtained can be purified by appropriately combining the publicly known methods for separation and purification. Such publicly known methods for separation and purification include a method utilizing difference in solubility such as salting out, solvent precipitation, etc.; a method mainly utilizing difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

When the FPRL2 thus obtained is in a free form, it can be converted into the salt by publicly known methods or modifications thereof. On the other hand, when the FPRL2 is obtained in the form of a salt, it can be converted into the free form or in the form of a different salt by publicly known methods or modifications thereof.

The FPRL2 produced by the recombinant can be treated, prior to or after the purification, with an appropriate protein modifying enzyme so that the FPRL2 can be appropriately modified to partially remove a polypeptide. Examples of the protein-modifying enzyme include trypsin, chymotrypsin, arginyl endopeptidase, protein kinase, glycosidase and the like.

The activity of the thus produced FPRL2 of the present invention can be determined by a binding test to the labeled ligand (ligand peptide), an enzyme immunoassay using a specific antibody, or the like.

Antibodies to the FPRL2 of the present invention may be any of polyclonal and monoclonal antibodies, so long as they can recognize the FPRL2 of the present invention.

The antibodies to the FPRL2 of the present invention can be manufactured according to publicly known methods for producing antibodies or antisera, using the FPRL2 of the present invention as antigens.

[Preparation of Monoclonal Antibody]

(a) Preparation of Monoclonal Antibody-Producing Cells

The FPRL2 of the present invention is administered to mammals either solely or together with carriers or diluents to the site where the antibody can be produced by the administration. In order to potentiate the antibody productivity upon the administration, complete Freund's adjuvants or incomplete Freund's adjuvants may be administered. The administration is usually carried out once every 2 to 6 weeks approximately 2 to 10 times in total. Examples of the applicable mammals are monkeys, rabbits, dogs, guinea pigs, mice, rats, sheep and goats, with the use of mice and rats being preferred.

In the preparation of monoclonal antibody-producing cells, a warm-blooded animal such as mouse, immunized with an antigen is selected, then spleen or lymph nodes are collected after 2 to 5 days from the final immunization and antibody-producing cells contained therein are fused with myeloma cells to give monoclonal antibody-producing hybridomas. Measurement of the antibody titer in antisera may be carried out, for example, by reacting a labeled form of the receptor protein, described later with the antiserum followed by assaying the binding activity of the labeling agent bound to the antibody. The fusion operation may be carried out, for example, using the method known by Koehler and Milstein [Nature, 256, 495 (1975)]. Examples of the fusion promoter are polyethylene glycol (PEG), Sendai virus, etc., among which PEG is preferably employed.

Examples of the myeloma cells are NS-1, P3U1, SP2/0, etc. In particular, P3U1 is preferably employed. A preferred ratio of the count of the antibody-producing cells (spleen cells) used to the count of myeloma cells is within a range of approximately 1:1 to 20:1. When PEG (preferably, PEG 1000 to PEG 6000) is added in a concentration of approximately 10 to 80% followed by culturing at about 20 to 40° C., preferably at about 30 to 37° C. for about 1 to 10 minutes, efficient cell fusion can be carried out.

Various methods can be used for screening of a monoclonal antibody-producing hybridoma. Examples of such methods include a method which comprises adding the hybridoma supernatant to a solid phase (e.g., a microplate) adsorbed with the receptor protein as an antigen directly or together with a carrier, adding an anti-immunoglobulin antibody (where mouse cells are used for the cell fusion, anti-mouse immunoglobulin antibody is used) labeled with a radioactive substance or an enzyme, or protein A and detecting the monoclonal antibody bound to the solid phase; a method which comprises adding the hybridoma culture supernatant to a solid phase adsorbed with an anti-immunoglobulin antibody or protein A, adding the receptor protein labeled with a radioactive substance or an enzyme and detecting the monoclonal antibody bound to the solid phase; and the like.

The monoclonal antibody can be selected in accordance with publicly known methods or modifications thereof. In general, the selection can be effected in a medium for animal cells supplemented with HAT (hypoxanthine, aminopterin and thymidine). Any selection and growth media can be employed as far as the hybridoma can grow there. For example, RPMI 1640 medium containing 1 to 20%, preferably 10 to 20% fetal bovine serum, GIT medium (Wako Pure Chemical Industries, Ltd.) containing 1 to 10% fetal bovine serum, a serum free medium for cultivation of a hybridoma (SFM-101, Nissui Seiyaku Co., Ltd.), etc. can be used for the selection and growth medium. The cultivation is carried out generally at 20 to 40° C., preferably at about 37° C. The time for cultivation is normally for 5 days to 3 weeks, preferably 1 to 2 weeks. The cultivation is carried out generally in 5% $CO_2$. The antibody titer of the hybridoma culture supernatant can be determined as in the assay for the antibody titer in antisera described above.

(b) Purification of Monoclonal Antibody

Isolation and purification of a monoclonal antibody can be carried out by publicly known methods, such as isolation and purification of immunoglobulins [for example, salting-out, alcohol precipitation, isoelectric point precipitation, electrophoresis, adsorption and desorption with ion exchangers (e.g., DEAE), ultracentrifugation, gel filtration, or the specific purification method which comprises collecting an antibody alone with an activated adsorbent such as an antigen-binding solid phase, protein A or protein G and dissociating the binding to obtain the antibody].

[Preparation of Polyclonal Antibody]

The polyclonal antibody of the present invention can be manufactured by publicly known methods or modifications thereof. For example, a complex of immunizing antigen (antigen of FPRL2) and a carrier protein is formed and a mammal is immunized with the complex in a manner similar to the method described above for the manufacture of monoclonal antibody. The product containing the antibody to the FPRL2 of the present invention is collected from the immunized animal. By isolating and purifying the antibody, the polyclonal antibody can be manufactured.

In the complex of antigen and carrier protein for immunizing mammals, the type of carrier protein and the mixing ratio of carrier to hapten may be any type and in any ratio, as long as the antibody is efficiently produced to the hapten immunized by crosslinking to the carrier. For example, a method, in which bovine serum albumin, bovine thyroglobulin or keyhole limpet hemocyanin is coupled to hapten in a carrier-to-hapten weight ratio of approximately 0.1 to 20, preferably approximately 1 to 5, is employed.

A variety of condensation agents can be used for the coupling of carrier to hapten. Glutaraldehyde, carbodiimide, maleimide activated ester and activated ester reagents containing thiol group or dithiopyridyl group, and the like are used for the coupling.

The condensation product is administered to warm-blooded animals either solely or together with carriers or diluents to the site wherein the antibody can be produced. In order to potentiate the antibody productivity upon the administration, complete Freund's adjuvant or incomplete Freund's adjuvant may be administered. The administration is usually made once every about 2 to 6 weeks approximately 3 to 10 times in total.

The polyclonal antibody can be collected from the blood, ascites, etc., preferably from the blood of mammals immunized by the method described above.

The polyclonal antibody titer in antiserum can be assayed by the same procedure as used for the determination of serum antibody titer described above. The isolation and purification of the polyclonal antibody can be carried out, following the method for the isolation and purification of immunoglobulins performed as in the isolation and purification of monoclonal antibodies described above.

The ligand peptide binding to the FPRL2 of the present invention (hereinafter briefly referred to as the ligand peptide) includes the following (1) to (6).

(1) A peptide comprising the same or substantially the same amino acid sequence as the amino acid sequence represented by SEQ ID NO: 3 (GHRP-6);

(2) A peptide comprising the same or substantially the same amino acid sequence as the amino acid sequence represented by SEQ ID NO: 4 (SCPA);

(3) A peptide comprising the same or substantially the same amino acid sequence as the amino acid sequence represented by SEQ ID NO: 5 (RFRP-1-12);

(4) A peptide comprising the same or substantially the same amino acid sequence as the amino acid sequence represented by SEQ ID NO: 6 (neuropeptide Y; NPY); and, (5) A peptide comprising the same or substantially the same amino acid sequence as the amino acid sequence represented by SEQ ID NO: 7 (neuromedin C).

These ligand peptides may be any polypeptide derived from any cells (e.g., hepatocytes, splenocytes, nerve cells, glial cells, β cells of pancreas, bone marrow cells, mesangial cells, Langerhans' cells, epidermic cells, epithelial cells, endothelial cells, fibroblasts, fibrocytes, myocytes, fat cells, immune cells (e.g., macrophages, T cells, B cells, natural killer cells, mast cells, neutrophils, basophils, eosinophils, monocytes), megakaryocytes, synovial cells, chondrocytes, bone cells, osteoblasts, osteoclasts, mammary gland cells or interstitial cells; or the corresponding precursor cells, stem cells, cancer cells, etc.); or any tissues where such cells are present, such as brain or any of brain regions (e.g., olfactory bulb, amygdaloid nucleus, basal ganglia, hippocampus, thalamus, hypothalamus, cerebral cortex, medulla oblongata, cerebellum), spinal cord, pituitary gland, stomach, pancreas, kidneys, liver, gonads, thyroid gland, gallbladder, bone marrow, adrenal glands, skin, muscle, lung, gastrointestinal tract (e.g., large intestine, small intestine), vascular vessels, heart, thymus, spleen, submandibular gland, peripheral blood, prostate, testicle, ovaries, placenta, uterus, bones, cartilages, joints, skeletal muscles, etc. of human or non-human mammals (e.g., guinea pig, rat, mouse, rabbit, swine, sheep, bovine, monkey, etc.); the polypeptide may also be a recombinant polypeptide or synthetic polypeptide.

The term "substantially the same" is used to mean that the activities of a ligand peptide, e.g., a binding activity to the FPRL2, an intracellular signal transduction activity, physiological properties, etc. are substantially the same. Substitution, deletion, addition or insertion of an amino acid does not often cause any significant change in physiological properties or chemical properties of the polypeptide; in this case, such a polypeptide that undergoes substitution, deletion, addition or insertion is considered to be substantially the same as the polypeptide that does not undergo substitution, deletion, addition or insertion. Substantially the same substituent of an amino acid in the amino acid sequence can be selected from, e.g., other amino acids of the class to which the amino acid belongs.

Examples of non-polar (hydrophobic) amino acids include alanine, leucine, isoleucine, valine, proline, phenylalanine, tryptophan, methionine and the like. Examples of polar (neutral) amino acids are glycine, serine, threonine, cysteine, tyrosine, asparagine, glutamine, and the like. Examples of positively charged (basic) amino acids are arginine, lysine, histidine, and the like. Examples of negatively charged (acidic) amino acids include aspartic acid, glutamic acid, and the like.

The ligand peptide comprising the amino acid sequence, which is substantially the same as the amino acid sequences represented by SEQ ID NO: 3, SEQ ID NO: 4, SEQ ID NO: 5, SEQ ID NO: 6 or SEQ ID NO: 7, is not particularly limited, so long as the peptide comprising the amino acid sequence has substantially the same activity (property) as the ligand peptide consisting of the amino acid sequence represented by SEQ ID NO: 3, SEQ ID NO: 4, SEQ ID NO: 5, SEQ ID NO: 6 or SEQ ID NO: 7 and includes, for example, an amino acid sequence having at least about 80% homology, preferably at least about 85% homology, more preferably at least about 90% homology, most preferably at least about 95% homology to the amino acid sequence represented by SEQ ID NO: 3, SEQ ID NO: 4, SEQ ID NO: 5, SEQ ID NO: 6 or SEQ ID NO: 7.

The term substantially the same activity (property) described above means that, for example, the binding activity of the ligand peptide consisting of the amino acid sequence represented by SEQ ID NO: 3, SEQ ID NO: 4, SEQ ID NO: 5, SEQ ID NO: 6 or SEQ ID NO: 7 to FPRL2, or intracellular signal transduction activity, etc. is quantitatively equivalent.

More specifically, as the ligand peptide comprising substantially the same amino acid sequence as the amino acid sequence represented by SEQ ID NO: 3, SEQ ID NO: 4, SEQ ID NO: 5, SEQ ID NO: 6 or SEQ ID NO: 7, there are used peptides consisting of, for example, a) amino acid sequences wherein at least 1 or 2 amino acids (e.g., approximately 1 to 3 amino acids, preferably 1 or 2 amino acids) are deleted of the amino acid sequence represented by SEQ ID NO: 3, SEQ ID NO: 4, SEQ ID NO: 5, SEQ ID NO: 6 or SEQ ID NO: 7; b) amino acid sequences wherein at least 1 or 2 amino acids (e.g., approximately 1 to 3 amino acids, preferably 1 or 2 amino acids) are added to the amino acid sequence represented by SEQ ID NO: 3, SEQ ID NO: 4, SEQ ID NO: 5, SEQ ID NO: 6 or SEQ ID NO: 7; c) amino acid sequences wherein at least 1 or 2 amino acids (e.g., approximately 1 to 3 amino acids, preferably 1 or 2 amino acids) in the amino acid sequence represented by SEQ ID NO: 3, SEQ ID NO: 4, SEQ ID NO: 5, SEQ ID NO: 6 or SEQ ID NO: 7 are substituted by other amino acids; d) peptides consisting of amino acid sequences with these deletion, addition and substitution in combination, and the like. When the amino acid sequence is inserted, deleted or substituted as described above, the position of the insertion, deletion or substitution is not particularly limited.

The ligand peptide further includes substances that the substituents on the side chains of amino acids in the molecule are protected by appropriate protecting groups, conjugated proteins such as so-called glycoproteins having sugar chains, etc.

Furthermore, the ligand peptide includes a ligand peptide having an optional foreign peptide sequence (for example, FLAG, His tag, HA tag, HSV tag, etc.), which could be an epitope (antibody recognition site) at either the N-terminus or the C-terminus.

The ligand peptide is represented in accordance with the conventional way of describing peptides, that is, the N-terminus (amino terminus) at the left hand and the C-terminus (carboxyl terminus) at the right hand. In the ligand peptide including the peptide consisting of the amino acid sequence represented by SEQ ID NO: 1, the C-terminus may be in the form of a carboxyl group (—COOH), a carboxylate (—COO⁻), an amide (—CONH$_2$) or an ester (—COOR), preferably an amide.

Herein, examples of the ester group represented by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl such as a phenyl-$C_{1-2}$ alkyl group, e.g., benzyl, phenethyl, etc.; an α-naphthyl-$C_{1-2}$ alkyl group such as α-naphthylmethyl, etc.; and the like. In addition, pivaloyloxymethyl or the like, which is used widely as an ester for oral administration, may also be used.

Where the ligand peptide contains a carboxyl group (or a carboxylate) at a position other than the C-terminus, it may be amidated or esterified and such an amide or ester is also included within the ligand peptide in the specification of the present application. The ester group in this case may be the same ester group as described with respect to the above C-terminal group; etc.

Furthermore, examples of the ligand peptide include variants wherein the amino group at the N-terminal amino acid residues (e.g., methionine residue) is protected with a protecting group (e.g., a $C_{1-6}$ acyl group such as a $C_{1-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{1-6}$ alkanoyl group, e.g., formyl group, acetyl group, etc.), or conjugated polypeptides such as so-called glycopolypeptides having sugar chains, those wherein C-terminal amino acid residues are modified; etc. Especially, the ligand peptide with the N-terminal methionine residues, the amino acid of which is protected with formyl group, is preferred; in this case, the ligand peptide may further undergo the protection, modification, etc., as described above.

Specifically, for example, the following five C-terminal amide peptides are used as the ligand peptide.
(1) GHRP-6: His-Trp-Ala-Trp-Phe-Lys-NH$_2$ (SEQ ID NO: 3; Trp is a D-form)
(2) SCPA: Ala-Arg-Pro-Gly-Tyr-Leu-Ala-Phe-Pro-Arg-Met-NH2 (SEQ ID NO: 4)
(3) Human RFRP-1-12 (hRFRP-1-12): Met-Pro-His-Ser-Phe-Ala-Asn-Leu-Pro-Leu-Arg-Phe-NH$_2$ (SEQ ID NO: 5)
(4) Porcine neuropeptide Y (pNPY): Tyr-Pro-Ser-Lys-Pro-Asp-Asn-Pro-Gly-Glu-Asp-Ala-Pro-Ala-Glu-Asp-Leu-Ala-Arg-Tyr-Tyr-Ser-Ala-Leu-Arg-His-Tyr-Ile-Asn-Leu-Ile-Thr-Arg-Gln-Arg-Tyr-NH$_2$ (SEQ ID NO: 6)
(5) Human neuromedin C (hNeuromedin C): Gly-Asn-His-Trp-Ala-Val-Gly-His-Leu-Met-NH$_2$ (SEQ ID NO: 7)

The ligand peptide may be in the form of salts. As such salts, there may be used salts with physiologically acceptable acids (e.g., inorganic acids or organic acids) or bases (e.g., alkali metal salts) may be employed, preferably in the form of physiologically acceptable acid addition salts. Examples of such salts include salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

Hereinafter, these peptides are collectively referred to as the ligand peptide including salts.

The ligand peptide may be manufactured by publicly known methods used to purify a polypeptide from human or warm-blooded animal cells or tissues described above. Furthermore, they may also be manufactured by a modification of the methods for peptide synthesis, which will be later described.

Where these ligand peptides are manufactured from human or non-human mammalian tissues or cells, human or non-human mammalian tissues or cells are homogenized, extracted with an acid or the like, and the extract is purified/isolated by a combination of chromatography techniques such as reverse phase chromatography, ion exchange chromatography, and the like.

To synthesize the ligand peptide or amides thereof, commercially available resins that are used for polypeptide synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2',4'-dimethoxyphenyl-hydroxymethyl)phenoxy resin, 4-(2',4'-dimethoxyphenyl-Fmoc-aminoethyl)phenoxy resin, etc. Using these resins, amino acids, in which α-amino groups and functional groups on the side chains are appropriately protected, are condensed on the resin in accordance with the sequence of the objective polypeptide according to various condensation methods publicly known in the art. At the end of the reaction, the polypeptide is excised from the resin and at the same time, the protecting groups are removed. Then, intramolecular disulfide bond-forming reaction, is performed in a highly diluted solution to obtain the objective polypeptide, or amides thereof.

For condensation of the protected amino acids described above, a variety of activating reagents for polypeptide synthesis may be used, and carbodiimides are particularly employed. Examples of such carbodiimides include DCC, N,N'-diisopropylcarbodiimide, N-ethyl-N'-(3-dimethylaminopropyl)carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may arbitrarily be chosen from solvents that are known to be usable for polypeptide condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxan, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to polypeptide bond-forming reactions and is usually selected in the range of approximately −20° C. to 50° C. The activated amino acid derivatives are used generally in an excess of 1.5 to 4 times. The condensation is examined using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole to cancel any possible adverse affect on the subsequent reaction.

Examples of the protecting groups used to protect the starting amino groups include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower ($C_{1-6}$) alkanoyl group, such as acetyl group, an aroyl group such as benzoyl group, and a group derived from carbonic acid such as benzyloxycarbonyl group and ethoxycarbonyl group. Examples of a group appropriately used for the etherification include benzyl group, tetrahydropyranyl group, t-butyl group, etc.

Examples of groups for protecting the phenolic hydroxyl group of tyrosine include Bzl, $Cl_2$-Bzl, 2-nitrobenzyl, Br-Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting materials include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)], etc.

Examples of the activated amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethanesulfonic acid or trifluoroacetic acid, or a mixture solution of these acids; a treatment with a base such as diisopropylethylamine, triethylamine, piperidine or piperazine; and reduction with sodium in liquid ammonia. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol or 1,2-ethanedithiol. Furthermore, 2,4-dinitrophenyl group known as the protecting group for the imidazole of histidine is removed by a treatment with thiophenol. Formyl group used as the protecting group for the indole of tryptophan is eliminated by the aforesaid acid treatment in the presence of 1,2-ethanedithiol, 1,4-butanedithiol, etc. as well as by a treatment with an alkali such as a dilute sodium hydroxide solution, dilute ammonia, etc.

Protection of functional groups that should not be involved in the reaction of the starting materials, protecting groups, elimination of the protecting groups and activation of functional groups involved in the reaction may be appropriately selected from publicly known groups and publicly known means.

In another method for obtaining the amidated ligand peptide, for example, the α-carboxyl group of the carboxy terminal amino acid is first protected by amidation; the peptide (polypeptide) chain is then extended from the amino group side to a desired length. Thereafter, a polypeptide from which only the protecting group of the N-terminal α-amino group of the peptide chain has been eliminated and a polypeptide from which only the protecting group of the C-terminal carboxyl group has been eliminated are prepared. The two polypeptides are condensed in a mixture of the solvents described above. The details of the condensation reaction are the same as described above. After the protected polypeptide obtained by the condensation is purified, all the protecting groups are eliminated by the method described above to obtain the desired crude polypeptide. This crude polypeptide is purified by various known purification means. Lyophilization of the major fraction gives the amide of the desired ligand peptide.

To prepare the esterified ligand peptide, for example, the α-carboxyl group of the carboxy terminal amino acid is condensed with a desired alcohol to prepare the amino acid ester, which is followed by procedure similar to the preparation of the amidated ligand peptide above to give the desired esterified polypeptides.

The ligand peptide can be manufactured by publicly known methods for peptide synthesis. For the peptide synthesis, for example, either solid phase synthesis or liquid phase synthesis may be used. That is, the partial peptides or amino acids that can constitute the ligand peptide are condensed with the remaining part. Where the product contains protecting groups, these protecting groups are removed to give the desired peptide. Publicly known methods for condensation and elimination of the protecting groups are described in (i)-(v) below.

(i) M. Bodanszky & M. A. Ondetti: Peptide Synthesis, Interscience Publishers, New York (1966)

(ii) Schroeder & Luebke: The Peptide, Academic Press, New York (1965)

(iii) Nobuo Izumiya, et al.: *Peptide Gosei-no-Kiso to Jikken* (Basics and experiments of peptide synthesis), published by Maruzen Co. (1975)

(iv) Haruaki Yajima & Shunpei Sakakibara: *Seikagaku Jikken Koza* (Biochemical Experiment) 1, *Tanpakushitsu no Kagaku* (Chemistry of Proteins) IV, 205 (1977)

(v) Haruaki Yajima ed.: *Zoku Iyakuhin no Kaihatsu* (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography, recrystallization, etc. to give the polypeptide of the present invention or the partial peptide of the present invention. When the polypeptide obtained by the above methods is in a free form, they may be converted into appropriate salts by publicly known methods or modifications thereof; when the polypeptide is obtained in a salt form, it may be converted into a free form or in the form of a different salt by a publicly known method or a modification thereof.

Antibody to the ligand peptide can be manufactured in a manner similar to the method of preparing the antibody to the FPRL2 of the present invention.

The ligand peptide, FPRL2 and DNA encoding the FPRL2 (hereinafter sometimes briefly referred to as the DNA of the present invention), antibody to the ligand peptide or FPRL2 (hereinafter sometimes briefly referred to as the antibody of the present invention), antisense DNA to the DNA of the present invention (hereinafter sometimes briefly referred to as the antisense DNA of the present invention) possess applications described later.

(1) Agent for Preventing/Treating Diseases Associated with Dysfunction of the FPRL2 of the Present Invention When it is found to involve abnormalities or deficiencies in the ligand peptide or FPRL2 or in the polynucleotide (e.g., DNA, etc.) encoding the same, or when the expression level of the ligand peptide decrease abnormally, various diseases are developed, for example, asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as, cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endotoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, immunodeficiency, infections, cancer, etc.

Therefore, when the physiological activities of the ligand peptide cannot be expected in a patient (deficiency of the ligand peptide or FPRL2) due to a decrease of the ligand peptide or FPRL2 in vivo, the amount of FPRL2 can be increased in the body of the patient a) by administering the ligand peptide or FPRL2 to the patient thereby to supplement the amount of the ligand peptide or FPRL2; or b) (i) by administering the DNA encoding the FPRL2 to the patient and expressing the same, or (ii) by inserting and expressing the DNA encoding the FPRL2 in the objective cells and then transplanting the cells to the patient, whereby the activities of the ligand can be sufficiently exhibited.

Therefore, a) the ligand peptide, b) FPRL2 or c) the DNA encoding FPRL2 may be used as a pharmaceutical such as an agent for preventing/treating diseases associated with dysfunction of the ligand peptide or FPRL2.

Specifically, the ligand peptide, FPRL2 or the DNA of the present invention can be used as a low-toxic and safe drug, including an agent for preventing/treating, e.g., asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as, cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endotoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, immunodeficiency, infections, cancer, etc., especially immunodeficiency.

When the ligand peptide or FPRL2 is used as the agent for preventing/treating described above, the ligand peptide or FPRL2 is prepared into pharmaceutical preparations in a conventional manner.

On the other hand, when the DNA of the present invention is used as the preventive/therapeutic agent described above, the DNA of the present invention is inserted into an appropriate vector such as retrovirus vector, adenovirus vector, adenovirus-associated virus vector, etc. and then administered to human or other warm-blooded animal in a conventional manner. The DNA of the present invention may also be administered as naked DNA, or with adjuvants to assist its uptake by gene gun or through a catheter such as a catheter with a hydrogel.

For example, a) the ligand peptide, b) FPRL2, or c) the DNA of the present invention can be used orally, for example, in the form of tablets which may be sugar coated if necessary and desired, capsules, elixirs, microcapsules etc., or parenterally in the form of injectable preparations such as a sterile solution and a suspension in water or with other pharmaceutically acceptable liquid. These preparations can be manufactured by mixing the a) the ligand peptide, b) FPRL2, or c) the DNA of the present invention with a physiologically acceptable known carrier, a flavoring agent, an excipient, a vehicle, an antiseptic agent, a stabilizer, a binder, etc. in a unit dosage form required in a generally accepted manner that is applied to making pharmaceutical preparations. The active ingredient in the preparation is controlled in such a dose that an appropriate dose is obtained within the specified range given.

Additives miscible with tablets, capsules, etc. include a binder such as gelatin, cornstarch, tragacanth and gum arabic, an excipient such as crystalline cellulose, a swelling agent such as cornstarch, gelatin, alginic acid, etc., a lubricant such as magnesium stearate, a sweetening agent such as sucrose, lactose and saccharin, and a flavoring agent such as peppermint, akamono oil or cherry, etc. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition. Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol or the like), a polyalcohol (e.g., propylene glycol and polyethylene glycol), a nonionic surfactant (e.g., polysorbate 80™ and HCO-50), etc. Examples of the oily medium include sesame oil and soybean oil, which may also be used in combination with a dissolution aid such as benzyl benzoate and benzyl alcohol.

The preventive/therapeutic agent described above may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus-prepared liquid for injection is normally filled in an appropriate ampoule.

Since the thus obtained pharmaceutical preparation is safe and low toxic, the preparation can be administered to human or mammal (e.g., rat, mouse, rabbit, sheep, swine, bovine, cat, dog, monkey, etc.).

The dose of the ligand peptide may vary depending on subject to be administered, target organ, conditions, methods for administration, etc. In the case of oral administration, the ligand peptide is administered to an adult patient (as 60 kg body weight) with immunodeficiency generally in a daily dose of approximately 0.1 to 100 mg, preferably approximately 1.0 to 50 mg and more preferably approximately 1.0 to 20 mg. In parenteral administration, a single dose of the ligand peptide may vary depending on subject to be administered, target organ, conditions, methods for administration, etc. For example, in the form of injection, it is advantageous to administer the ligand peptide intravenously to an adult patient (as 60 kg) with immunodeficiency, generally in a daily dose of approximately 0.01 to 30 mg, preferably approximately 0.1 to 20 mg, and more preferably approximately 0.1 to 10 mg. For other animal species, the corresponding dose as converted per 60 kg weight can be administered.

The dose of the DNA of the present invention may vary depending on subject to be administered, target organ, conditions, methods for administration, etc. In the case of oral administration, the ligand peptide is administered to an adult patient (as 60 kg body weight) with immunodeficiency generally in a daily dose of approximately 0.1 to 100 mg, preferably approximately 1.0 to 50 mg and more preferably approximately 1.0 to 20 mg. In parenteral administration, a single dose of the DNA may vary depending on subject to be administered, target organ, conditions, methods for administration, etc. For example, in the form of injection, it is advantageous to administer the ligand peptide intravenously to an adult patient (as 60 kg) with immunodeficiency, generally in a daily dose of approximately 0.01 to 30 mg, preferably approximately 0.1 to 20 mg, and more preferably approximately 0.1 to 10 mg. For other animal species, the corresponding dose as converted per 60 kg weight can be administered.

(2) Gene Diagnostic Agent

By using the DNA and the antisense DNA of the present invention, e.g., as a probe, abnormality (gene abnormality) of the DNA or mRNA encoding the FPRL2 of the present invention or partial peptide thereof in human or mammal (e.g., rat, mouse, rabbit, sheep, swine, bovine, cat, dog, monkey, etc.) can be detected. Thus, the DNA and the antisense DNA of the present invention is useful as a gene diagnostic agent for the damage to the DNA or mRNA, mutation, a decreased expression or an increased expression, or overexpression of the DNA or mRNA.

The gene diagnosis described above using the DNA or antisense DNA of the present invention can be performed by, for example, the publicly known Northern hybridization assay or the PCR-SSCP assay (Genomics, 5, 874-879 (1989); Proceedings of the National Academy of Sciences of the United States of America, 86, 2766-2770 (1989)).

For example, when decreased expression of FPRL2 is detected by northern hybridization, or when DNA mutation is detected by PCR-SSCP, it can be diagnosed that one suffers from diseases such as asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as, cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endotoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, immunodeficiency, infections, cancer, etc., especially immunodeficiency; or it is highly likely for one to suffer from the diseases in the future.

On the other hand, when overexpression of FPRL2 is detected by northern hybridization, it can be diagnosed that one suffers from diseases such as asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as, cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endotoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, immunodeficiency, infections, cancer, etc., especially, asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as, cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endotoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, infections or cancer; or it is highly likely for one to suffer from these diseases in the future.

(3) Pharmaceutical Comprising the Compound or its Salt that Changes the Expression Level of the FPRL2 of the Present Invention By using the DNA of the present invention as a probe, the DNA can be used for screening the compound or its salt that changes an expression level of the FPRL2 of the present invention.

That is, the present invention provides a method of screening the compound or its salt that changes the expression level of the FPRL2 of the present invention, which comprises measuring the amount of mRNA in the FPRL2 of the present invention contained, for example, in (i) a) blood, b) particular organs, c) tissues or cells isolated from non-human mammals or in (ii) transformants, etc.

The amount of mRNA in the FPRL2 of the present invention can be specifically measured as follows.

(i) Normal or disease models of non-human mammals (e.g., mice, rats, rabbits, sheep, swine, bovine, cats, dogs, monkeys, more specifically, rats, mice or rabbits of Alzheimer's disease model, etc.) receive administration of a drug (e.g., an immunomodulator, etc.) or physical stress (e.g., soaking stress, electric shock, light and darkness, low temperature, etc.), and the blood, particular organs (e.g., brain, liver, kidney, etc.), or tissues or cells isolated from the organs are obtained after a specified period of time.

The mRNA of the FPRL2 of the present invention contained in the thus obtained cells is extracted from the cells, for example, in a conventional manner and quantified by means of, e.g., TaqManPCR, or may also be analyzed by northern blot technique by publicly known methods.

(ii) Transformants that express the FPRL2 of the present invention are prepared according to the methods described above, and the mRNA of the FPRL2 of the present invention contained in the transformants can be quantified and analyzed, as described above.

The compound or its salt that changes the expression level of the FPRL2 of the present invention can be screened by the following procedures.

(i) To non-human mammals of normal or disease models, a test compound is administered at a specified period of time before (30 minutes to 24 hours before, preferably 30 minutes to 12 hours before, more preferably 1 hour to 6 hours before), at a specified time after (30 minutes to 3 days after, preferably 1 hour to 2 days after, more preferably 1 hour to 24 hours after), or simultaneously with a drug or physical stress. At a specified time (30 minute to 3 days, preferably 1 hour to 2 days, more preferably 1 hour to 24 hours) after administration of the test compound, the mRNA level in the FPRL2 of the present invention contained in cells are quantified and analyzed.

(ii) Transformants are cultured in a conventional manner and a test compound is mixed in the culture medium. After a specified time (after 1 day to 7 days, preferably after 1 day to 3 days, more preferably after 2 to 3 days), the mRNA level in the FPRL2 of the present invention contained in the transformants can be quantified and analyzed.

Examples of the test compounds include peptides, proteins, non-peptide compounds, synthetic compounds, fermentation products, cell extracts, plant extracts, animal tissue extracts, blood plasma, etc. These test compounds may be either novel or publicly known compounds.

The test compound may form salts and may be used in the form of salts with physiologically acceptable acids (e.g., inorganic acids, etc.) or bases (e.g., organic acids, etc.), preferably in the form of physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

The compound obtained by the screening methods of the present invention is a compound having the activity of changing the expression level of the FPRL2 of the present invention. Specifically, it is (a) a compound that potentiates FPRL2-mediated cell stimulating activity (e.g., the activities that promote or suppress arachidonic acid release, acetylcholine release, intracellular $Ca^{2+}$ release, intracellular cAMP production, intracellular cAMP production inhibition, intracellular cGMP production, inositol phosphate production, changes in cell membrane potential, phosphorylation of intracellular proteins, activation of c-fos, pH reduction, etc.) by increasing the expression level of the FPRL2 of the present invention; and (b) a compound that attenuates the cell stimulating activity by decreasing the expression level of the FPRL2 of the present invention.

Examples of these compounds include peptides, proteins, non-peptide compounds, synthetic compounds, fermentation products, etc. These compounds may be either novel or publicly known compounds.

As salts of the compounds there may be used salts with physiologically acceptable acids (e.g., inorganic acids, etc.) or bases (e.g., organic acids, etc.), preferably in the form of physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

The compound obtained by the screening method described above includes the following compounds:

(1) The compound that increases the expression level of the FPRL2 of the present invention to prevent/treat diseases associated with dysfunction of the FPRL2 of the present invention, specifically, the compound that prevent/treat asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as, cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endotoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, immunodeficiency, infections, cancer, etc., especially immunodeficiency; or (2) The compound that decreases the expression level of the FPRL2 of the present invention to prevent/treat diseases caused by overexpression of the FPRL2 of the present invention, for example, asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as, cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endotoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, immunodeficiency, infections, cancer, etc., especially, the compound that prevents/treats asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as, cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endotoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, infections or cancer; and the like.

Therefore, the compound or its salt that increases the expression level of the FPRL2 of the present invention, which is obtained by the screening method described above, can be used as a low-toxic and safe drug, including an agent for preventing/treating, for example, asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as, cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endotoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, immunodeficiency, infections, cancer, etc., especially immunodeficiency.

On the other hand, the compound or its salt that decreases he expression level of the FPRL2 of the present invention, which is obtained by the screening method described above, can be used as a pharmaceutical, including an agent for preventing/treating diseases caused by overexpression of the FPRL2 of the present invention, such as asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as, cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endotoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, immunodeficiency, infections, cancer, etc., especially, asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as, cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endotoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, infections, cancer, etc.

Where the compound or its salt, which is obtained by the screening methods of the present invention, is used as a pharmaceutical composition, the compound or its salt can be formed into a pharmaceutical preparation in a conventional manner.

For example, the compound can be used orally in the form of tablets which may be tablets, if necessary, coated with sugar, capsules, elixirs, microcapsules, etc., or parenterally in the form of injectable preparations such as a sterile solution or a suspension in water or with other pharmaceutically acceptable liquid. These preparations can be manufactured, e.g., by mixing the compound, with a physiologically acceptable known carrier, flavoring agent, excipient, vehicle, antiseptic, stabilizer, binder, etc., in a unit dosage form required in a generally accepted manner applied to making pharmaceutical preparations. The active ingredient in the preparation is controlled in such an amount that an appropriate dose is obtained within the specified range given.

Additives miscible with tablets, capsules, etc. include a binder such as gelatin, corn starch, tragacanth or gum arabic, an excipient such as crystalline cellulose, a swelling agent such as corn starch, gelatin, alginic acid, etc., a lubricant such as magnesium stearate, a sweetening agent such as sucrose, lactose or saccharin, a flavoring agent such as peppermint, akamono oil or cherry, and the like. When the unit dosage is in the form of capsules, liquid carriers such as oils and fats may further be used together with the additives described above. A sterile composition for injection may be formulated following a conventional manner used to make pharmaceutical compositions, e.g., by dissolving or suspending the active ingredients in a vehicle such as water for injection with a naturally occurring vegetable oil such as sesame oil, coconut oil, etc. to prepare the pharmaceutical composition. Examples of an aqueous medium for injection include physiological saline, an isotonic solution containing glucose and other auxiliary agents (e.g., D-sorbitol, D-mannitol, sodium chloride, etc.) or the like, which may be used in combination with an appropriate dissolution aid such as an alcohol (e.g., ethanol), a polyalcohol (e.g., propylene glycol, polyethylene glycol), a nonionic surfactant (e.g., polysorbate 80™ and HCO-50), etc. As an oily medium, for example, sesame oil, soybean oil or the like may be used, which can be used in combination with a dissolution aid such as benzyl benzoate, benzyl alcohol, etc.

Furthermore, the preventive/therapeutic agents described above may also be formulated with a buffer (e.g., phosphate buffer, sodium acetate buffer), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

Since the thus obtained pharmaceutical preparation is safe and low toxic, the preparation can be administered to human or mammals (e.g., rats, mice, rabbits, sheep, swine, bovine, cats, dogs, monkeys, etc.).

The dose of the compound or its salts varies depending on subject to be administered, target organ, conditions, methods for administration, etc.; in oral administration, the compound that increases the expression level of the FPRL2 of the present invention is administered to the patient (as 60 kg body weight) with immunodeficiency normally in a dose of about 0.1 mg to about 100 mg, preferably about 1.0 to about 50 mg, and more preferably about 1.0 to about 20 mg per day. In parenteral administration, the single dose may vary depending on subject to be administered, target organ, conditions, methods for administration, etc. but the compound that increases the expression level of the FPRL2 of the present invention is advantageously administered intravenously to the patient (as 60 kg body weight) with immunodeficiency in a daily dose of about 0.01 to about 30 mg, preferably about 0.1 to about 20 mg, and more preferably about 0.1 to about 10 mg. For other animal species, the corresponding dose as converted per 60 kg body weight can be administered.

(4) Method for Diagnosis Using the Antibody of the Present Invention

The antibodies to the ligand peptide are capable of specifically recognizing the ligand peptide of the present invention. Therefore, the antibodies can be used to detect or neutralize the ligand peptide in a test fluid.

The antibodies to the FPRL2 of the present invention are capable of specifically recognizing the FPRL2 of the present invention. Therefore, the antibodies can be used to detect or neutralize the FPRL2 in a test fluid.

Hereinafter, the methods for quantifying the FPRL2 using the antibodies to the FPRL2 of the present invention are described below, but the method for quantifying the ligand peptide using the antibodies to the ligand peptide can also be carried out in a similar manner.

That is, the present invention provides, for example, the following quantification methods:

(i) a method for quantifying the FPRL2 in a test fluid, which is characterized by competitively reacting the antibody of the present invention with the test fluid and a labeled form of FPRL2, and measuring a ratio of the labeled FPRL2 bound to the antibody; and, (ii) a method for quantifying the FPRL2 in a test fluid, which is characterized by reacting the test fluid with the antibody of the present invention immobilized on a carrier and another labeled form of the antibody of the present invention simultaneously or sequentially, and measuring the activity of the label on the immobilized carrier.

In the quantification method (ii) described above, it is preferred that one antibody recognizes the N-terminal region of FPRL2, and another antibody reacts with the C-terminal region of FPRL2.

Using the monoclonal antibodies to FPRL2, the FPRL2 can be assayed. The FPRL2 can also be detected by tissue staining or the like. For this purpose, the antibody molecule itself may be used, or $F(ab')_2$, Fab' or Fab fractions of the antibody molecule may also be used.

The methods quantifying FPRL2 using the antibodies of the present invention are not particularly limited. Any quantification method can be used, so long as the amount of antibody, antigen, or antibody-antigen complex corresponding to the amount of antigen (e.g., the amount of FPRL2) in the test fluid can be detected by chemical or physical means and the amount of the antigen can be calculated from a standard curve prepared from standard solutions containing known amounts of the antigen. For example, nephrometry, competitive methods, immunometric method, and sandwich method are appropriately used, with the sandwich method described below being most preferable in terms of sensitivity and specificity.

As the labeling agent for the assays using labeled substances, there are employed, for example, radioisotopes, enzymes, fluorescent substances, luminescent substances, etc. For the radioisotope, for example, $[^{125}I]$, $[^{131}I]$, $[^{3}H]$, $[^{14}C]$ and the like are used. As the enzyme described above, stable enzymes with high specific activity are preferred; for example, β-galactosidase, β-glucosidase, alkaline phosphatase, peroxidase, malate dehydrogenase and the like are used. Examples of the fluorescent substance used are fluorescamine and fluorescein isothiocyanate. For the luminescent substance, there are used, for example, luminol, luminol derivatives, luciferin, and lucigenin. Furthermore, the biotin-avidin system may be used for binding antibody or antigen to the label.

For immobilization of antigen or antibody, physical adsorption may be used. Chemical binding methods conventionally used for insolubilization or immobilization of FPRL2, enzymes or the like may also be used. For the carrier, for example, insoluble polysaccharides such as agarose, dextran, cellulose, etc.; synthetic resin such as polystyrene, polyacrylamide, silicon, etc., and glass or the like are used.

In the sandwich method, the immobilized monoclonal antibody of the present invention is reacted with a test fluid (primary reaction), then with the labeled monoclonal antibody of the present invention (secondary reaction), and the activity of the label on the immobilizing carrier is measured, whereby the amount of the FPRL2 of the present invention in the test fluid can be quantified. The order of the primary and secondary reactions may be reversed, and the reactions may be performed simultaneously or with an interval. The methods of labeling and immobilization can be performed by the methods described above. In the immunoassay by the sandwich method, the antibody used for immobilized or labeled antibodies is not necessarily one species, but a mixture of two or more species of antibody may be used to increase the measurement sensitivity.

In the methods of the present invention for assaying FPRL2 by the sandwich method, antibodies that bind to different sites of FPRL2 are preferably used as the monoclonal antibodies of the present invention for the primary and secondary reactions. That is, in the antibodies used for the primary and secondary reactions are, for example, when the antibody used in the secondary reaction recognizes the C-terminal region of FPRL2, it is preferable to use the antibody recognizing the region other than the C-terminal region for the primary reaction, e.g., the antibody recognizing the N-terminal region.

The monoclonal antibodies of the present invention can be used for the assay systems other than the sandwich method, for example, competitive method, immunometric method, nephrometry, etc.

In the competitive method, antigen in a test fluid and the labeled antigen are competitively reacted with antibody, and the unreacted labeled antigen (F) and the labeled antigen bound to the antibody (B) are separated (B/F separation). The amount of the label in B or F is measured, and the amount of the antigen in the test fluid is quantified. This reaction method includes a liquid phase method using a soluble antibody as an antibody, polyethylene glycol for B/F separation and a secondary antibody to the soluble antibody, and an immobilized method either using an immobilized antibody as the primary antibody, or using a soluble antibody as the primary antibody and immobilized antibody as the secondary antibody.

In the immunometric method, antigen in a test fluid and immobilized antigen are competitively reacted with a definite amount of labeled antibody, the immobilized phase is separated from the liquid phase, or antigen in a test fluid and an excess amount of labeled antibody are reacted, immobilized antigen is then added to bind the unreacted labeled antibody to the immobilized phase, and the immobilized phase is separated from the liquid phase. Then, the amount of the label in either phase is measured to quantify the antigen in the test fluid.

In the nephrometry, insoluble precipitate produced after the antigen-antibody reaction in gel or solution is quantified. When the amount of antigen in the test fluid is small and only a small amount of precipitate is obtained, laser nephrometry using scattering of laser is advantageously employed.

For applying these immunological methods to the quantification methods of the present invention, any particular conditions or procedures are not required. The system for measuring the FPRL2 of the present invention is constructed by adding the usual technical consideration in the art to the conventional conditions and procedures. For the details of these general technical means, reference can be made to the following reviews and texts.

For example, Hiroshi Irie, ed. "Radioimmunoassay" (Kodansha, published in 1974), Hiroshi Irie, ed. "Sequel to the Radioimmunoassay" (Kodansha, published in 1979), Eiji Ishikawa, et al. ed. "Enzyme immunoassay" (Igakushoin, published in 1978), Eiji Ishikawa, et al. ed. "Immunoenzyme assay" (2nd ed.) (Igakushoin, published in 1982), Eiji Ishikawa, et al. ed. "Immunoenzyme assay" (3rd ed.) (Igakushoin, published in 1987), Methods in ENZYMOLOGY, Vol. 70 (Immunochemical Techniques (Part A)), ibid., Vol. 73 (Immunochemical Techniques (Part B)), ibid., Vol. 74 (Immunochemical Techniques (Part C)), ibid., Vol. 84 (Immunochemical Techniques (Part D: Selected Immunoassays)), ibid., Vol. 92 (Immunochemical Techniques (Part E: Monoclonal Antibodies and General Immunoassay Methods)), ibid., Vol. 121 (Immunochemical Techniques (Part I: Hybridoma Technology and Monoclonal Antibodies)) (all published by Academic Press Publishing).

As described above, the FPRL2 of the present invention can be quantified with high sensitivity, using the antibodies of the present invention.

Furthermore, where a reduction in the FPRL2 level is detected by quantifying the FPRL2 level using the antibodies of the present invention, it can be diagnosed that one suffers from diseases, for example, asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as, cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endotoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, immunodeficiency, infections, cancer, etc., especially immunodeficiency; or it is highly likely to suffer from these disease in the future.

Where an increase in the FPRL2 level is detected, it can be diagnosed that one suffers from, for example, diseases caused by overexpression of FPRL2, such as asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as, cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endotoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, immunodeficiency, infections, cancer, etc., especially, asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as, cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endotoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, infections or cancer, etc.; or it is highly likely to suffer from these disease in the future.

(5) Methods of Screening Agonists for FPRL2

The ligand peptide binds to FPRL2 so that suppression of intracellular cAMP production is observed. Thus, the FPRL2 is useful as a reagent for searching or determining an agonist (including a naturally occurring ligand and a synthetic ligand) for the FPRL2 other than the ligand peptide described above, using this intracellular signal as an indicator.

That is, the present invention provides a method of determining the agonist for FPRL2, which is characterized by assaying the FPRL2-mediated intracellular cAMP production inhibition activity, when a test compound is brought in contact with a cell containing the FPRL2.

Examples of test compounds include publicly known ligands (for example, angiotensin, bombesin, canavinoid, cholecystokinin, glutamine, serotonin, melatonin, neuropeptide Y, opioids, purines, vasopressin, oxytocin, PACAP (e.g., PACAP27, PACAP38), secretin, glucagon, calcitonin, adrenomedulin, somatostatin, GHRH, CRF, ACTH, GRP, PTH, VIP (vasoactive intestinal and related polypeptide), somatostatin, dopamine, motilin, amylin, bradykinin, CGRP (calcitonin gene-related peptide), leukotrienes, pancreastatin, prostaglandins, thromboxane, adenosine, adrenaline, the chemokine superfamily (e.g., the CXC chemokine subfamily such as IL-8, GROα, GROβ, GROγ, NAP-2, ENA-78, GCP-2, PF4, IP-10, Mig, PBSF/SDF-1, etc.; the CC chemokine subfamily such as MCAF/MCP-1, MCP-2, MCP-3, MCP-4, eotaxin, RANTES, MIP-1α, MIP-1β, HCC-1, MIP-3α/LARC, MIP-3β/ELC, I-309, TARC, MIPF-1, MIPF-2/eotaxin-2, MDC, DC-CK1/PARC, SLC, etc.; the C chemokine subfamily such as lymphotactin, etc.; the CX3C chemokine subfamily such as fractalkine, etc.), endothelin, enterogastrin, histamin, neurotensin, TRH, pancreatic polypeptide, galanin, lysophosphatidic acid (LPA), sphingosine 1-phosphate, etc.) as well as other substances, for example, tissue extracts, cell culture supernatants from humans or mammals (e.g., mice, rats, swine, bovine, sheep, monkeys, etc.) or low molecular synthetic compound. For example, the tissue extract, or cell culture supernatant, is added to the FPRL2 while assaying the cell stimulating activity and fractionating to finally obtain a single ligand.

(6) Method of Screening a Compound or its Salt that Changes the Binding Property of the FPRL2 of the Present Invention to the Ligand Peptide (Agonist, Antagonist, etc.) or Signal Transduction, and a Pharmaceutical Comprising the Compound or its Salt that Changes the Binding Property of the FPRL2 of the Present Invention to the Ligand Peptide or Signal Transduction By using the FPRL2 of the present invention, or by constructing an expression system for recombinant FPRL2 and using the receptor-binding assay system with the expression system, the compound (e.g., peptide, protein, a non-peptide compound, a synthetic compound, a fermentation product, etc.) or salts thereof that change the binding property of the ligand peptide to the FPRL2 of the present invention or signal transduction can be screened efficiently.

Examples of these compounds include (a) a compound having the FPRL2-mediated cell stimulating activity (a so-called agonist for the FPRL2 of the present invention), (b) a compound inhibiting the cell stimulating activity (a so-called antagonist to the FPRL2 of the present invention), (c) a compound that potentiates the binding affinity of the ligand peptide to the FPRL2 of the present invention, or (d) a compound that decreases the binding affinity of the ligand peptide to the FPRL2 of the present invention, and the like.

Examples of the cell stimulating activity include activities that promote or suppress arachidonic acid release, acetylcholine release, intracellular $Ca^{2+}$ release, intracellular cAMP production, intracellular cGMP production, inositol phosphate production, changes in cell membrane potential, phosphorylation of intracellular proteins, activation of c-fos, pH reduction, etc. Among them, the intracellular cAMP production inhibition activity and the like are preferred.

That is, the present invention provides a method of screening a compound or its salt that changes the binding property of the ligand peptide to the FPRL2 of the present invention or signal transduction, which is characterized by comparing (i) the case wherein the FPRL2 of the present invention is brought in contact with the ligand peptide; and (ii) the case wherein the FPRL2 of the present invention is brought in contact with the ligand peptide and a test compound.

According to the screening method of the present invention, the method is characterized by assaying and comparing, e.g., a binding amount of the ligand peptide to the FPRL2, a cell stimulating activity, etc. in the cases (i) and (ii).

As the ligand peptide, the compound or its salt (for example, a low molecular synthetic compound, preferably a low molecular synthetic agonist), which changes the binding property of the ligand peptide to the FPRL2 of the present invention, can be used instead of the said ligand peptide. The compound or its salt, which change the binding property of the ligand-peptide to the FPRL2 of the present invention, can be obtained using the screening method described later. In the screening method of the present invention, these ligand peptides and the compound or its salt that changes the binding property of the ligand peptide to the FPRL2 of the present invention are collectively referred to as the ligand peptide.

More specifically, the present invention provides the following methods:

a) A method of screening a compound or its salt that changes the binding property of the ligand peptide to the FPRL2 of the present invention or signal transduction, which is characterized by measuring the binding amount of the ligand peptide to the FPRL2 in the case wherein a labeled form of the ligand peptide is brought in contact with the FPRL2 of the present invention and in the case wherein a labeled form of the ligand peptide and a test compound are brought in contact with the FPRL2 of the present invention, and comparing the binding amount between the cases;

b) A method of screening a compound or its salt that changes the binding property of the ligand peptide to the FPRL2 of the present invention or signal transduction, which is characterized by measuring the binding amount of a labeled form of the ligand peptide to a cell containing the FPRL2 of the present invention or a membrane fraction of said cell, in the case wherein the labeled ligand peptide is brought in contact with the cell containing the FPRL2 of the present invention or the membrane fraction and in the case wherein the labeled ligand peptide and a test compound are brought in contact with the cell containing the FPRL2 of the present invention or a membrane fraction of said cell, and comparing the binding amount between the cases;

c) A method of screening a compound or its salt that changes the binding property of the ligand peptide to the FPRL2 of the present invention or signal transduction, which is characterized by measuring the binding amount of a labeled form of the ligand peptide to said FPRL2, in the case wherein the labeled ligand peptide is brought in contact with FPRL2 expressed on a cell membrane by culturing a transformant containing the DNA of the present invention and in the case wherein the labeled ligand peptide and a test compound are brought in contact with the FPRL2 of the present invention expressed on the cell membrane by culturing a transformant containing the DNA of the present invention, and comparing the binding amount between the cases;

d) A method of screening a compound or its salt that changes the binding property of the ligand peptide to the FPRL2 of the present invention or signal transduction, which is characterized by assaying the FPRL2-mediated cell stimulating activity in the case wherein a compound (e.g., a ligand peptide to the FPRL2 of the present invention, etc.) that activates the FPRL2 of the present invention is brought in contact with a cell containing the FPRL2 of the present invention and in the case wherein a compound that activates the FPRL2 of the present invention and a test compound are brought in contact with the cell containing the FPRL2 of the present invention, and comparing the cell stimulating activity between the cases; and e) A method of screening a compound or its salt that changes the binding property of the ligand peptide to the FPRL2 of the present invention or signal transduction, which is characterized by assaying the receptor protein-mediated cell stimulating activity in the case wherein a compound (e.g., a ligand peptide to the FPRL2 of the present invention, etc.) that activates the FPRL2 of the present invention is brought in contact with the FPRL2 of the present invention expressed on a cell membrane by culturing a transformant containing the DNA of the present invention and in the case wherein a compound that activates the FPRL2 of the present invention and a test compound are brought in contact with the FPRL2 of the present invention expressed on a cell membrane by culturing a transformant containing the DNA of the present invention, and comparing the cell stimulating activity between the cases.

Hereinafter the screening method of the present invention will be described more specifically.

First, the FPRL2 of the present invention, which is used for the screening method of the present invention, may be any one so long as it contains the FPRL2 of the present invention described above, though a membrane fraction comprising the FPRL2 of the present invention from mammalian organs are preferably employed. Since it is very difficult to obtain human-derived organs especially, human-derived FPRL2, etc. expressed abundantly by use of recombinants are suitable for use in the screening.

To produce the FPRL2 of the present invention, the methods described above can be used, and the DNA of the present invention is preferably expressed on mammalian cells or insect cells. As the DNA fragment encoding the target protein region, a complementary DNA may be used but is not limited thereto. For example, gene fragments or a synthetic DNA may also be used. In order to introduce the DNA fragment encoding the FPRL2 of the present invention into host animal cells and express the same efficiently, the DNA fragment is preferably incorporated into a polyhedron promoter of nuclear polyhedrosis virus (NPV) belonging to the Baculovirus, an SV40-derived promoter, a promoter of retrovirus, a metallothionein promoter, a human heat shock promoter, a cytomegalovirus promoter, SRα promoter, etc. at the downstream thereof. The quantity and quality of the thus expressed receptors can be examined by a publicly known method, for example, by the method described in the literature [Nambi, P. et al., J. Biol. Chem., 267, 19555-19559, 1992].

Accordingly, in the screening method of the present invention, the substance containing the FPRL2 of the present invention may be FPRL2 purified by publicly known methods, or a cell containing said FPRL2 or a membrane fraction of the cell containing FPRL2 may be used as well.

Where the cell containing the FPRL2 of the present invention is used in the screening method of the present invention, the cell may be fixed with glutaraldehyde, formalin, etc. The fixation may be carried out by a publicly known method.

The cell containing the FPRL2 of the present invention refers to a host cell expressing FPRL2. Examples of such a host cell include *Escherichia coli*, *Bacillus subtilis*, yeast, insect cells, animal cells, etc.

The membrane fraction of the cell means a fraction abundant in cell membrane obtained by cell disruption and subsequent fractionation by publicly known methods. Cell disruption methods include cell squashing using a Potter-Elvehjem homogenizer, disruption using a Waring blender or Polytron (manufactured by Kinematica Inc.), disruption by ultrasonication, disruption by cell spraying through thin nozzles under an increased pressure using a French press, or the like. Cell membrane fractionation is effected mainly by fractionation using a centrifugal force, such as centrifugation for fractionation and density gradient centrifugation. For example, cell disruption fluid is centrifuged at a low speed (500 rpm to 3,000 rpm) for a short period of time (normally about 1 to about 10 minutes), the resulting supernatant is then centrifuged at a higher speed (15,000 rpm to 30,000 rpm) normally for 30 minutes to 2 hours. The precipitate thus obtained is used as the membrane fraction. The membrane fraction is rich in the FPRL2 expressed and membrane components such as cell-derived phospholipids, membrane proteins, etc.

The amount of FPRL2 in a cell containing FPRL2 or a membrane fraction of the cell is preferably $10^3$ to $10^8$ molecules per cell, more preferably $10^5$ to $10^7$ molecules per cell. As the level of expression increases, the ligand binding activity per membrane fraction (specific activity) increases so that not only the highly sensitive screening system can be constructed but also large quantities of samples can be assayed with the same lot.

To perform a) through c) above for screening the compound that changes the binding property of the ligand peptide to the FPRL2 of the present invention or signal transduction, an appropriate FPRL2 fraction and a labeled ligand peptide are required.

The FPRL2 fraction is preferably a fraction of naturally occurring FPRL2 or a fraction of recombinant FPRL2 having an activity equivalent thereto. Herein, the equivalent activity is intended to mean a ligand binding activity, a signal transduction activity, etc.

As the labeled ligand peptide, there are used ligand peptides labeled with, e.g., $[^3H]$, $[^{125}I]$, $[^{14}C]$ $[^{35}S]$, etc.

Specifically, the compound that changes the binding property of the ligand peptide to the FPRL2 of the present invention or signal transduction is screened by the following procedures. First, standard FPRL2 is prepared by suspending a cell containing the FPRL2 of the present invention or a membrane fraction of the cell in a buffer appropriate for use in the screening method. Any buffer can be used so long as it does not interfere with the binding affinity of the ligand peptide to FPRL2, including a phosphate buffer or a Tris-HCl buffer, having pH of 4 to 10 (preferably pH of 6 to 8). For the purpose of minimizing non-specific binding, a surfactant such as CHAPS, Tween-80™ (Kao-Atlas Inc.), digitonin, deoxycholate, etc., may optionally be added to the buffer. Further for the purpose of suppressing the degradation of the receptor protein or ligand by a protease, a protease inhibitor such as PMSF, leupeptin, E-64 (manufactured by Peptide Institute, Inc.), pepstatin, etc. may also be added. A given amount (5,000 cpm to 500,000 cpm) of labeled ligand peptide is added to 0.01 ml to 10 ml of the receptor protein solution, in which $10^{-4}$ M to $10^{-10}$ M of a test compound is co-present. To determine the amount of non-specific binding (NSB), a reaction tube containing unlabeled ligand peptide in a large excess is also provided. The reaction is carried out at approximately 0° C. to 50° C., preferably approximately 4° C. to 37° C. for about 20 minutes to about 24 hours, preferably about 30 minutes to 3 hours. After completion of the reaction, the reaction mixture is filtrated through glass fiber filter paper, etc. and washed with an appropriate volume of the same buffer. The residual radioactivity on the glass fiber filter paper is then measured by means of a liquid scintillation counter or γ-counter. When nonspecific binding (NSB) is subtracted from the count ($B_0$) where any antagonizing substance is absent and the resulting count ($B_0$ minus NSB) is made 100%, the test compound showing the specific binding amount (B minus NSB) of, e.g., 50% or less may be selected as a candidate compound.

The method d) or e) described above for screening the compound that changes the binding property of the ligand peptide to the FPRL2 of the present invention or signal transduction can be performed as follows. For example, a FPRL2-mediated cell stimulating activity can be determined by a publicly known method, or using an assay kit commercially available.

Specifically, the cells containing the FPRL2 of the present invention are first cultured in a multiwell plate, etc. Prior to screening, the medium is replaced with fresh medium or with an appropriate non-cytotoxic buffer, followed by incubation for a given period of time in the presence of a test compound, etc. Subsequently, the cells are extracted or the supernatant is recovered and the resulting product is quantified by appropriate procedures. Where it is difficult to detect the production of the cell stimulating activity indicator (e.g., arachidonic acid, cAMP, etc.) due to a degrading enzyme contained in the cells, an inhibitor against such as a degrading enzyme may be added prior to the assay. For detecting the activities such as the cAMP production suppression activity, the baseline production in the cells is increased by forskolin or the like and the suppressing effect on the increased baseline production can be detected.

For screening by assaying the cell stimulating activity, cells wherein appropriate FPRL2 has been expressed are required. Preferred cells, in which the FPRL2 of the present invention has been expressed, are a cell line containing the FPRL2 of the present invention of naturally occurring type and the aforesaid cell line, in which FPRL2 of recombinant type has been expressed.

Examples of the test compounds include peptides, proteins, non-peptide compounds, synthetic compounds, fermentation products, cell extracts, plant extracts, animal tissue extracts, blood plasma, etc. These test compounds may be either novel or publicly known compounds.

The test compound may form salts and may be used in the form of salts with physiologically acceptable acids (e.g., inorganic acids, etc.) or bases (e.g., organic acids, etc.), preferably in the form of physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid. tartaric acid, citric acid, malic acid, oxalic acid, benzoic acid, methanesulfonic acid, benzenesulfonic acid, etc.) and the like.

The test compound which is preferably used is a compound designed to bind to the ligand-binding pocket, based on the atomic coordinate and the position of the ligand-binding pocket in the active site of the FPRL2 of the present invention. The atomic coordinate and the position of the ligand-binding pocket in the active site of the FPRL2 of the present invention can be determined by publicly known methods or modifications thereof.

The kit for screening a compound or its salt that changes the binding property of the ligand peptide to the FPRL2 of the present invention or signal transduction is a kit comprising the FPRL2 of the present invention, a cell containing the FPRL2 of the present invention, or a membrane fraction of the cell containing the FPRL2 of the present invention, and the like.

Examples of the screening kit of the present invention include the following.

1. Reagent for Screening a) Assay Buffer and Wash Buffer

Hanks' balanced salt solution (manufactured by Gibco, Inc.) supplemented with 0.05% bovine serum albumin (manufactured by Sigma, Inc.)

The solution is sterilized by filtration through a 0.45 μm filter, and stored at 4° C. or may be prepared at use.

b) FPRL2 Preparation

CHO cells wherein the FPRL2 of the present invention has been expressed are passaged in a 12-well plate at a density of $5 \times 10^5$ cells/well followed by culturing at 37° C. under 5% $CO_2$ and 95% air for 2 days.

c) Labeled Ligand Peptide

An aqueous solution of ligand peptide labeled with commercially available [$^3$H], [$^{125}$I], [$^{14}$C], [$^{35}$S], etc. is stored at 4° C. or −20° C., and diluted to 1 μM with the assay buffer upon use.

d) Standard Solution of Ligand Peptide

The ligand peptide is dissolved in and adjusted to 1 mM with PBS containing 0.1% bovine serum albumin (manufactured by Sigma, Inc.) and stored at −20° C.

2. Assay Method a) CHO cells wherein the FPRL2 of the present invention has been expressed are cultured in a 12-well culture plate and washed twice with 1 ml of the assay buffer, and 490 μl of the assay buffer is added to each well.

b) After adding 5 μl of $10^{-3}$-$10^{-10}$ M test compound solution, 5 μl of labeled ligand peptide is added to the mixture, and the cells are incubated at room temperature for an hour. To determine the amount of the non-specific binding, 5 μl of ligand peptide is added in place of the test compound.

c) The reaction solution is removed, and the wells are washed 3 times with the washing buffer. The labeled ligand bound to the cells is dissolved in 0.2N NaOH-1% SDS, and mixed with 4 ml of liquid scintillator A (manufactured by Wako Pure Chemical Industries, Ltd.)

d) The radioactivity is measured using a liquid scintillation counter (manufactured by Beckman Co.), and the percent maximum binding (PMB) is calculated by the equation below.

$$PMB = [(B-NSB)/(B_0-NSB)] \times 100$$

PMB: Percent maximum binding
B: Value obtained in the presence of a test compound
NSB: Non-specific binding
$B_0$: Maximum binding To evaluate specifically whether the compound is an agonist for or an antagonist to FPRL2, it is determined by (i) or (ii) below.

(i) The screening methods of a) to c) described above are performed to obtain the compound that changes the binding property of the ligand peptide to the FPRL2 of the present invention (especially inhibits the binding). Then, it is determined whether or not the compound possesses the cell stimulating activity described above. The compound having the cell stimulating activity or its salt is an agonist for the FPRL2 of the present invention, whereas the compound having no cell stimulating activity or its salt is an antagonist to the FPRL2 of the present invention.

(ii) (a) A test compound is brought in contact with a cell containing the FPRL2 of the present invention to assay the cell stimulating activity described above. The compound having the cell stimulating activity or its salt is an agonist for the FPRL2 of the present invention.

(b) The cell stimulating activity mediated by the FPRL2 of the present invention are assayed in the case wherein a compound that activates the FPRL2 of the present invention (e.g., a ligand) is brought in contact with a cell containing the FPRL2 of the present invention and in the case wherein a compound that activates the FPRL2 of the present invention and a test compound are brought in contact with a cell containing the FPRL2 of the present invention, and comparison is made therebetween. The compound, which can decrease the cell stimulating activity mediated by the compound that activates the FPRL2 of the present invention or its salt, is an antagonist to the FPRL2 of the present invention.

The compound or its salt, which is obtained by using the screening methods or the screening kits of the present invention, is the compound that changes the binding property of the ligand peptide to the FPRL2 of the present invention or signal transduction. Specifically, the compound is: (a) a compound having the receptor-mediated cell stimulating activity (a so-called agonist for the FPRL2 of the present invention); (b) a compound having no cell stimulating activity (a so-called antagonist to the FPRL2 of the present invention); (c) a compound that potentiates the binding affinity of the ligand peptide to the FPRL2 of the present invention; or (d) a compound that reduces the binding affinity of the ligand peptide to the FPRL2 of the present invention.

These test compounds may be peptides, proteins, non-peptide compounds, synthetic compounds, fermentation products, blood plasma, and may be novel or known compounds.

The compound or its salt obtained by using the screening methods or screening kits of the present invention, especially the agonist (including the ligand peptide), or the compound or its salt that potentiates the binding affinity of the ligand peptide to the FPRL2 of the present invention can be used as a low-toxic and safe drug, including an agent for preventing/treating, for example, asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as, cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endotoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, immunodeficiency, infections, cancer, etc., especially immunodeficiency.

On the other hand, the antagonist or the compound or its salt that reduces the binding affinity of the ligand peptide to the FPRL2 of the present invention, which is obtained by using the screening methods described above, can be used as drugs for diseases caused by overexpression of the FPRL2 of the present invention, for example, asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as, cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endotoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, infections, cancer, etc., especially, asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as, cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endotoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, infections, cancer, etc.

Where the compound or its salt, which is obtained by using the screening methods or screening kits of the present invention, is used as the pharmaceutical composition described above, the compound or its salt can be prepared into a pharmaceutical preparation in a conventional manner.

For example, the compound can be used orally in the form of tablets which may be tablets, if necessary, coated with sugar, capsules, elixirs, microcapsules, etc., or parenterally in the form of injectable preparations such as a sterile solution or a suspension in water or with other pharmaceutically acceptable liquid. These preparations can be manufactured, e.g., by mixing the compound, with a physiologically acceptable known carrier, flavoring agent, excipient, vehicle, antiseptic, stabilizer, binder, etc., in a unit dosage form required in a generally accepted manner applied to making pharmaceutical preparations. The active ingredient in the preparation is controlled in such an amount that an appropriate dose is obtained within the specified range given.

Additives miscible with tablets, capsules, etc. include a binder such as gelatin, cornstarch, tragacanth or gum arabic, an excipient such as crystalline cellulose, a swelling agent such as cornstarch, gelatin, alginic acid, etc., a lubricant such as magnesium stearate, a sweetening agent such as sucrose, lactose or saccharin, a flavoring agent such as peppermint, akamono oil or cherry, and the like. When the unit dosage is in the form of capsules, liquid carriers such as oils and fats may further be used together with the additives described above. A sterile composition for injection may be formulated following a conventional manner used to make pharmaceutical compositions, e.g., by dissolving or suspending the active ingredients in a vehicle such as water for injection with a naturally occurring vegetable oil such as sesame oil, coconut oil, etc. to prepare the pharmaceutical composition. Examples of an aqueous medium for injection include physiological saline, an isotonic solution containing glucose and other auxiliary agents (e.g., D-sorbitol, D-mannitol, sodium chloride, etc.) or the like, which may be used in combination with an appropriate dissolution aid such as an alcohol (e.g., ethanol), a polyalcohol (e.g., propylene glycol, polyethylene glycol), a nonionic surfactant (e.g., polysorbate 80™ and HCO-50), etc. As an oily medium, for example, sesame oil, soybean oil or the like may be used, and may be used in combination with a dissolution aid such as benzyl benzoate, benzyl alcohol, etc.

Furthermore, the preventive/therapeutic agent described above may also be formulated with a buffer (e.g., phosphate buffer, sodium acetate buffer), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

Since the thus obtained pharmaceutical preparation is safe and low toxic, the preparation can be administered to human or mammals (e.g., rats, mice, rabbits, sheep, swine, bovine, cats, dogs, monkeys, etc.).

The dose of the compound or its salt may vary depending on subject to be administered, target organ, conditions, methods for administration, etc.; in oral administration, the agonist is administered to the patient (as 60 kg body weight) with immunodeficiency normally in a dose of about 0.1 mg to about 100 mg, preferably about 1.0 to about 50 mg, and more preferably about 1.0 to about 20 mg per day. In parenteral administration, the single dose may vary depending on subject to be administered, target organ, conditions, method for administration, etc. For instance, in the form of injection, it is advantageous to administer the agonist intravenously to the patient (as 60 kg body weight) with immunodeficiency in a daily dose of about 0.01 to about 30 mg, preferably about 0.1 to about 20 mg, and more preferably about 0.1 to about 10 mg. For other animal species, the corresponding dose as converted per 60 kg body weight can be administered.

(7) Methods for Elucidation of the Working Mechanism of Various Drugs

By using FPRL2, it can be confirmed whether or not various drugs exhibit their pharmacological effects mediated by FPRL2.

That is, the present invention provides the following methods:

(1) A method of confirmation that an agent for preventing/treating asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as, cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endotoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, immunodeficiency, infections or cancer binds to the receptor protein or a salt thereof, which is characterized by using FPRL2;

(2) A method of confirmation that the agent for preventing/treating immunodeficiency is an agonist for the receptor protein or a salt thereof, which is characterized by using FPRL2;

(3) A method of confirmation that the agent for preventing/treating asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as, cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endotoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, infections or cancer is an antagonist to the receptor protein or a salt thereof, which is characterized by using FPRL2; and (4) The screening method according to (1) through (3), which is characterized by measuring the binding amount of each drug to FPRL2 when the drug is brought in contact with FPRL2.

This confirmation method can be performed by using the drug described above instead of the test compound in the aforesaid method of screening the compound that changes the binding property of the ligand peptide to FPRL2.

The kit for the confirmation method of the present invention comprises the drug described above in place of the test compound, in the aforesaid kit for screening the compound that changes the binding property of the ligand peptide to FPRL2.

By using the confirmation method of the present invention as above, it can be confirmed that various drugs commercially available or under development exhibit FPRL2-mediated pharmacological effects.

(8) Pharmaceutical Comprising the Compound or its Salt that Changes the Amount of the FPRL2 of the Present Invention or its Partial Peptide in Cell Membrane The antibody of the present invention is capable of specifically recognizing the FPRL2 of the present invention and can be used for screening the compound or its salt that changes the amount of the FPRL2 of the present invention in a cell membrane.

That is, the present invention provides the following methods:

(i) a method of screening the compound or its salt that changes the amount of the FPRL2 of the present invention in a cell membrane, which comprises quantifying the FPRL2 of the present invention contained in a) blood, b) particular organs or c) a cell membrane fraction isolated after disrupting tissues or cells isolated from the organs of non-human mammals;

(ii) a method of screening the compound or its salt that changes the amount of the FPRL2 of the present invention in a cell membrane, which comprises disrupting transformants, which expresses the FPRL2 of the present invention, isolating the cell membrane fraction and quantifying the FPRL2 of the present invention contained in the cell membrane fraction; and, (iii) a method of screening the compound or its salt that changes the amount of the FPRL2 of the present invention in a cell membrane, which comprises preparing a section of a) blood, b) particular organs or c) tissues, cells, etc. isolated from organs of non-human mammals and quantifying the stained receptor protein on the cell surface using immunostaining assay thereby to confirm the protein on the cell membrane.

The present invention also provides:

(iv) a method of screening the compound or its salt that changes the amount of the FPRL2 of the present invention in a cell membrane, which comprises preparing a section of transformant expressing the FPRL2 of the present invention and quantifying the stained receptor protein on the cell surface using immunostaining assay thereby to confirm the protein on the cell membrane.

Specifically, the FPRL2 of the present invention contained in the cell membrane fraction can be quantified as follows.

(i) Normal or disease models of non-human mammals (e.g., mice, rats, rabbits, sheep, swine, bovine, cats, dogs, monkeys, more specifically, rats, mice or rabbits of Alzheimer's disease model, etc.) receive a drug (e.g., an immunomodulator, etc.) or physical stress (e.g., soaking stress, electric shock, light and darkness, low temperature, etc.), and the blood, specific organs (e.g., brain, liver, kidney, etc.), or tissues or cells isolated from the organs are obtained after a specified period of time. The obtained organs, tissues, cells or the like are suspended in, for example, an appropriate buffer (e.g., Tris hydrochloride buffer, phosphate buffer, HEPES buffer, etc.), and the organs, tissues or cells are disrupted, and the cell membrane fraction is obtained using surfactants (e.g., Triton-X 100™, Tween 20™) and further using techniques such as centrifugal separation, filtration, column fractionation, etc.

The membrane fraction of the cell means a fraction abundant in cell membrane obtained by cell disruption and subsequent fractionation by publicly known methods. Cell disruption methods include cell squashing using a Potter-Elvehjem homogenizer, disruption using a Waring blender or Polytron (manufactured by Kinematica Inc.), disruption by ultrasonication, disruption by cell spraying through thin nozzles under an increased pressure using a French press, or the like. Cell membrane fractionation is effected mainly by fractionation using a centrifugal force, such as centrifugation for fractionation and density gradient centrifugation. For example, cell disruption fluid is centrifuged at a low speed (500 rpm to 3,000 rpm) for a short period of time (normally about 1 to about 10 minutes), the resulting supernatant is then centrifuged at a higher speed (15,000 rpm to 30,000 rpm) normally for 30 minutes to 2 hours. The precipitate thus obtained is used as the membrane fraction. The membrane fraction is rich in the FPRL2 expressed and membrane components such as cell-derived phospholipids, membrane proteins, etc.

The FPRL2 of the present invention contained in a cell membrane fraction can be quantified by, for example, the sandwich immunoassay, western blot analysis, etc., using the antibody of the present invention.

The sandwich immunoassay can be performed as described above, and the western blot can be performed by publicly known methods.

(ii) Transformants expressing the FPRL2 of the present invention are prepared by the method described above, and the FPRL2 of the present invention contained in the cell membrane fraction can be quantified.

The compound or its salt that changes the amount of the FPRL2 of the present invention in cell membranes can be screened as follows:

(i) Normal non-human mammals or disease models of non-human mammals are administered with a test compound at a specified period of time before (30 minutes to 24 hours before, preferably 30 minutes to 12 hours before, more preferably 1 hour to 6 hours before), at a specified time after (30 minutes to 3 days after, preferably 1 hour to 2 days after, more preferably 1 hour to 24 hours after), or simultaneously with a drug or physical stress. At a specified time (30 minute to 3 days, preferably 1 hour to 2 days, more preferably 1 hour to 24 hours) after administration of the test compound, the amount of the FPRL2 of the present invention in the cell membranes can be quantified; and (ii) Transformants are cultured in a conventional manner and a test compound is mixed in the culture medium. After a specified time (after 1 day to 7 days, preferably after 1 day to 3 days, more preferably after 2 to 3 days), the amount of the FPRL2 of the present invention in the cell membranes can be quantified.

Specifically, the FPRL2 of the present invention contained in cell membrane fractions is confirmed as follows.

(iii) Normal non-human mammals or disease models of non-human mammals (e.g., mice, rats, rabbits, sheep, swine, bovine, cats, dogs, monkeys, etc., more specifically, rats, mice or rabbits of Alzheimer's disease model, etc.) receive a drug (e.g., an immunomodulator, etc.) or physical stress (e.g., soaking stress, electric shock, light and darkness, low temperature, etc.) or the like, and blood or particular organ (e.g., brain, liver, kidney, etc.), or the tissues or cells isolated from the organ are obtained after a specified period of time. Tissue sections are prepared from the thus obtained organs, tissues, cells, etc. in a conventional manner followed by immunostaining with the antibody of the present invention. The staining intensity of the receptor protein on the cell surface is quantified to confirm the protein on the cell membrane, whereby the amount of the FPRL2 of the present invention on the cell membrane can be confirmed quantitatively or qualitatively.

(iv) The confirmation can also be made in a similar manner, using a transformant expressing the FPRL2 of the present invention.

The compounds or its salts obtained by the screening methods of the present invention are compounds that have the action of changing the amount of the FPRL2 of the present invention in cell membranes. Specifically, these compounds are: (a) compounds that increase the amount of the FPRL2 of the present invention in cell membranes thereby to potentiate the FPRL2-mediated cell stimulating activity (e.g., the activity that promotes or suppresses arachidonic acid release, acetylcholine release, intracellular $Ca^{2+}$ release, intracellular cAMP production, intracellular cAMP production inhibition, intracellular cGMP production, inositol phosphate production, changes in cell membrane potential, phosphorylation of intracellular proteins, activation of c-fos, pH reduction, etc.) and (b) compounds that decrease the amount of the FPRL2 of the present invention in the cell membranes thereby to attenuate the cell stimulating activity.

The compounds may be peptides, proteins, non-peptide compounds, synthetic compounds, fermentation products, and may be novel or publicly known compounds.

As salts of the compounds there may be used salts with physiologically acceptable acids (e.g., inorganic acids, etc.) or bases (e.g., organic acids, etc.), preferably in the form of physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

The compound or its salts that increase the amount of the FPRL2 of the present invention in cell membranes thereby to enhance the cell stimulating activity can be used for low toxic and safe drugs such as agents for preventing/treating diseases associated with dysfunction of the FPRL2 of the present invention. Specifically, the compound or its salts can be used as a low-toxic and safe drug, including an agent for preventing/treating asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as, cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, immunodeficiency, infections, cancer, etc., especially immunodeficiency.

On the other hand, the compound or its salts that attenuates the cell stimulating activity by decreasing the amount of the FPRL2 of the present invention in cell membrane are useful as safe and low toxic drugs for diseases caused by overexpression of the FPRL2 of the present invention, for example, asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as, cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endotoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, immunodeficiency, infections, cancer, etc., especially asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as, cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endotoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, infections or cancer.

Where the compound or its salts obtained by using the screening methods of the present invention is used as a pharmaceutical composition, the compound or its salt can be prepared into a pharmaceutical preparation in a conventional manner.

For example, the compound or its salts can be used orally in the form of tablets which may be tablets, if necessary, coated with sugar, capsules, elixirs, microcapsules, etc., or parenterally in the form of injectable preparations such as a sterile solution or a suspension in water or with other pharmaceutically acceptable liquid. These preparations can be manufactured, e.g., by mixing the compound or its salts, with a physiologically acceptable known carrier, flavoring agent, excipient, vehicle, antiseptic, stabilizer, binder, etc., in a unit dosage form required in a generally accepted manner applied to making pharmaceutical preparations. The active ingredient in the preparation is controlled in such an amount that an appropriate dose is obtained within the specified range given.

Additives miscible with tablets, capsules, etc. include a binder such as gelatin, cornstarch, tragacanth or gum arabic, an excipient such as crystalline cellulose, a swelling agent such as cornstarch, gelatin, alginic acid, etc., a lubricant such as magnesium stearate, a sweetening agent such as sucrose, lactose or saccharin, a flavoring agent such as peppermint, akamono oil or cherry, and the like. When the unit dosage is in the form of capsules, liquid carriers such as oils and fats may further be used together with the additives described above. A sterile composition for injection may be formulated following a conventional manner used to make pharmaceutical compositions, e.g., by dissolving or suspending the active ingredients in a vehicle such as water for injection with a naturally occurring vegetable oil such as sesame oil, coconut oil, etc. to prepare the pharmaceutical composition. Examples of an aqueous medium for injection include physiological saline, an isotonic solution containing glucose and other auxiliary agents (e.g., D-sorbitol, D-mannitol, sodium chloride, etc.) or the like, which may be used in combination with an appropriate dissolution aid such as an alcohol (e.g., ethanol), a polyalcohol (e.g., propylene glycol, polyethylene glycol), a nonionic surfactant (e.g., polysorbate 80™ and HCO-50), etc. As an oily medium, for example, sesame oil, soybean oil or the like may be used, which can be used in combination with a dissolution aid such as benzyl benzoate, benzyl alcohol, etc.

Furthermore, the preventive/therapeutic agent described above may also be formulated with a buffer (e.g., phosphate buffer, sodium acetate buffer), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

Since the thus obtained pharmaceutical preparation is safe and low toxic, the preparation can be administered to human or mammals (e.g., rats, mice, rabbits, sheep, swine, bovine, cats, dogs, monkeys, etc.).

The dose of the compound or its salt may vary depending on subject to be administered, target organ, conditions, methods for administration, etc.; in oral administration, the compound that increases the amount of the FPRL2 of the present invention in cell membrane is administered to the patient (as 60 kg body weight) with immunodeficiency normally in a dose of about 0.1 mg to about 100 mg, preferably about 1.0 to about 50 mg, and more preferably about 1.0 to about 20 mg per day. In parenteral administration, the single dose may vary depending on subject to be administered, target organ, conditions, methods for administration, etc. In the form of injection, the compound that increases the amount of the FPRL2 of the present invention in cell membranes is advantageously administered intravenously to the patient (as 60 kg body weight) with immunodeficiency in a daily dose of about 0.01 to about 30 mg, preferably about 0.1 to about 20 mg, and more preferably about 0.1 to about 10 mg. For other animal species, the corresponding dose as converted per 60 kg body weight can be administered.

(9) Pharmaceutical Comprising the Antibody to the FPRL2 of the Present Invention The neutralizing activity of the antibody to the FPRL2 of the present invention means the activity of inactivating the signal transduction function in which said FPRL2 takes part. Thus, when the antibody has the neutralizing activity, the antibody can inactivate signal transduction in which said FPRL2 takes part, for example, the cell stimulating activity mediated by said FPRL2 (e.g., the activities that promote or suppress arachidonic acid release, acetylcholine release, intracellular $Ca^{2+}$ release, intracellular cAMP production, intracellular cAMP production inhibition, intracellular cGMP production, inositol phosphate production, changes in cell membrane potential, phosphorylation of intracellular proteins, activation of c-fos, pH reduction, etc.).

Therefore, the neutralizing antibody to the FPRL2 of the present invention can be used as an agent for preventing/treating diseases caused by overexpression of the FPRL2 or overexpression of the ligand peptide, for example, asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as, cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, immunodeficiency, infections, cancer, etc., especially asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as, cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, infections or cancer.

The preventive/therapeutic agents described above can be manufactured in a manner similar to the method for preparing the pharmaceuticals comprising the FPRL2 of the present invention described above.

The dose of the antibody may vary depending on subject to be administered, target organ, conditions, methods for administration, etc. in parenteral administration, e.g., in the form of an injection, it is advantageous to administer the antibody intravenously to the patient (as 60 kg body weight) with inflammation in a daily dose of about 0.01 to about 30 mg, preferably about 0.1 to about 20 mg, and more preferably about 0.1 to about 10 mg. For other animal species, the corresponding dose as converted per 60 kg body weight can be administered.

(10) Pharmaceutical Comprising the Antisense DNA of the Present Invention

The antisense DNA of the present invention can be used as an agent for preventing/treating diseases caused by overexpression of the FPRL2 or overexpression of the ligand peptide, for example, asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endotoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, immunodeficiency, infections, cancer, etc., especially asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endotoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, infections, cancer, etc.

For example, where the antisense DNA is used, the antisense DNA itself is administered; alternatively, the antisense DNA is inserted into an appropriate vector such as retrovirus vector, adenovirus vector, adenovirus-associated virus vector, etc. and then administered in a conventional manner. The antisense DNA may also be administered as naked, or with adjuvants to assist its uptake by gene gun or through a catheter such as a catheter with a hydrogel.

In addition, the antisense DNA may also be used as an oligonucleotide probe for diagnosis to investigate the presence of the DNA of the present invention or the state of its expression in tissues or cells.

(11) Preparation of Animal Bearing the DNA of the Present Invention

The present invention provides a non-human mammal bearing DNA of the present invention which is exogenous (hereinafter briefly referred to as the exogenous DNA of the present invention) or its variant DNA (sometimes briefly referred to as the exogenous variant DNA of the present invention).

That is, the present invention provides:

[1] A non-human mammal bearing the exogenous DNA of the present invention or its variant DNA;

[2] The mammal according to [1], wherein the non-human mammal is a rodent;

[3] The mammal according to [2], wherein the rodent is mouse or rat; and,

[4] A recombinant vector containing the exogenous DNA of the present invention or its variant DNA and capable of expressing in a mammal; etc.

The non-human mammal bearing the exogenous DNA of the present invention or its variant DNA (hereinafter briefly referred to as the DNA transgenic animal of the present invention) can be prepared by transferring a desired DNA into an unfertilized egg, a fertilized egg, a spermatozoon, a germinal cell containing a primordial germinal cell thereof, or the like, preferably in the embryogenic stage in the development of a non-human mammal (more preferably in the single cell or fertilized cell stage and generally before the 8-cell phase) by standard means, such as the calcium phosphate method, the electric pulse method, the lipofection method, the agglutination method, the microinjection method, the particle gun method, the DEAE-dextran method, etc. Also, it is possible to transfer the exogenous DNA of the present invention into a somatic cell, a living organ, a tissue cell, or the like by the DNA transfer, and utilize the transformant for cell culture, tissue culture, etc. In addition, these cells may be fused with the above-described germinal cell by a publicly known cell fusion method to prepare the DNA transgenic animal of the present invention.

Examples of the non-human mammal that can be used include bovine, swine, sheep, goat, rabbits, dogs, cats, guinea pigs, hamsters, mice, rats, etc. Above all, preferred are rodents, especially mice (e.g., C57Bl/6 strain, DBA2 strain, etc. for a pure line and for a cross line, B6C3F$_1$ strain, BDF$_1$ strain B6D2F$_1$ strain, BALB/c strain, ICR strain, etc.), rats (Wistar, SD, etc.) or the like, since they are relatively short in ontogeny and life cycle from a standpoint of producing model animals for human disease.

"Mammals" in a recombinant vector that can be expressed in the mammals include the aforesaid non-human mammals and human.

The exogenous DNA of the present invention refers to the DNA of the present invention that is once isolated and extracted from mammals, not the DNA of the present invention inherently possessed by the non-human mammals.

The mutant DNA of the present invention includes mutants resulting from variation (e.g., mutation, etc.) in the base sequence of the original DNA of the present invention, specifically DNAs resulting from base addition, deletion, substitution with other bases, etc. and further including abnormal DNA.

The abnormal DNA is intended to mean DNA that expresses abnormal FPRL2 of the present invention and exemplified by the DNA that expresses FPRL2 for suppressing the function of normal FPRL2 of the present invention.

The exogenous DNA of the present invention may be any one of those derived from a mammal of the same species as, or a different species from, the mammal as the target animal. In transferring the DNA of the present invention, it is generally advantageous to use the DNA as a DNA construct in which the DNA is ligated downstream a promoter capable of expressing the DNA in the target animal. For example, in the case of transferring the human DNA of the present invention, a DNA transgenic mammal that expresses the DNA of the present invention to a high level, can be prepared by microinjecting a DNA construct (e.g., vector, etc.) ligated with the human DNA of the present invention into a fertilized egg of the target non-human mammal downstream various promoters which are capable of expressing the DNA derived from various mammals (e.g., rabbits, dogs, cats, guinea pigs, hamsters, rats, mice, etc.) bearing the DNA of the present invention highly homologous to the human DNA.

As expression vectors for the FPRL2 of the present invention, there are *Escherichia coli*-derived plasmids, *Bacillus subtilis*-derived plasmids, yeast-derived plasmids, bacteriophages such as λ phage, retroviruses such as Moloney leukemia virus, etc., and animal viruses such as vaccinia virus, baculovirus, etc. Of these vectors, *Escherichia coli*-derived plasmids, *Bacillus subtilis*-derived plasmids, or yeast-derived plasmids, etc. are preferably used.

Examples of these promoters for regulating the DNA expression include (i) promoters for DNA derived from viruses (e.g., simian virus, cytomegalovirus, Moloney leukemia virus, JC virus, breast cancer virus, poliovirus, etc.), and (ii) promoters derived from various mammals (human, rabbits, dogs, cats, guinea pigs, hamsters, rats, mice, etc.), for example, promoters of albumin, insulin II, uroplakin II, elastase, erythropoietin, endothelin, muscular creatine kinase, glial fibrillary acidic protein, glutathione S-transferase, platelet-derived growth factor β, keratins K1, K10 and K14, collagen types I and II, cyclic AMP-dependent protein kinase βI subunit, dystrophin, tartarate-resistant alkaline phosphatase, atrial natriuretic factor, endothelial receptor tyrosine kinase (generally abbreviated as Tie2), sodium-potassium adenosine triphosphorylase (Na,K-ATPase), neurofilament light chain, metallothioneins I and IIA, metalloproteinase I tissue inhibitor, MHC class I antigen (H-2L), H-ras, renin, dopamine β-hydroxylase, thyroid peroxidase (TPO), protein chain elongation factor 1α (EF-1α), β actin, α and β myosin heavy chains, myosin light chains 1 and 2, myelin base protein, thyroglobulins, Thy-1, immunoglobulins, H-chain variable region (VNP), serum amyloid component P, myoglobin, troponin C, smooth muscle α actin, preproencephalin A, vasopressin, etc. Among them, cytomegalovirus promoters, human protein elongation factor 1α (EF-1α) promoters, human and fowl β actin promoters, etc., which are capable of high expression in the whole body are preferred.

Preferably, the vectors described above have a sequence that terminates the transcription of the desired messenger RNA in the DNA transgenic animal (generally termed a terminator); for example, a sequence of each DNA derived from viruses and various mammals, and SV40 terminator of the simian virus and the like are preferably used.

In addition, for the purpose of increasing the expression of the desired exogenous DNA to a higher level, the splicing signal and enhancer region of each DNA, a portion of the intron of an eukaryotic DNA may also be ligated at the 5' upstream of the promoter region, or between the promoter region and the translational region, or at the 3' downstream of the translational region, depending upon purposes.

The translational region for normal FPRL2 of the present invention can be obtained using as a starting material the entire genomic DNA or its portion of liver, kidney, thyroid cell or fibroblast origin from human or various mammals (e.g., rabbits, dogs, cats, guinea pigs, hamsters, rats, mice, etc.) or of various commercially available genomic DNA libraries, or using cDNA prepared by a publicly known method from RNA of liver, kidney, thyroid cell or fibroblast origin as a starting material. Also, an exogenous abnormal DNA can produce the translational region through variation of the translational region of normal FPRL2 obtained from the cells or tissues described above by point mutagenesis.

The translational region can be prepared by a conventional DNA engineering technique, in which the DNA is ligated downstream the aforesaid promoter and if desired, upstream the translation termination site, as a DNA construct capable of being expressed in the transgenic animal.

The exogenous DNA of the present invention is transferred at the fertilized egg cell stage in a manner such that the DNA is certainly present in all the germinal cells and somatic cells of the target mammal. The fact that the exogenous DNA of the present invention is present in the germinal cells of the animal prepared by DNA transfer means that all offspring of the prepared animal will maintain the exogenous DNA of the present invention in all of the germinal cells and somatic cells thereof. The offspring of the animal that inherits the exogenous DNA of the present invention also have the exogenous DNA of the present invention in all of the germinal cells and somatic cells thereof.

The non-human mammal in which the normal exogenous DNA of the present invention has been transferred can be passaged as the DNA-bearing animal under ordinary rearing environment, by confirming that the exogenous DNA is stably maintained by crossing.

By transfer of the exogenous DNA of the present invention at the fertilized egg cell stage, the DNA is retained to be excess in all of the germinal and somatic cells. The fact that the exogenous DNA of the present invention is excessively present in the germinal cells of the prepared animal after transfer means that the DNA of the present invention is excessively present in all of the germinal cells and somatic cells thereof. The offspring of the animal that inherits the exogenous DNA of the present invention have excessively the DNA of the present invention in all of the germinal cells and somatic cells thereof.

It is possible to obtain homozygous animals having the transferred DNA in both homologous chromosomes and breed male and female of the animal so that all the progeny have this DNA in excess.

In a non-human mammal bearing the normal DNA of the present invention, the normal DNA of the present invention has expressed at a high level, and may eventually develop hyperfunction in the function of the FPRL2 of the present invention by accelerating the function of endogenous normal DNA. Therefore, the animal can be utilized as a pathologic model animal for such a disease. For example, using the normal DNA transgenic animal of the present invention, it is possible to elucidate the mechanism of hyperfunction in the function of the FPRL2 of the present invention and the pathological mechanism of the disease associated with the FPRL2 of the present invention and to investigate how to treat these diseases.

Furthermore, since a mammal transferred with the exogenous normal DNA of the present invention exhibits an increasing symptom of the FPRL2 of the present invention liberated, the animal is usable for screening of a drug for treating diseases associated with the FPRL2 of the present invention.

On the other hand, a non-human mammal having the exogenous abnormal DNA of the present invention can be passaged under normal breeding conditions as the DNA-bearing animal by confirming stable retention of the exogenous DNA via crossing. Furthermore, the exogenous DNA of interest can be utilized as a starting material by inserting the DNA into the plasmid described above. The DNA construct with a promoter can be prepared by conventional DNA engineering techniques. The transfer of the abnormal DNA of the present invention at the fertilized egg cell stage is preserved to be present in all of the germinal and somatic cells of the target mammal. The fact that the abnormal DNA of the present invention is present in the germinal cells of the animal after DNA transfer means that all of the offspring of the prepared animal have the abnormal DNA of the present invention in all of the germinal and somatic cells. Such an offspring that passaged the exogenous DNA of the present invention will have the abnormal DNA of the present invention in all of the germinal and somatic cells. A homozygous animal having the introduced DNA on both of homologous chromosomes can be acquired, and by crossing these male and female animals, all the offspring can be bred to retain the DNA.

In a non-human mammal bearing the abnormal DNA of the present invention, the abnormal DNA of the present invention has expressed to a high level, and may eventually develop the function inactive type inadaptability to the FPRL2 of the present invention by inhibiting the functions of endogenous normal DNA. Therefore, the animal can be utilized as a pathologic model animal for such a disease. For example, using the abnormal DNA transgenic animal of the present invention, it is possible to elucidate the mechanism of the function inactive type inadaptability to the FPRL2 of the present invention and the pathological mechanism of the disease and to investigate how to treat the disease.

More specifically, the transgenic animal overexpressing the abnormal DNA of the present invention at a high level is expected to serve as an experimental model to elucidate the mechanism of the functional inhibition (dominant negative effect) of a normal the FPRL2 by the abnormal the FPRL2 of the present invention in the function inactive type inadaptability of the FPRL2 of the present invention.

A mammal bearing the abnormal exogenous DNA of the present invention is also expected to serve for screening a candidate drug for treating the function inactive type inadaptability of the FPRL2 of the present invention, since a free form of the FPRL2 of the present invention is increased in such an animal.

Other potential applications of two kinds of the DNA transgenic animals of the present invention described above further include, for example:

(i) Use as a cell source for tissue culture;
(ii) Analysis of the relation to the FPRL2 that is specifically expressed or activated by the FPRL2, by direct analysis of DNA or RNA in tissues of the DNA transgenic animal of the present invention or by analysis of the FPRL2 tissues expressed by the DNA;
(iii) Research on the function of cells derived from tissues that are usually cultured only with difficulty, using cells in tissues bearing the DNA cultured by a standard tissue culture technique;
(iv) Screening a drug that enhances the functions of cells using the cells described in (iii) above; and,
(v) Isolation and purification of the variant the FPRL2 of the present invention and preparation of an antibody thereto.

Furthermore, clinical conditions of a disease associated wit the FPRL2 of the present invention, including the function inactive type inadaptability to the FPRL2 of the present invention can be determined by using the DNA transgenic animal of the present invention. Also, pathological findings on each organ in a disease model associated with the FPRL2 of the present invention can be obtained in more detail, leading to the development of a new method for treatment as well as the research and therapy of any secondary diseases associated with the disease.

It is also possible to obtain a free DNA-transferred cell by withdrawing each organ from the DNA transgenic animal of the present invention, mincing the organ and degrading with a proteinase such as trypsin, etc., followed by establishing the line of culturing or cultured cells. Furthermore, the DNA transgenic animal of the present invention can serve to identify cells capable of producing the FPRL2 of the present invention, and to study in association with apoptosis, differentiation or propagation or on the mechanism of signal transduction in these properties to inspect any abnormality therein. Thus, the DNA transgenic animal can provide an effective research material for the FPRL2 of the present invention and for investigation of the function and effect thereof.

To develop a drug for treating diseases associated with the FPRL2 of the present invention, including the function inactive type inadaptability to the FPRL2 of the present invention, using the DNA transgenic animal of the present invention, an effective and rapid method for screening can be provided by using the method for inspection and the method for quantification, etc. described above. It is also possible to investigate and develop a method for DNA therapy for treating diseases associated with the FPRL2 of the present invention, using the DNA transgenic animal of the present invention or a vector capable of expressing the exogenous DNA of the present invention.

(12) Knockout Animal

The present invention provides a non-human mammalian embryonic stem cell bearing the DNA of the present invention inactivated and a non-human mammal deficient in expressing the DNA of the present invention.

Thus, the present invention provides:

[1] A non-human mammalian embryonic stem cell in which the DNA of the present invention is inactivated;
[2] The embryonic stem cell according to [1], wherein the DNA is inactivated by introducing a reporter gene (e.g., β-galactosidase gene derived from *Escherichia coli*);

[3] The embryonic stem cell according to [1], which is resistant to neomycin;

[4] The embryonic stem cell according to [1], wherein the non-human mammal is a rodent;

[5] The embryonic stem cell according to [4], wherein the rodent is mouse;

[6] A non-human mammal deficient in expressing the DNA of the present invention, wherein the DNA is inactivated;

[7] The non-human mammal according to [6], wherein the DNA is inactivated by inserting a reporter gene (e.g., β-galactosidase derived from *Escherichia coli*) therein and the reporter gene is capable of being expressed under control of a promoter for the DNA of the present invention;

[8] The non-human mammal according to [6], which is a rodent;

[9] The non-human mammal according to [8], wherein the rodent is mouse; and,

[10] A method of screening a compound that promotes or inhibits (preferably inhibits) the promoter activity to the DNA of the present invention, which is characterized by administering a test compound to the mammal of [7] and detecting expression of the reporter gene.

The non-human mammal embryonic stem cell in which the DNA of the present invention is inactivated refers to a non-human mammal embryonic stem cell that suppresses the ability of the non-human mammal to express the DNA by artificially mutating the DNA of the present invention, or the DNA has no substantial ability to express the FPRL2 of the present invention (hereinafter sometimes referred to as the knockout DNA of the present invention) by substantially inactivating the activities of the FPRL2 of the present invention encoded by the DNA (hereinafter merely referred to as ES cell).

As the non-human mammal, the same examples as described above apply.

Techniques for artificially mutating the DNA of the present invention include deletion of a part or all of the DNA sequence and insertion of or substitution with other DNA, by genetic engineering. By these variations, the knockout DNA of the present invention may be prepared, for example, by shifting the reading frame of a codon or by disrupting the function of a promoter or exon.

Specifically, the non-human mammal embryonic stem cell in which the DNA of the present invention is inactivated (hereinafter merely referred to as the ES cell with the DNA of the present invention inactivated or the knockout ES cell of the present invention) can be obtained by, for example, isolating the DNA of the present invention that the desired non-human mammal possesses, inserting a DNA fragment having a DNA sequence constructed by inserting a drug resistant gene such as a neomycin resistant gene or a hygromycin resistant gene, or a reporter gene such as lacZ (β-galactosidase gene) or cat (chloramphenicol acetyltransferase gene), etc. into its exon region thereby to disable the functions of exon, or integrating to a chromosome of the target animal by, e.g., homologous recombination, a DNA sequence that terminates gene transcription (e.g., polyA additional signal, etc.) in the intron between exons, thus inhibiting the synthesis of complete messenger RNA and eventually destroying the gene (hereinafter briefly referred to as a targeting vector). The thus-obtained ES cells to the southern hybridization analysis with a DNA sequence on or near the DNA of the present invention as a probe, or to PCR analysis with a DNA sequence on the targeting vector and another DNA sequence near the DNA of the present invention which is not included in the targeting vector as primers, to select the knockout ES cell of the present invention.

The parent ES cells to inactivate the DNA of the present invention by homologous recombination, etc. may be of a strain already established as described above, or may originally be established in accordance with a modification of the known method by Evans and Kaufman described above. For example, in the case of mouse ES cells, currently it is common practice to use ES cells of the 129 strain. However, since their immunological background is obscure, the C57BL/6 mouse or the $BDF_1$ mouse ($F_1$ hybrid between C57BL/6 and DBA/2), wherein the low ovum availability per C57BL/6 in the C57BL/6 mouse has been improved by crossing with DBA/2, may be preferably used, instead of obtaining a pure line of ES cells with the clear immunological genetic background and for other purposes. The $BDF_1$ mouse is advantageous in that, when a pathologic model mouse is generated using ES cells obtained therefrom, the genetic background can be changed to that of the C57BL/6 mouse by backcrossing with the C57BL/6 mouse, since its background is of the C57BL/6 mouse, as well as being advantageous in that ovum availability per animal is high and ova are robust.

In establishing ES cells, blastocytes at 3.5 days after fertilization are commonly used. In the present invention, embryos are preferably collected at the 8-cell stage, after culturing until the blastocyte stage, the embryos are used to efficiently obtain a large number of early stage embryos.

Although the ES cells used may be of either sex, male ES cells are generally more convenient for generation of a germ cell line chimera. It is also desirable that sexes are identified as soon as possible to save painstaking culture time.

Methods for sex identification of the ES cell include the method in which a gene in the sex-determining region on the Y-chromosome is amplified by the PCR process and detected. When this method is used, one colony of ES cells (about 50 cells) is sufficient for sex-determination analysis, which karyotype analysis, for example G-banding method, requires about $10^6$ cells; therefore, the first selection of ES cells at the early stage of culture can be based on sex identification, and male cells can be selected early, which saves a significant amount of time at the early stage of culture.

Also, second selection can be achieved by, for example, confirmation of the number of chromosomes by the G-banding method. It is usually desirable that the chromosome number of the obtained ES cells be 100% of the normal number. However, when it is difficult to obtain the cells having the normal number of chromosomes due to physical operations, etc. in the cell establishment, it is desirable that the ES cell is again cloned to a normal cell (e.g., in a mouse cell having the number of chromosomes being 2n=40) after knockout of the gene of the ES cells.

Although the embryonic stem cell line thus obtained shows a very high growth potential, it must be subcultured with great care, since it tends to lose its ontogenic capability. For example, the embryonic stem cell line is cultured at about 37° C. in a carbon dioxide incubator (preferably 5% carbon dioxide and 95% air, or 5% oxygen, 5% carbon dioxide and 90% air) in the presence of LIF (1 to 10000 U/ml) on appropriate feeder cells such as STO fibroblasts, treated with a trypsin/EDTA solution (normally 0.001 to 0.5% trypsin/0.1 to about 5 mM EDTA, preferably about 0.1% trypsin/1 mM EDTA) at the time of passage to obtain separate single cells, which are then plated on freshly prepared feeder cells. This passage is normally conducted every 1 to 3 days; it is desirable that cells be observed at the passage and cells found to be morphologically abnormal in culture, if any, be abandoned.

Where ES cells are allowed to reach a high density in mono-layers or to form cell aggregates in suspension under appropriate conditions, it is possible to differentiate the ES cells to various cell types, for example, pariental and visceral muscles, cardiac muscle or the like [M. J. Evans and M. H. Kaufman, Nature, 292, 154, 1981; G. R. Martin, Proc. Natl. Acad. Sci. U.S.A., 78, 7634, 1981; T. C. Doetschman et al., Journal of Embryology Experimental Morphology, 87, 27, 1985]. The cells deficient in expression of the DNA of the present invention, which are obtained from the differentiated ES cells of the present invention, are useful for studying the FPRL2 of the present invention in vitro or the FPRL2 of the present invention cytologically.

The non-human mammal deficient in expression of the DNA of the present invention can be identified from a normal animal by measuring the mRNA level in the subject animal by a publicly known method, and indirectly comparing the degrees of expression.

As the non-human mammal, the same examples supra can be applied.

With respect to the non-human mammal deficient in expression of the DNA of the present invention, the DNA of the present invention can be made knockout by transferring a targeting vector, prepared as described above, to mouse embryonic stem cells or mouse oocytes, and conducting homologous recombination in which a targeting vector DNA sequence, wherein the DNA of the present invention is inactivated by the transfer, is replaced with the DNA of the present invention on a chromosome of a mouse embryonic stem cell or mouse embryo.

The knockout cells with the disrupted DNA of the present invention can be identified by the southern hybridization analysis using as a probe a DNA fragment on or near the DNA of the present invention, or by the PCR analysis using as primers a DNA sequence on the targeting vector and another DNA sequence at the proximal region of other than the DNA of the present invention derived from mouse used in the targeting vector. When non-human mammal stem cells are used, a cell line wherein the DNA of the present invention is inactivated by homologous recombination is cloned; the resulting clones are injected to, e.g., a non-human mammalian embryo or blastocyst, at an appropriate stage such as the 8-cell stage. The resulting chimeric embryos are transplanted to the uterus of the pseudopregnant non-human mammal. The resulting animal is a chimeric animal constructed with both cells having the normal locus of the DNA of the present invention and those having an artificially mutated locus of the DNA of the present invention.

When some germ cells of the chimeric animal have a mutated locus of the DNA of the present invention, an individual, which entire tissue is composed of cells having a mutated locus of the DNA of the present invention can be selected from a series of offspring obtained by crossing between such a chimeric animal and a normal animal, e.g., by coat color identification, etc. The individuals thus obtained are normally deficient in heterozygous expression of the FPRL2 of the present invention. The individuals deficient in homozygous expression of the FPRL2 of the present invention can be obtained from offspring of the intercross between those deficient in heterozygous expression of the FPRL2 of the present invention.

When an oocyte is used, a DNA solution may be injected, e.g., into the prenucleus by microinjection thereby to obtain a transgenic non-human mammal having a targeting vector introduced in its chromosome. From such transgenic non-human mammals, those having a mutation at the locus of the DNA of the present invention can be obtained by selection based on homologous recombination.

As described above, the individuals in which the DNA of the present invention is rendered knockout permit passage rearing under ordinary rearing conditions, after the individuals obtained by their crossing have proven to have been knockout.

Furthermore, the genital system may be obtained and maintained by conventional methods. That is, by crossing male and female animals each having the inactivated DNA, homozygous animals having the inactivated DNA in both loci can be obtained. The homozygotes thus obtained may be reared so that one normal animal and plural homozygotes are produced from a mother animal to efficiently obtain such homozygotes. By crossing male and female heterozygotes, homozygotes and heterozygotes having the inactivated DNA are proliferated and passaged.

The non-human mammalian embryonic stem cell, in which the DNA of the present invention is inactivated, is very useful for preparing a non-human mammal deficient in expression of the DNA of the present invention.

Since the non-human mammal, in which the DNA of the present invention is inactivated, lacks various biological activities derived from the FPRL2 of the present invention, such an animal can be a disease model suspected of inactivated biological activities of the FPRL2 of the present invention and thus, offers an effective study to investigate the causes for and therapy for these diseases.

(12a) Method of Screening a Compound Having Therapeutic/Preventive Effects on Diseases Caused by Deficiency, Damages, etc. of the DNA of the Present Invention The non-human mammal deficient in expression of the DNA of the present invention can be employed for screening of a compound having therapeutic/preventive effects on diseases caused by deficiency, damages. etc. of the DNA of the present invention.

That is, the present invention provides a method of screening a compound having a therapeutic/preventive effect on diseases caused by deficiency, damages, etc. of the DNA of the present invention, which is characterized by administering a test compound to a non-human mammal deficient in expression of the DNA of the present invention and, observing and measuring a change occurred in the animal.

As the non-human mammal deficient in expression of the DNA of the present invention, which can be employed for the screening method, the same examples as given hereinabove apply.

Examples of the test compound include peptides, proteins, non-peptide compounds, synthetic compounds, fermentation products, cell extracts, plant extracts, animal tissue extracts, blood plasma, etc. These compounds may be novel compounds or publicly known compounds.

The test compound may form salts and may be used in the form of salts with physiologically acceptable acids (e.g., inorganic acids, etc.) or bases (e.g., organic acids, etc.), preferably in the form of physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

Specifically, the non-human mammal deficient in expression of the DNA of the present invention is treated with a test compound, comparison is made with an intact animal for control and a change in each organ, tissue, disease conditions, etc. of the animal is used as an indicator to assess the therapeutic/preventive effects of the test compound.

For treating an animal to be tested with a test compound, for example, oral administration, intravenous injection, etc. are applied, and the treatment can be appropriately selected depending on conditions of the test animal, properties of the test compound, etc. Furthermore, a dose of the test compound to be administered can be appropriately selected depending on the administration methods, nature of the test compound, etc.

When a test compound is administered to a test animal in the screening method and blood sugar level of the test animal increases by at least about 10%, preferably at least 30%, more preferably at least about 50%, the test compound can be selected to be a compound having a therapeutic/preventive effect on the diseases described above.

The compound obtained using the above screening method is a compound selected from the test compounds described above and can be used as a safe and low toxic drug such as an agent for treating/preventing diseases caused by deficiencies, damages, etc. of the FPRL2 of the present invention (for example, asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as, cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endotoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, immunodeficiency, infections, cancer, etc., especially immunodeficiency). In addition, compounds derived from the compound obtained by the screening described above can be used as well.

The compound obtained by the screening method may form salts and may be used in the form of salts with physiologically acceptable acids (e.g., inorganic acids, organic acids, etc.) or bases (e.g., alkali metal salts), preferably in the form of physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

The pharmaceutical comprising the compound obtained by the above screening method or salts thereof can be produced in a manner similar to the method for preparing the pharmaceutical comprising the above-mentioned compound that changes the binding property of the FPRL2 of the present invention and ligand peptide, or signal transduction.

Since the pharmaceutical preparation thus obtained is safe and low toxic, it can be administered to human or non-human mammal (e.g., rat, mouse, guinea pig, rabbit, sheep, swine, bovine, horse, cat, dog, monkey, etc.).

The dose of the compound or its salt may vary depending upon target disease, subject to be administered, route of administration, etc. For example, when the compound is orally administered to the patient (as 60 kg body weight) with immunodeficiency, the compound is generally administered to the patient with schizophrenia in a daily dose of about 0.1 to about 100 mg, preferably about 1.0 to about 50 mg and, more preferably about 1.0 to about 20 mg. In parenteral administration, a single dose of said compound or its salt may vary depending upon target subject, target disease, etc. When the compound or its salt is administered to the patient (as 60 kg body weight) with immunodeficiency in the form of an injectable preparation, it is advantageous to administer the compound intravenously to the patient in a daily dose of about 0.01 to about 30 mg, preferably about 0.1 to about 20 mg, and more preferably about 0.1 to about 10 mg. For other animal species, the corresponding dose as converted per 60 kg body weight can be administered.

(12b) Method of Screening a Compound that Promotes or Inhibits the Activity of a Promoter to the DNA of the Present Invention The present invention provides a method of screening a compound or its salts that promote or inhibit the activity of a promoter to the DNA of the present invention, which is characterized by administering a test compound to a non-human mammal deficient in expression of the DNA of the present invention and detecting the expression of the reporter gene.

In the screening method described above, an animal in which the DNA of the present invention is inactivated by introducing a reporter gene and the reporter gene is expressed under control of a promoter to the DNA of the present invention is used as the non-human mammal deficient in expression of the DNA of the present invention among the aforesaid non-human mammals deficient in expression of the DNA of the present invention.

The same examples of the test compound apply to specific compounds used for the screening.

As the reporter gene, the same specific examples apply to this screening method. Preferably, there are used β-galactosidase (lacZ), soluble alkaline phosphatase gene, luciferase gene and the like.

Since the reporter gene is present under control of a promoter to the DNA of the present invention in the non-human mammal deficient in expression of the DNA of the present invention wherein the DNA of the present invention is substituted with the reporter gene, the activity of the promoter can be detected by tracing the expression of a substance encoded by the reporter gene.

When a part of the DNA region encoding the FPRL2 of the present invention is substituted with, e.g., β-galactosidase gene (lacZ) derived from *Escherichia coli*, β-galactosidase is expressed in a tissue where the FPRL2 of the present invention should originally be expressed, instead of the FPRL2 of the present invention. Thus, the expression state of the FPRL2 of the present invention can be readily observed in vivo of an animal by staining with a reagent, e.g., 5-bromo-4-chloro-3-indolyl-β-galactopyranoside (X-gal) which is substrate for β-galactosidase. Specifically, a mouse deficient in the FPRL2 of the present invention, or its tissue section is fixed with glutaraldehyde, etc. After washing with phosphate buffered saline (PBS), the system is reacted with a staining solution containing X-gal at room temperature or about 37° C. for approximately 30 minutes to an hour. After the β-galactosidase reaction is terminated by washing the tissue preparation with 1 mM EDTA/PBS solution, the color formed is observed. Alternatively, mRNA encoding lacZ may be detected in a conventional manner.

The compound or salts thereof obtained using the screening method described above are compounds that are selected from the test compounds described above and that promote or inhibit the promoter activity to the DNA of the present invention.

The compound obtained by the screening method may form salts and may be used in the form of salts with physiologically acceptable acids (e.g., inorganic acids, etc.) or bases (e.g., organic acids, etc), preferably in the form of physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

Since the compound or its salt that promotes the promoter activity to the DNA of the present invention can promote the expression of the FPRL2 of the present invention and can promote the function of said FPRL2, the compound or its salt is useful as a drug such as an agent for preventing/treating diseases associated with dysfunction of the FPRL2 of the present invention. Specifically, the compound can be used as a safe and low-toxic drug such as an agent for preventing/treating, e.g., asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endotoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, immunodeficiency, infections, cancer, etc., especially immunodeficiency.

Since the compound or its salt that inhibits the activity of a promoter for the DNA of the present invention can inhibit the expression of the FPRL2 of the present invention and inhibit the function of the FPRL2, the compound or its salt is useful as a drug such as an agent for preventing/treating diseases associated with overexpression of the FPRL2 of the present invention, for example, asthma, allergic disease, inflammation, inflammatory eye diseases, Addison's disease, autoimmune hemolytic anemia, systemic lupus erythematosus, psoriasis, rheumatism, central nervous diseases (e.g., cerebrovascular disorders such as cerebral hemorrhage, cerebral infarction, etc., head injury, spinal cord injury, cerebral edema, multiple sclerosis, etc.), neurodegenerative diseases (e.g., Alzheimer's disease, Parkinson's disease, amyotrophic lateral sclerosis (ALS), AIDS encephalopathy), meningitis, diabetes mellitus, arthritis (e.g., chronic articular rheumatism, arthritis deformans, rheumatoid spondylitis, gouty arthritis, synovitis), toxemia (e.g., sepsis, septic shock, endotoxic shock, Gram-negative sepsis, toxic shock syndrome), inflammatory bowel diseases (e.g., Crohn's disease, ulcerative colitis), inflammatory pulmonary diseases (e.g., chronic pneumonia, silicosis, pulmonary sarcoidosis, pulmonary tuberculosis), or cachexia (e.g., infection-induced cachexia, cancerous cachexia, acquired immunodeficiency syndrome (AIDS)-induced cachexia), arteriosclerosis, Creutzfeldt-Jakob disease, viral infections (e.g., viral infections such as cytomegalovirus, influenza virus, herpes virus, etc.), angina pectoris, myocardial infarction, congestive heart failure, hepatitis, posttransplantational hyperimmunization, dialysis hypotension, disseminated intravascular coagulation syndrome, infections or cancer.

In addition, compounds derived from the compound obtained by the screening described above can be used as well.

The pharmaceutical comprising the compound obtained by the above screening method or salts thereof can be manufactured in a manner similar to the method for preparing the pharmaceutical comprising the compound that changes the binding property of the FPRL2 of the present invention to the ligand peptide described above.

Since the pharmaceutical preparation thus obtained is safe and low toxic, it can be administered to, for example, human or non-human mammal (e.g., rat, mouse, guinea pig, rabbit, sheep, swine, bovine, horse, cat, dog, monkey, etc.).

The dose of the compound or its salt may vary depending upon target disease, subject to be administered, route of administration, etc. For example, when the compound that promotes the activity of a promoter for the DNA of the present invention is orally administered to the patient (as 60 kg body weight) with immunodeficiency, the compound is generally administered in a daily dose of about 0.1 to about 100 mg, preferably about 1.0 to about 50 mg and, more preferably about 1.0 to about 20 mg. In parenteral administration, a single dose of the compound or its salt may vary depending upon target subject, target disease, etc. For example, when the compound that promotes the activity of a promoter for the DNA of the present invention is administered to the patient (as 60 kg body weight) with immunodeficiency in the form of an injectable preparation, it is advantageous to administer the compound intravenously in a daily dose of about 0.01 to about 30 mg, preferably about 0.1 to about 20 mg, and more preferably about 0.1 to about 10 mg. For other animal species, the corresponding dose as converted per 60 kg body weight can be administered.

As stated above, the non-human mammal deficient in expression of the DNA of the present invention is extremely useful for screening the compound or its salt that promotes or inhibits the promoter activities to the DNA of the present invention and can greatly contribute to elucidation of causes for various diseases suspected of deficiency in expression of the DNA of the present invention and for the development of preventive/therapeutic drug for these diseases.

Also, a so-called transgenic animal (gene transferred animal) can be prepared by using a DNA containing the promoter region of the FPRL2 of the present invention, ligating genes encoding various proteins at the downstream and injecting the same into oocyte of an animal. It is thus possible to synthesize the FPRL2 of the present invention therein specifically and study its activity in vivo. When an appropriate reporter gene is ligated to the promoter site described above and a cell line that expresses the gene is established, the resulting system can be utilized as the search system for a low molecular compound having the action of specifically promoting or inhibiting the in vivo productivity of the FPRL2 of the present invention itself.

In the specification and drawings, where bases, amino acids, etc. are denoted by abbreviations, they are in accordance with the IUPAC-IUB Commission on Biochemical Nomenclature or by the common codes in the art, examples of which are shown below. For amino acids that may have the optical isomer, L form is presented unless otherwise indicated.

DNA: deoxyribonucleic acid
cDNA: complementary deoxyribonucleic acid
A: adenine
T: thymine
G: guanine
C: cytosine
RNA: ribonucleic acid
mRNA: messenger ribonucleic acid
dATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediaminetetraacetic acid
SDS: sodium dodecyl sulfate
Gly: glycine
Ala: alanine
Val: valine
Leu: leucine
Ile: isoleucine
Ser: serine
Thr: threonine
Cys: cysteine
Met: methionine
Glu: glutamic acid
Asp: aspartic acid
Lys: lysine
Arg: arginine
His: histidine
Phe: phenylalanine
Tyr: tyrosine
Trp: tryptophan
Pro: proline
Asn: asparagine
Gln: glutamine
pGlu: pyroglutamic acid
*: corresponding to termination codon
Me: methyl group
Et: ethyl group
Bu: butyl group
Ph: phenyl group
TC: thiazolidine-4(R)-carboxamido group Substituents, protecting groups and reagents generally used in this specification are presented as the codes below.

Tos: p-toluenesulfonyl
CHO: formyl
Bzl: benzyl
$Cl_2$-Bzl: 2,6-dichlorobenzyl
Bom: benzyloxymethyl
Z: benzyloxycarbonyl
Cl-Z: 2-chlorobenzyloxycarbonyl
Br-Z: 2-bromobenzyl oxycarbonyl
Boc: t-butoxycarbonyl
DNP: dinitrophenol
Trt: trityl
Bum: t-butoxymethyl
Fmoc: N-9-fluorenyl methoxycarbonyl
HOBt: 1-hydroxybenztriazole
HOOBt: 3,4-dihydro-3-hydroxy-4-oxo-1,2,3-benzotriazine
HONB: 1-hydroxy-5-norbornene-2,3-dicarboxyimide
DCC: N,N'-dicyclohexylcarbodiimide The sequence identification numbers in the sequence listing of the specification indicates the following sequence, respectively.

SEQ ID NO: 1
This shows the amino acid sequence of human-derived FPRL2 of the present invention.

SEQ ID NO: 2
This shows the base sequence of cDNA encoding human-derived FPRL2 of the present invention.

SEQ ID NO: 3
This shows the amino acid sequence of GHRP-6. Trp is a D-form.

SEQ ID NO: 4
This shows the amino acid sequence of SCPA.

SEQ ID NO: 5
This shows the amino acid sequence of human RFRP-1-12 (hRFRP-1-12)

SEQ ID NO: 6
This shows the amino acid sequence of porcine neuropeptide Y (pNPY).

SEQ ID NO: 7
This shows the amino acid sequence of human neuromedin C (hNeuromedin C).

EXAMPLES

Hereinafter, the present invention will be described in more detail, by referring to EXAMPLES, but is not deemed to limit the scope of the present invention. Gene using *Escherichia coli* was performed in accordance with the method described in Molecular Cloning.

Example 1

Construction of the Assay System for Intracellular cAMP Level using AlphaScreen

Orphan G protein-coupled receptor protein-expressing CHO cells were inoculated in one flask of 150 cm$^2$ at 1×10$^7$ cells, followed by incubation at 37° C. in a $CO_2$ incubator. Subsequently to the incubation, the cells were detached using 0.5 mM EDTA/PBS, and washed with PBS. The cells were then suspended at a density of 1×10$^7$ cells/ml in Buffer 1 (HBSS+0.1% BSA, 25 mM HEPES, pH 7.3, 0.5 mM IBMX). This cell suspension, 440 µl, was mixed with 22 µl of anti-cAMP acceptor beads of AlphaScreen cAMP Assay Kit (Perkin Elmer) and 638 µl of Buffer 1. The resulting mixture was dispensed on a white 96-well plate (Costar) by 10 µl each. Next, 10 µl each of a Buffer 1 dilution or solution of the compound to be screened was added to each well. In this case, the cell suspension was not given in one row of the plate but only a mixture of 9 µl of anti-cAMP acceptor beads and 441 µl of Buffer 1 was charged and instead of the compound, a serial dilution of cAMP was added thereto. This was made standard. The plate in which a mixture of the cell suspension and the compound was charged was kept shaken at room temperature for 30 minutes. Thirty minutes after, a mixture of 20 µl of Biotinyl camp and 82 µl of Streptavin donor beads of AlphaScreen cAMP Assay kit with 40 ml of Buffer 2 (HBSS+ 0.1% BSA, 25 mM HEPES, pH 7.3, 1.5% Tween 20) was added to all wells of the plate by 30 µl each. The plate was kept shaken at room temperature for 3 hours and the fluorescence intensity was measured by Fusion a (Perkin Elmer). Using the cAMP standard charged in the plate, the cAMP level in each well was calculated. In addition to human FPRL2-expressing CHO cells, three orphan G protein-coupled receptor protein-expressed CHO cells were added and the resulting compound library was provided for screening using the assay system described above. Some of the C-terminal amide peptides were found to show the activity of specifically inhibiting intracellular cAMP production in human FPRL2-expressing CHO cells. Accordingly, 64 C-terminal amide peptides were picked up and the reactivity with human FPRL2-expressing cells was again examined using the same assay system. As a result, it was observed that some of the C-terminal amide peptides showed the intracellular cAMP production inhibition activity in human FPRL2-expressing CHO cells.

Example 2

C-Terminal Amide Peptides Exhibiting the Intracellular cAMP Production Inhibition Activity Specific to Human FPRL2

Figure 2:
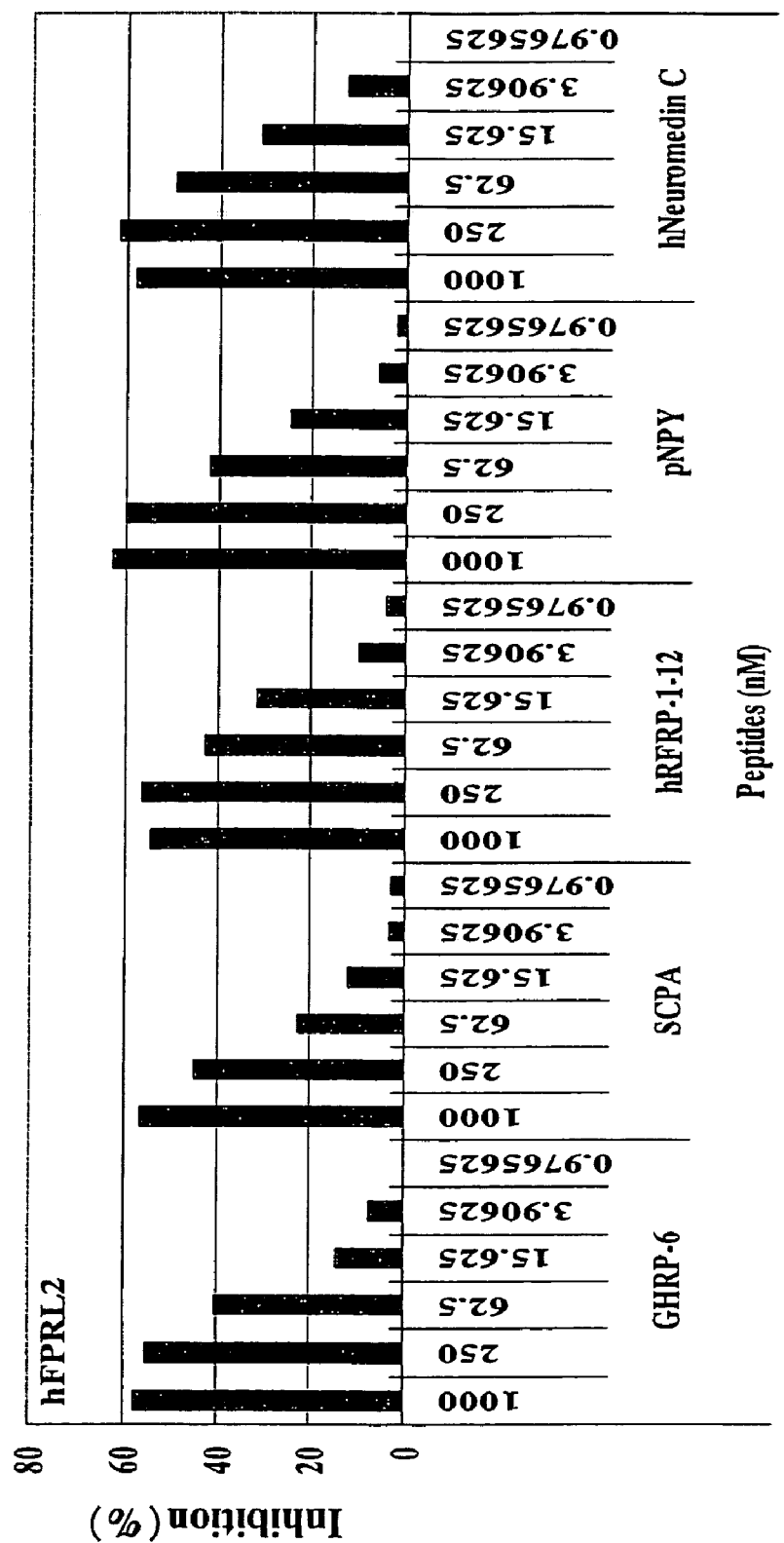
FIG. 2 shows the results obtained by assaying the activity of inhibiting intracellular cAMP production level when various ligand peptides were added to human FPRL2-expressed CHO cells (hFPRL2). "Peptides (nM)" on the abscissa indicates the amounts of various ligand peptides added. "Inhibition (%)" on the ordinate indicates the activity of inhibiting intracellular cAMP production when various ligand peptides were added.
Figure 3:
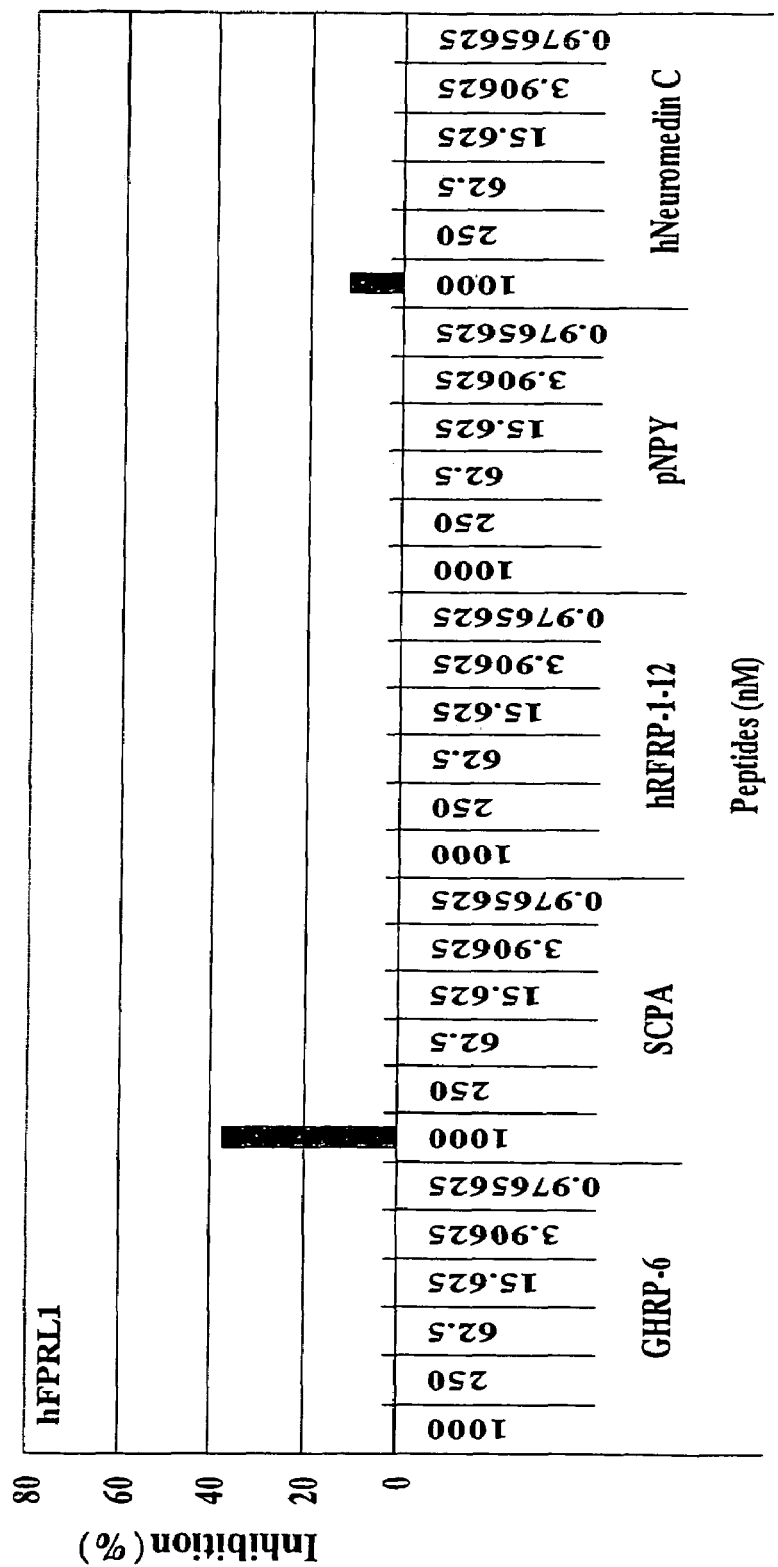
FIG. 3 shows the results obtained by assaying the activity of inhibiting intracellular cAMP production level when various ligand peptides were added to human FPRL1-expressed CHO cells (hFPRL1). "Peptides (nM)" on the abscissa indicates the amounts of various ligand peptides added. "Inhibition (%)" on the ordinate indicates the activity of inhibiting intracellular cAMP production when various ligand peptides were added.
Figure 4:
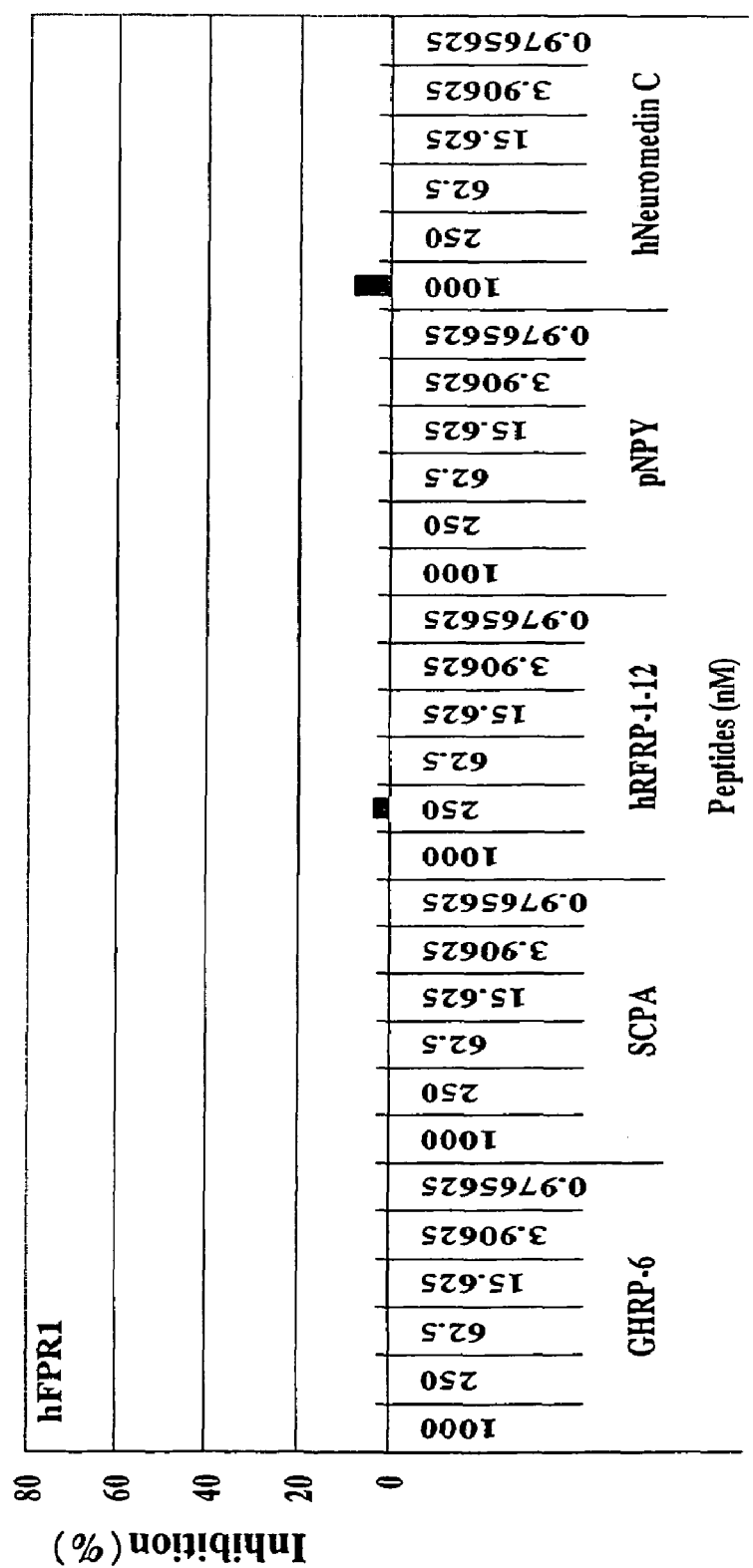
FIG. 4 shows the results obtained by assaying the activity of inhibiting intracellular cAMP production level when various ligand peptides were added to human FPRL1-expressed CHO cells (hFPRL1). "Peptides (nM)" on the abscissa indicates the amounts of various ligand peptides added. "Inhibition (%)" on the ordinate indicates the activity of inhibiting intracellular cAMP production when various ligand peptides were added.

Five peptides (GHRP-6, SCPA, hRFRP-1-12, pNPY and hNeuromedin C) were chosen from the peptides found to show the activity on human FPRL2 in EXAMPLE 1 and the reactivity was examined for human FPRL1 and human FPR1, in addition to human FPRL2 (FIGS. 1 through 4). The results indicate that these peptides exhibited the intracellular cAMP production inhibition activity specific to human FPRL2 (FIG. 2).

Example 3

Analysis of FPRL2 in the Affected Synovial Membrane of the Patient with RA (Chronic Articular Rheumatism)

To quantify the expression level of mRNA, ABI PRISM 7900HT (Applied Biosystems, Inc.) was used. A primer and a probe used for the quantification were designed based on the base sequence of human FPRL2, using a Primer Express software (Applied Biosystems, Inc.). The cDNA used as a sample was prepared by extracting total RNA from the affected synovial membranes of two patients with RA, followed by reverse transcription of 25 µg out of the total RNA using a random primer. The reaction was carried out in accordance with the attached protocol using reverse transcriptase SuperScriptII (GIBCO BRL, Inc.) and the product was precipitated in ethanol to become a solution of 1000 µl. The reaction solution for the quantification was prepared by adding 1.0 µl each of the primer (0.9 µM), probe (0.25 µM) and the sample cDNA to the reaction solution in 20 µl/well, following the protocol of TaqMan Universal PCR Master Mix (Applied Biosystems, Inc.). The reaction on ABI PRISM 7900HT was carried out at 50° C. (2 minutes) and 95° C. (10 minutes), followed by 40 cycles of 95° C. (15 seconds) and 60° C. (1 minute). The affected synovial membranes of the patients with RA showed a higher expression of FPRL2 in the two cases (100,000 copies/25 ng total RNA).

INDUSTRIAL APPLICABILITY

The FPRL2 of the present invention, its partial peptide or a salt thereof, or the DNA encoding the FPRL2 of the present invention or its partial peptide can be used as a low-toxic and safe pharmaceutical such as an agent for preventing/treating, e.g., asthma, allergic disease, inflammation, inflammatory eye diseases, Addison's disease, autoimmune hemolytic anemia, systemic lupus erythematosus, psoriasis, rheumatism, cerebral hemorrhage, cerebral infarction, head injury, spinal cord injury, cerebral edema, multiple sclerosis, Alzheimer's disease, Parkinson's disease, amyotrophic lateral sclerosis (ALS), AIDS encephalopathy, meningitis, diabetes mellitus, chronic articular rheumatism, arthritis deformans, rheumatoid spondylitis, gouty arthritis, synovitis, toxemia, Crohn's disease, ulcerative colitis, chronic pneumonia, silicosis, pulmonary sarcoidosis, pulmonary tuberculosis, cachexia, arteriosclerosis, Creutzfeldt-Jakob disease, viral infections angina pectoris, myocardial infarction, congestive heart failure, hepatitis, posttransplantational hyperimmunization, dialysis hypotension, disseminated intravascular coagulation syndrome, disseminated intravascular coagulation syndrome, immunodeficiency, infections or cancer.

By using the FPRL2 of the present invention, its partial peptide or a salt thereof and the ligand peptide, the compound that changes the binding property of the ligand peptide to the FPRL2 of the present invention, its partial peptide or a salt thereof can be efficiently screened.

The invention claimed is:

1. A method of screening for a compound or a salt thereof, that changes the binding property of a G protein-coupled receptor protein comprising the amino acid sequence represented by SEQ ID NO: 1, or a salt thereof, to a ligand peptide comprising the amino acid sequence represented by SEQ ID NO:6, its amide, or a salt thereof, the method comprising: contacting said receptor protein, or a salt thereof, with said ligand peptide, its amide, or a salt thereof, and determining a level of binding by said ligand peptide, its amide, or salt thereof, to said receptor protein or salt thereof, in the presence of said compound or salt thereof, and in the absence of said compound or salt thereof, wherein a difference in binding levels by said ligand peptide, its amide or salt thereof, to said receptor protein or salt thereof, in the presence of said compound or salt thereof, compared to in the absence of said compound or salt thereof, indicates that the compound changes the binding property of said receptor protein to said ligand peptide.

2. A method of screening for an agonist or antagonist of a G protein-coupled receptor protein comprising the amino acid sequence represented by SEQ ID NO: 1, or a salt thereof, the method comprising contacting said receptor protein, or a salt thereof, with a ligand peptide comprising the amino acid sequence represented by SEQ ID NO:6, its amide, or a salt thereof, and determining a level of binding by said ligand peptide, its amide, or salt thereof, to said receptor protein or salt thereof, in the presence of a test compound or salt thereof, and in the absence of said compound or salt thereof; wherein a decrease in binding levels by said ligand peptide, its amide or salt thereof, in the presence of said test compound or salt thereof, compared to in the absence of said test compound, indicates said test compound is an antagonist.

3. A kit for screening a compound or a salt thereof, that changes the binding property of a G protein-coupled receptor protein comprising the amino acid sequence represented by SEQ ID NO: 1, or a salt thereof, to a ligand peptide comprising the amino acid sequence represented by SEQ ID NO:6, its amide or a salt thereof, wherein said kit comprises—said receptor protein, or a salt thereof, and (2) said ligand peptide, its amide, or a salt thereof.

4. A kit for screening for an agonist or antagonist to a G protein-coupled receptor protein comprising the amino acid sequence represented by SEQ ID NO: 1, or a salt thereof, wherein said kit comprises (1) said receptor protein, or a salt thereof, and (2) a ligand peptide comprising the amino acid sequence represented by SEQ ID NO:6, its amide, or a salt thereof.

5. A method of screening for a compound or a salt thereof, that changes the binding property of a G protein-coupled receptor protein comprising the amino acid sequence having at least 85% homology to the amino acid sequence represented by SEQ ID NO: 1, or a salt thereof, to a ligand peptide comprising the amino acid sequence represented by SEQ ID NO:6, its amide, or a salt thereof, the method comprising: contacting said receptor protein, or a salt thereof, with said ligand peptide, its amide, or a salt thereof, and determining a level of binding by said ligand peptide, its amide, or salt thereof, to said receptor protein or salt thereof, in the presence of said compound or salt thereof, and in the absence of said compound or salt thereof, wherein a difference in binding levels by said ligand peptide, its amide or salt thereof, to said receptor protein or salt thereof, in the presence of said compound or salt thereof, compared to in the absence of said compound or salt thereof, indicates that the compound changes the binding property of said receptor protein to said ligand peptide.

6. A method of screening for an agonist or antagonist of a G protein-coupled receptor protein comprising the amino acid sequence having at least 85% homology to the amino acid sequence represented by SEQ ID NO: 1, or a salt thereof, the method comprising contacting said receptor protein, or a salt thereof, with a ligand peptide comprising the amino acid sequence represented by SEQ ID NO:6, its amide, or a salt thereof, and determining a level of binding by said ligand peptide, its amide, or salt thereof, to said receptor protein or salt thereof; in the presence of a test compound or salt thereof, and in the absence of said compound or salt thereof, wherein a decrease in binding levels by said ligand peptide, its amide or salt thereof, in the presence of said test compound or salt thereof, compared to in the absence of said test compound or salt thereof, indicates said test compound is an antagonist.

7. A kit for screening a compound or a salt thereof, that changes the binding property of a G protein-coupled receptor protein comprising the amino acid sequence having at least 85% homology to the amino acid sequence represented by SEQ ID NO: 1, or a salt thereof, to a ligand peptide comprising the amino acid sequence represented by SEQ ID NO:6, its amide, or a salt thereof, wherein said kit comprises—said receptor protein, or a salt thereof, and (2) said ligand peptide, its amide, or a salt thereof.

8. A kit for screening for an agonist or antagonist to a G protein-coupled receptor protein comprising the amino acid sequence having at least 85% homology to the amino acid sequence represented by SEQ ID NO: 1, or a salt thereof, wherein said kit comprises (1) said receptor protein, or a salt thereof, and (2) a ligand peptide comprising the amino acid sequence represented by SEQ ID NO:6, its amide, or a salt thereof.

9. A method of screening for a compound or a salt thereof, that changes the binding property of a G protein-coupled receptor protein comprising the amino acid sequence having at least 95% homology to the amino acid sequence represented by SEQ ID NO: 1, or a salt thereof, to a ligand peptide comprising the amino acid sequence represented by SEQ ID NO:6, its amide, or a salt thereof, the method comprising: contacting said receptor protein, or a salt thereof, with said ligand peptide, its amide, or a salt thereof, and determining a level of binding by said ligand peptide, its amide, or salt thereof, to said receptor protein or salt thereof, in the presence of said compound or salt thereof, and in the absence of said compound or salt thereof, wherein a difference in binding levels by said ligand peptide, its amide or salt thereof, to said receptor protein or salt thereof, in the presence of said compound or salt thereof, compared to in the absence of said compound or salt thereof, indicates that the compound changes the binding property of said receptor protein to said ligand peptide.

10. A method of screening for an agonist or antagonist of a G protein-coupled receptor protein comprising the amino acid sequence having at least 95% homology to the amino acid sequence represented by SEQ ID NO: 1, or a salt thereof, the method comprising contacting said receptor protein, or a salt thereof, with a ligand peptide comprising the amino acid sequence represented by SEQ ID NO:6, its amide, or a salt thereof, and determining a level of binding by said ligand peptide, its amide, or salt thereof, to said receptor protein or salt thereof; in the presence of a test compound or salt thereof, and in the absence of said compound or salt thereof, wherein a decrease in binding levels by said ligand peptide, its amide or salt thereof, in the presence of said test compound or salt thereof, compared to in the absence of said test compound or salt thereof, indicates said test compound is an antagonist.

* * * * *